(12) United States Patent
Rock

(10) Patent No.: US 8,484,254 B1
(45) Date of Patent: Jul. 9, 2013

(54) RESEARCH STUDY DATABASE TO COMPARE DIFFERENT RESEARCH STUDIES AND TO COMPARE ACTUAL ACTIVITIES COMPARED TO THE PROTOCOL

(75) Inventor: Jason T. Rock, Philadelphia, PA (US)

(73) Assignee: GlobalSubmit, Inc., Philadelphia, PA (US)

( * ) Notice: Subject to any disclaimer, the term of this patent is extended or adjusted under 35 U.S.C. 154(b) by 0 days.

(21) Appl. No.: 13/218,637

(22) Filed: Aug. 26, 2011

Related U.S. Application Data

(60) Provisional application No. 61/377,236, filed on Aug. 26, 2010.

(51) Int. Cl.
*G06F 7/00* (2006.01)
*G06F 17/30* (2006.01)

(52) U.S. Cl.
USPC .......................... 707/803; 707/804; 707/806

(58) Field of Classification Search
USPC .......................................... 707/803, 804, 806
See application file for complete search history.

(56) References Cited

U.S. PATENT DOCUMENTS 6,925,599 B2 * 8/2005 Wood ............................ 715/229
2007/0294110 A1 * 12/2007 Settimi ............................ 705/3

* cited by examiner

*Primary Examiner* — Mariela Reyes
(74) *Attorney, Agent, or Firm* — Panitch Schwarze Belisario & Nadel LLP

(57) ABSTRACT

A computer is provided for processing data from a plurality of studies of investigational products in a manner that allows the data from one study to be compared to one or more other studies. Each study includes a plurality of planned activities, a plurality of actual activities, and a plurality of assessments. The computer includes a memory, a database schema and a database. The memory is configured to store an operating system which includes an object-oriented database engine. The database schema is maintained by the object-oriented database engine of the operating system. The database schema has a plurality of uniquely defined database objects. For each study, the uniquely defined database objects include respective sets of objects that store the plurality of planned activities, actual activities, and assessments. The database is populated with data associated with the plurality of planned activities, actual activities, and assessments. The respective sets of objects that store the plurality of planned activities, actual activities, and assessments for each study share common attributes and relationships. Each planned activity, actual activity, and assessment has an associated data type that is the same for different studies.

36 Claims, 33 Drawing Sheets

Supplies

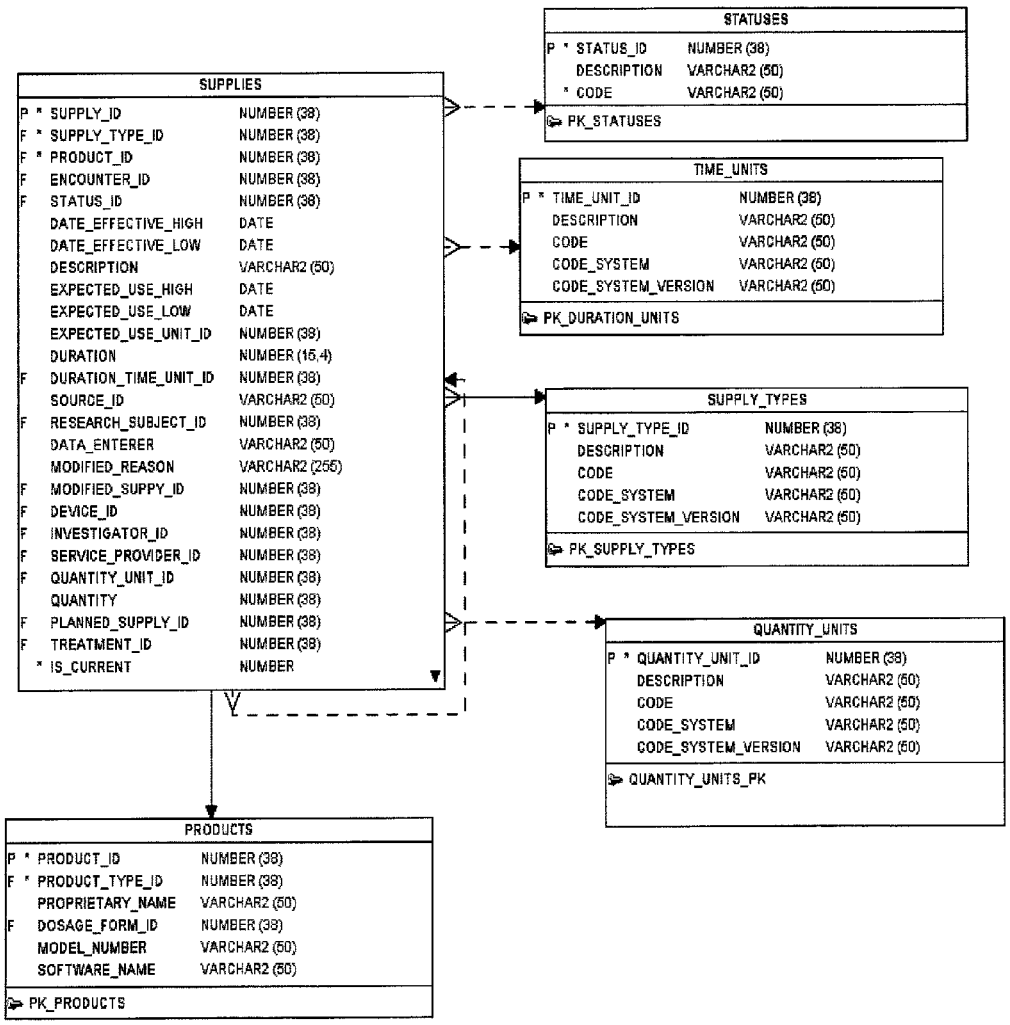
Figure 1: Supplies

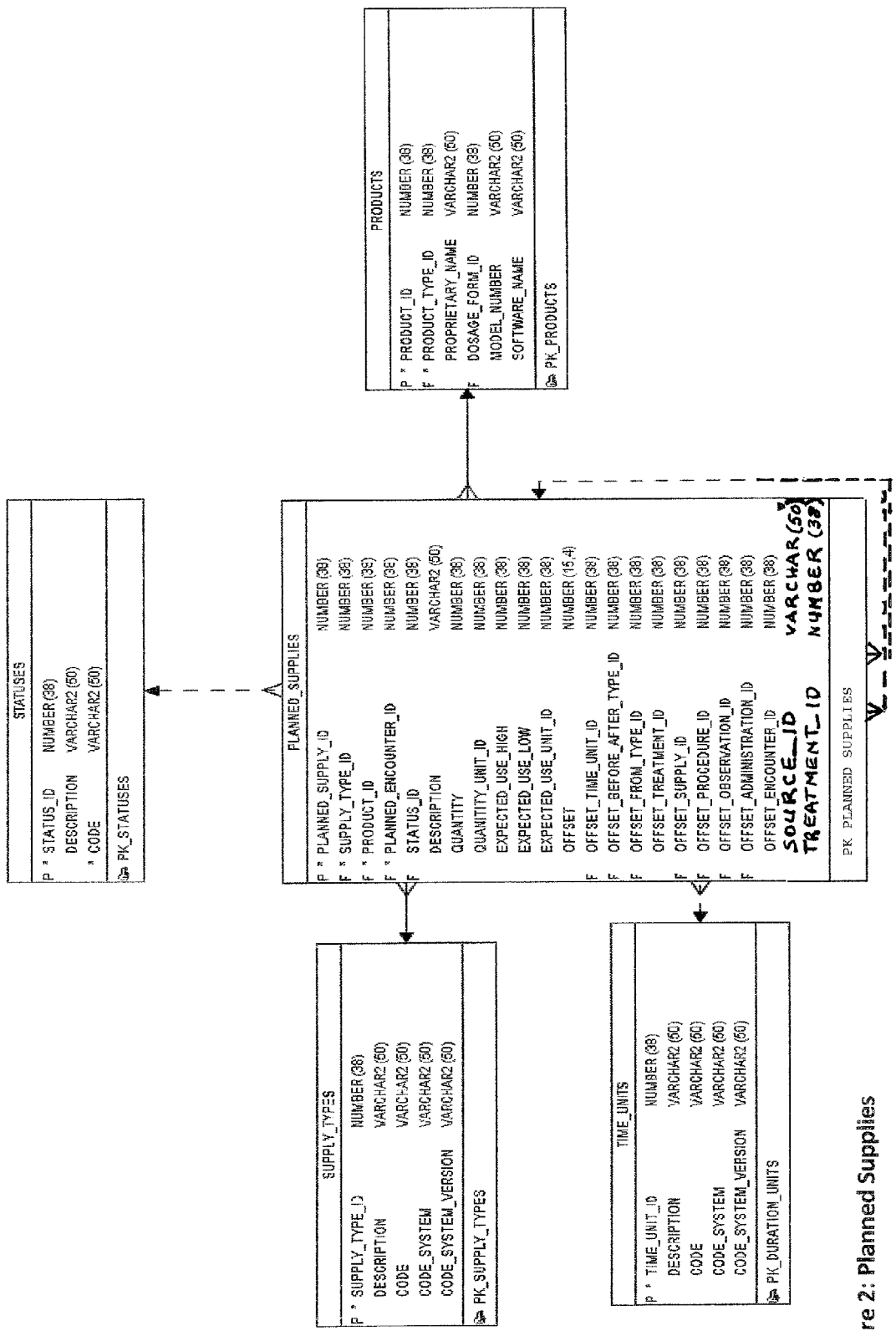
Figure 2: Planned Supplies

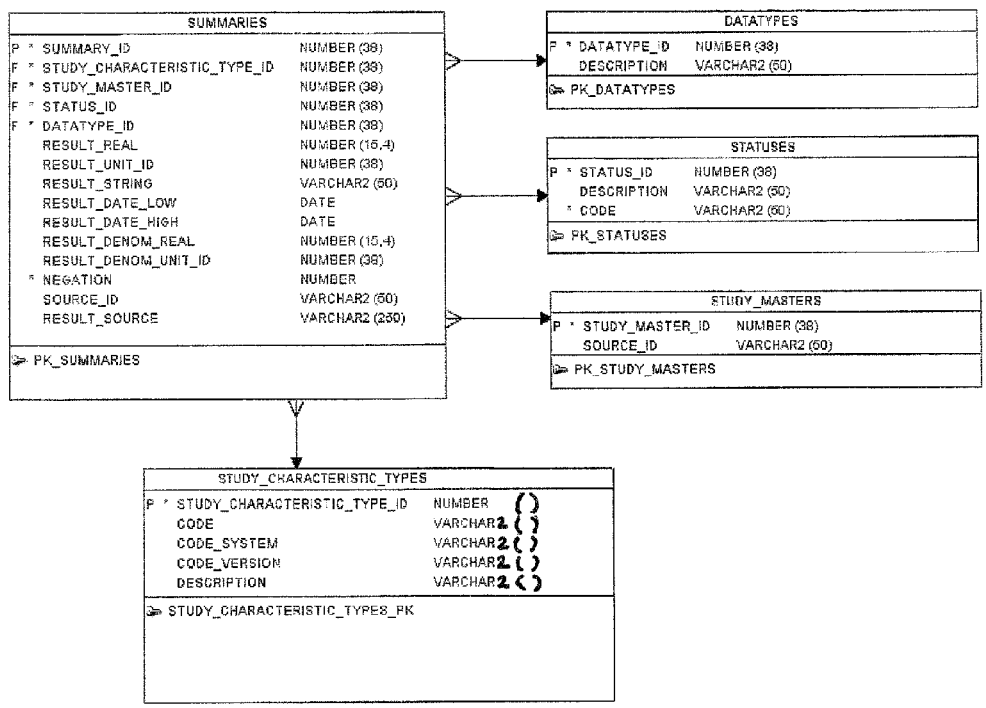
Figure 3: Summaries of the Study

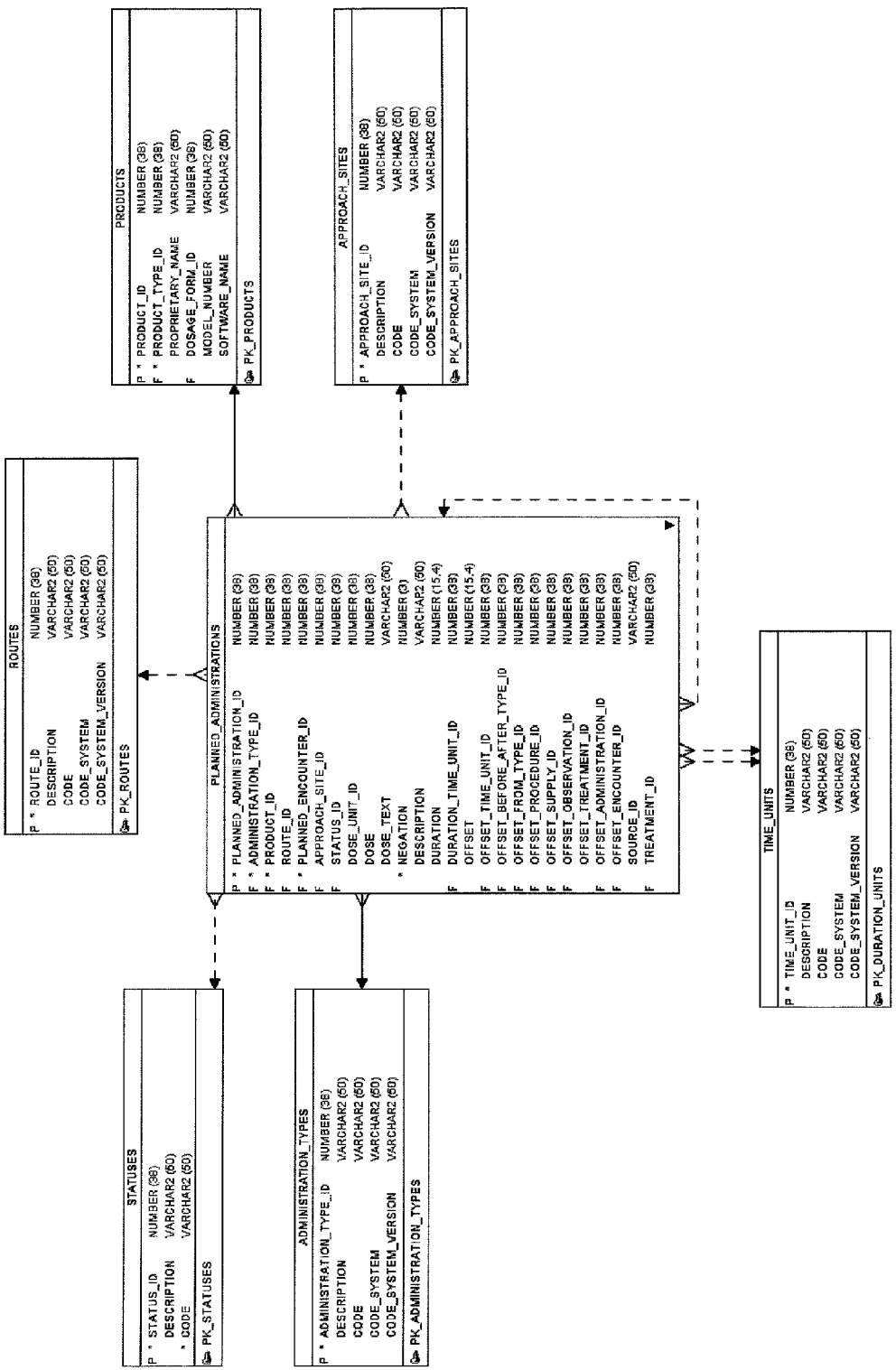
Figure 4: Planned Substance Administration

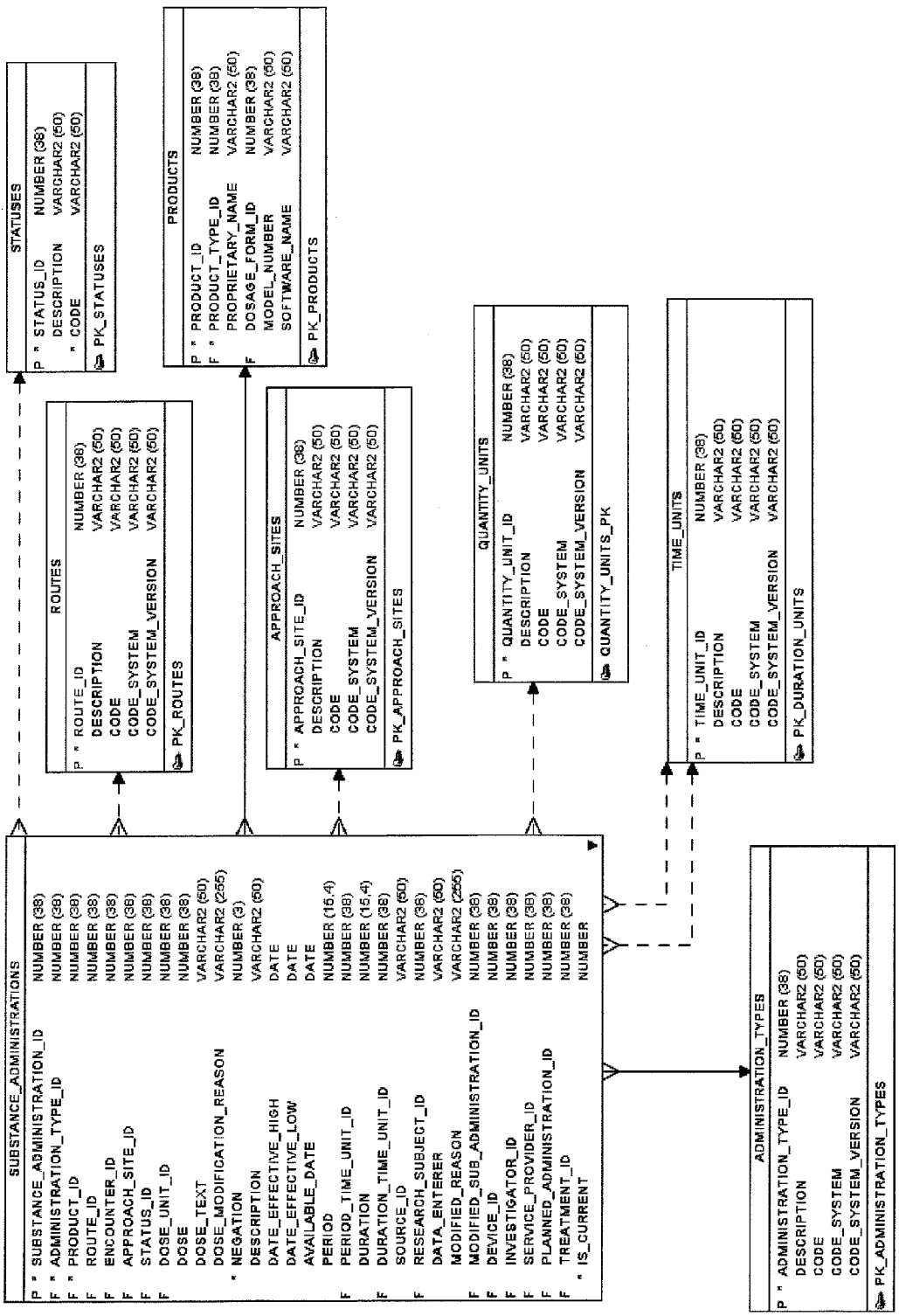
Figure 5: Substance Administration

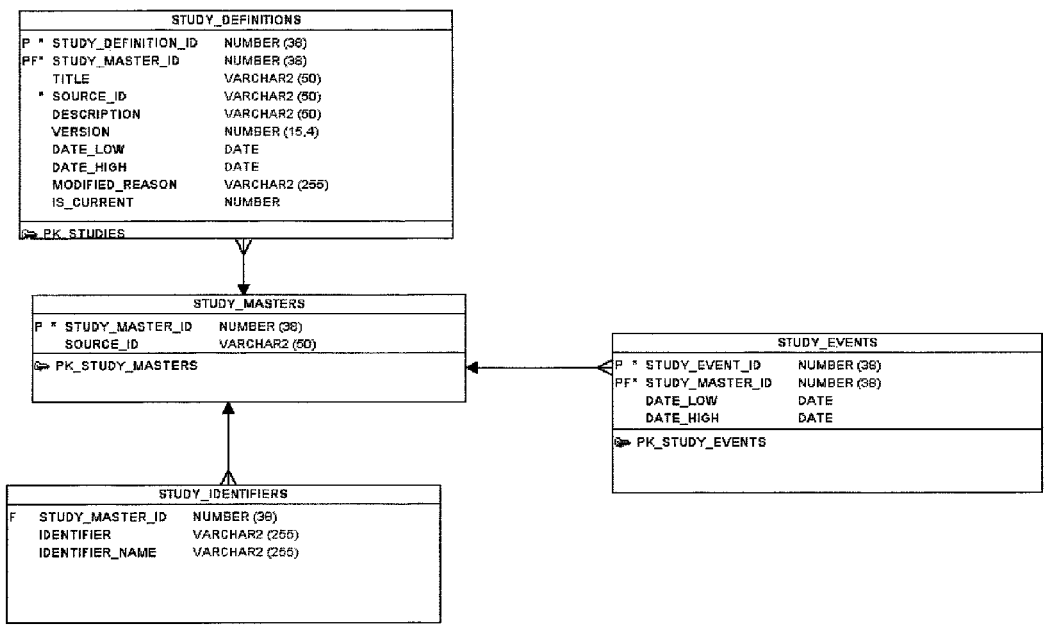
Figure 6: Study Amendments

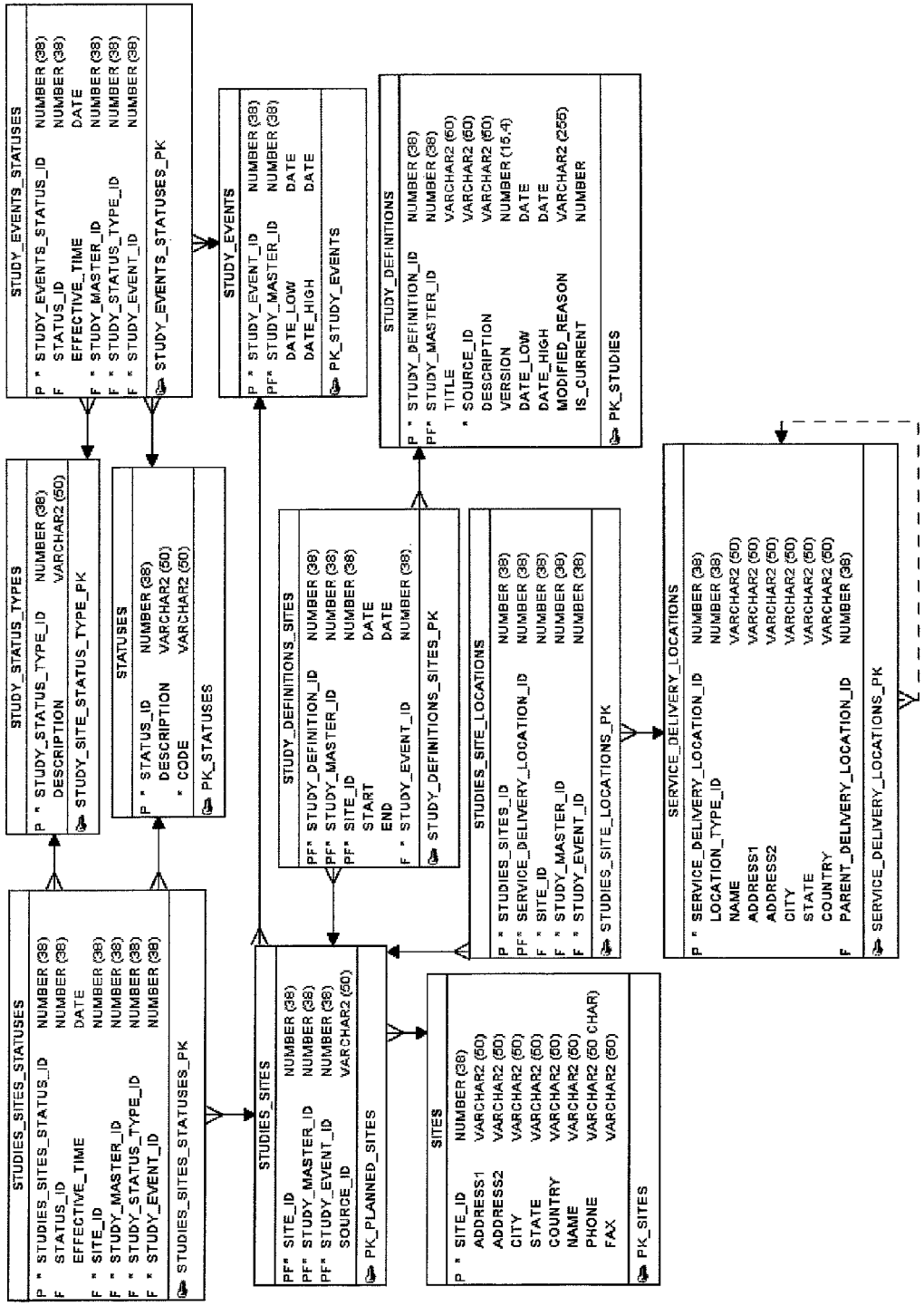
Figure 7: Sites and Service Location

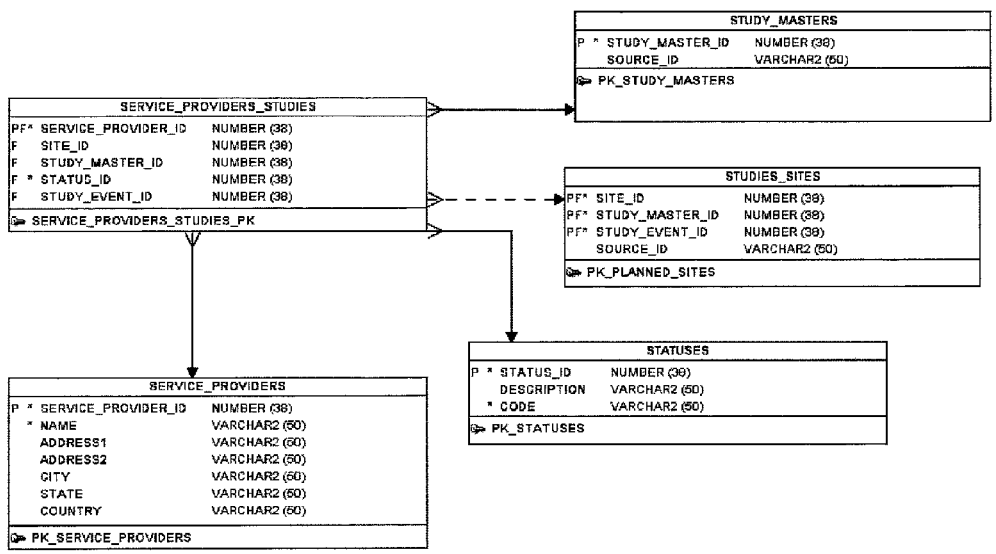
Figure 8: Service Provider

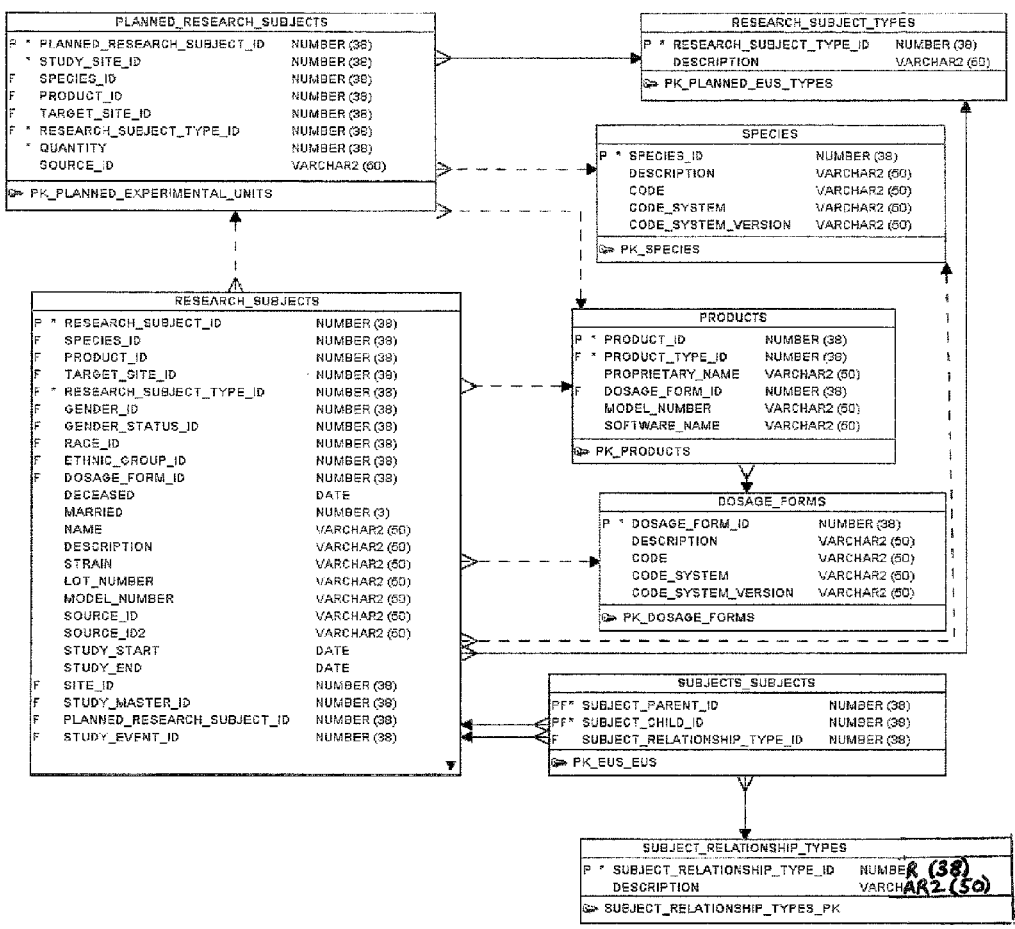
Figure 9a: Research Subject

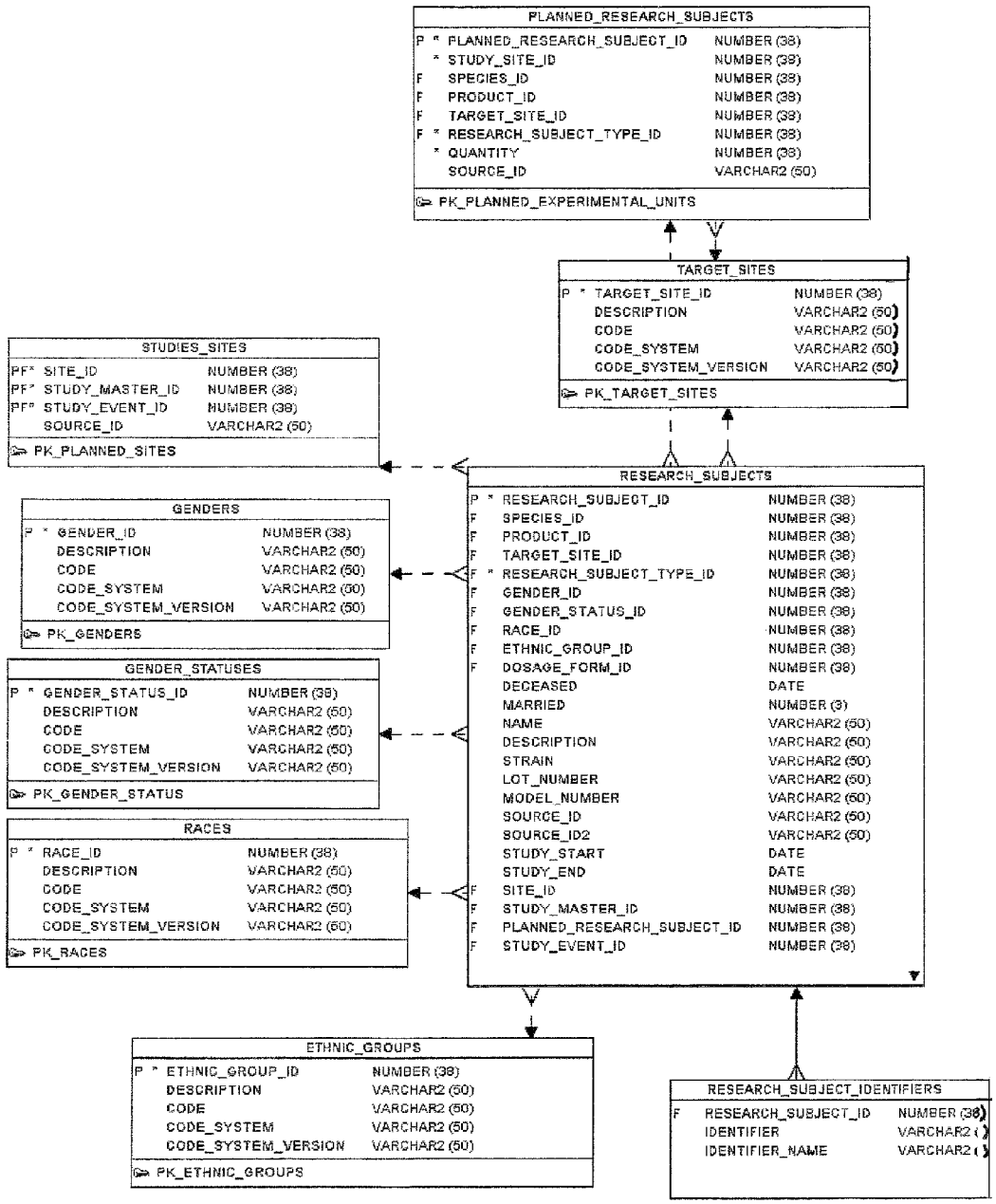
Figure 9b: Research Subject

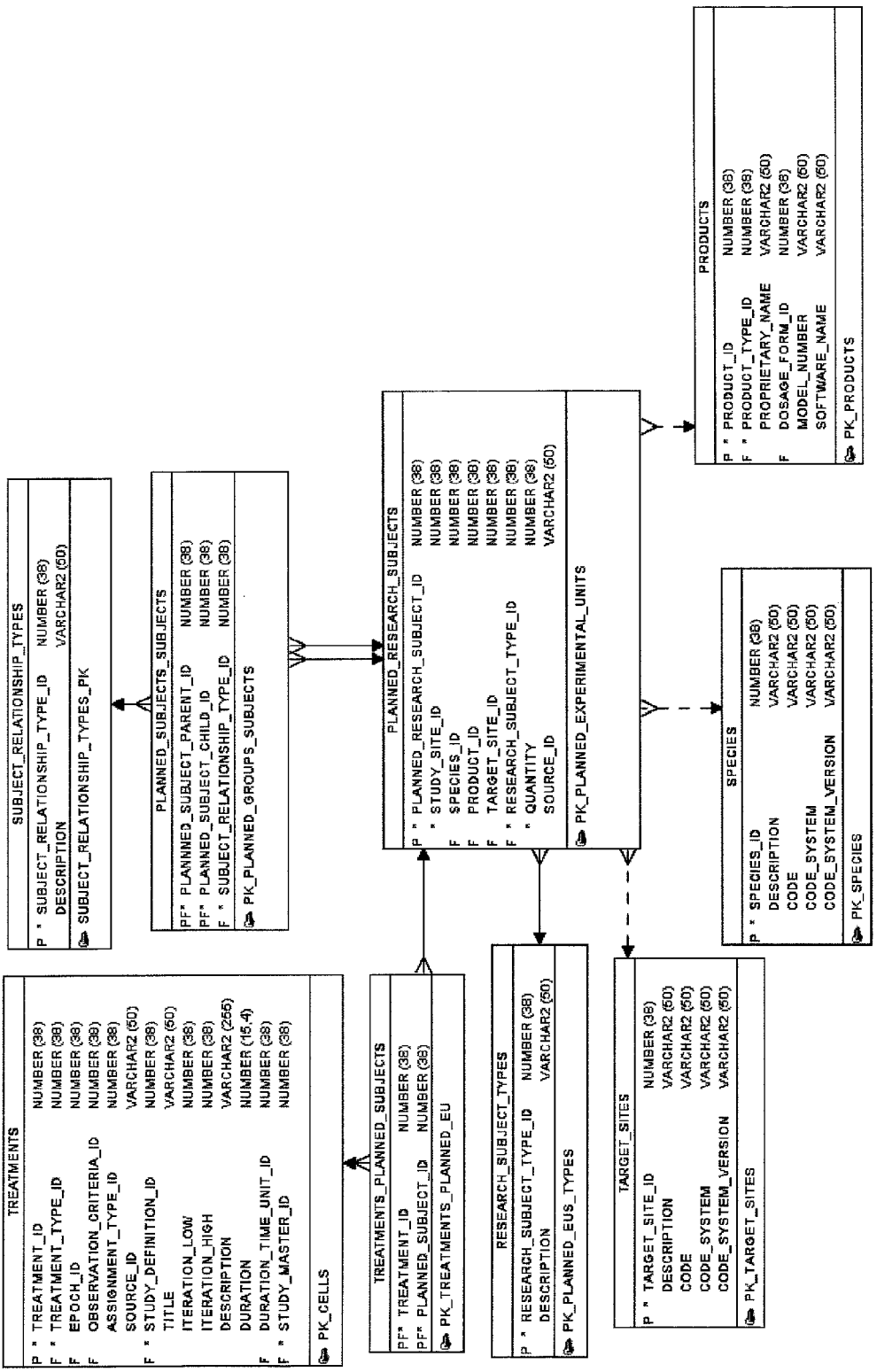
Figure 10a: Planned Research Subject

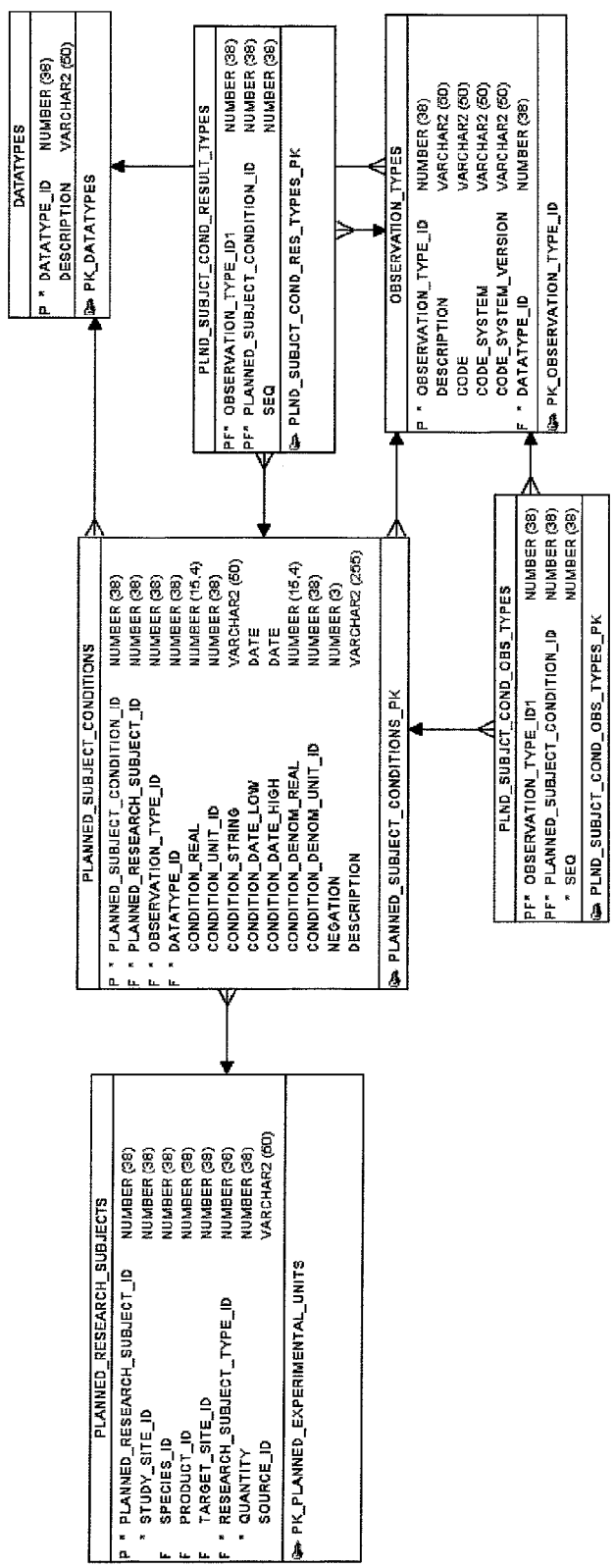
Figure 10b: Planned Research Subject

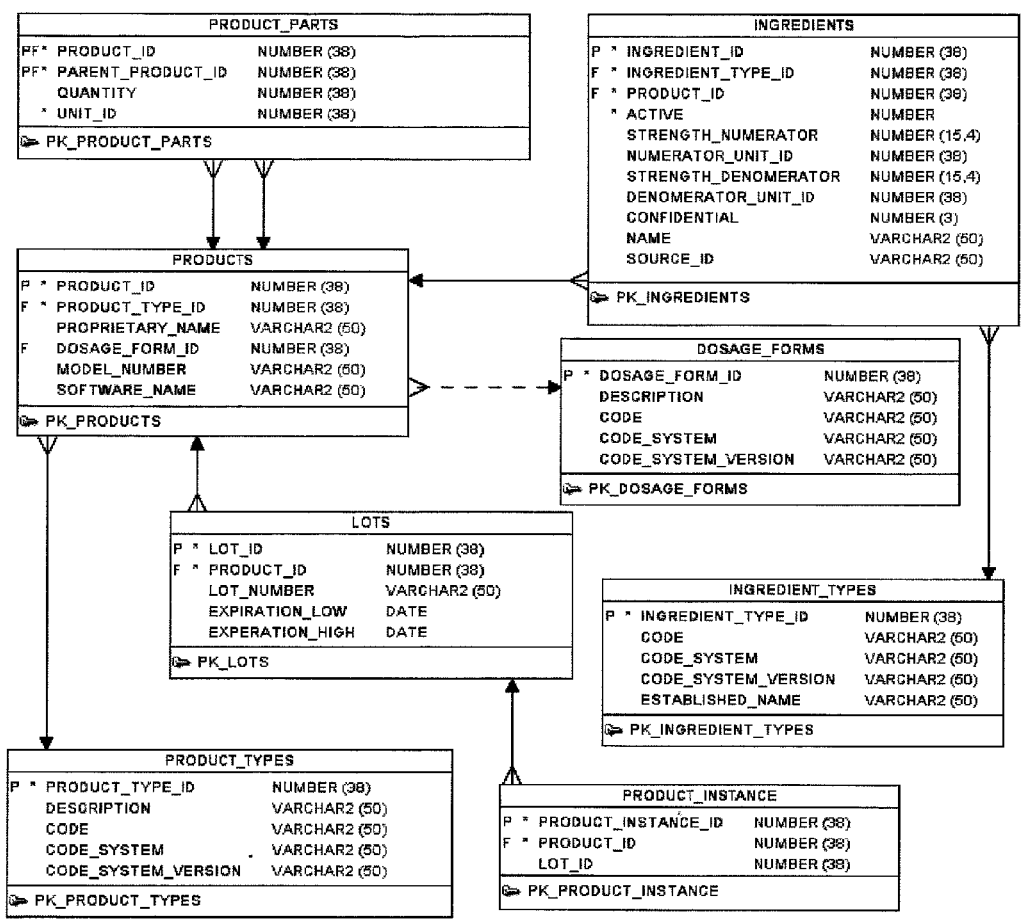
Figure 11: Product

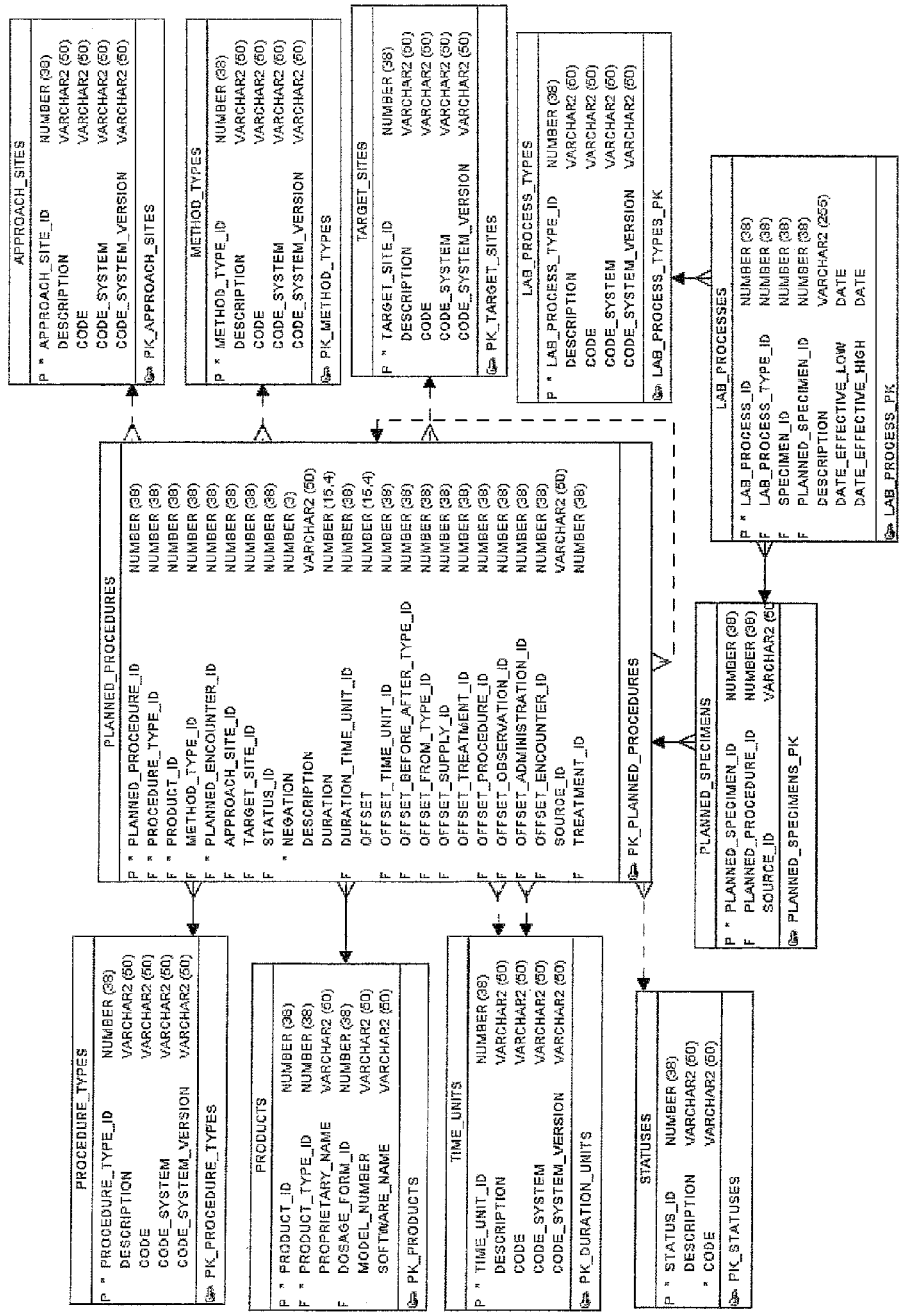
Figure 12: Planned Procedures

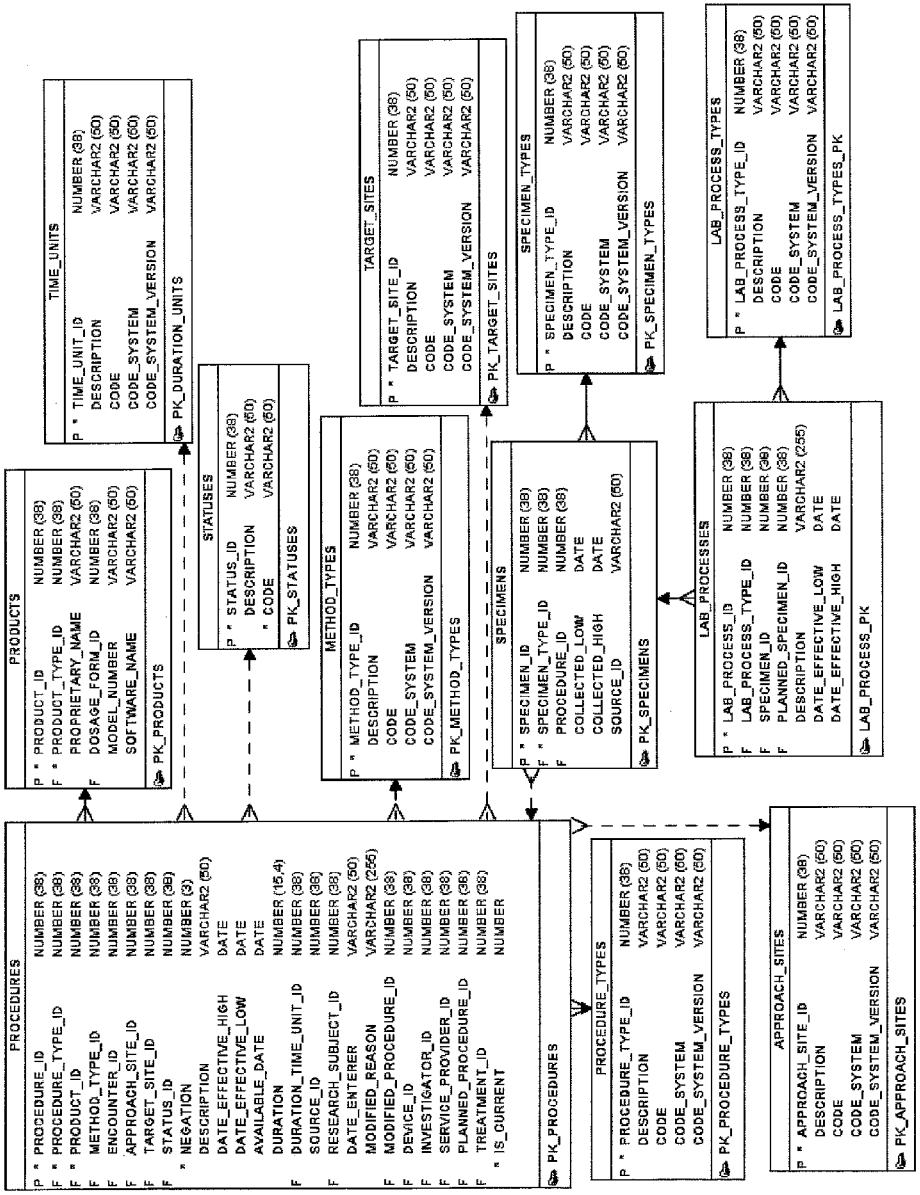
Figure 13: Procedures

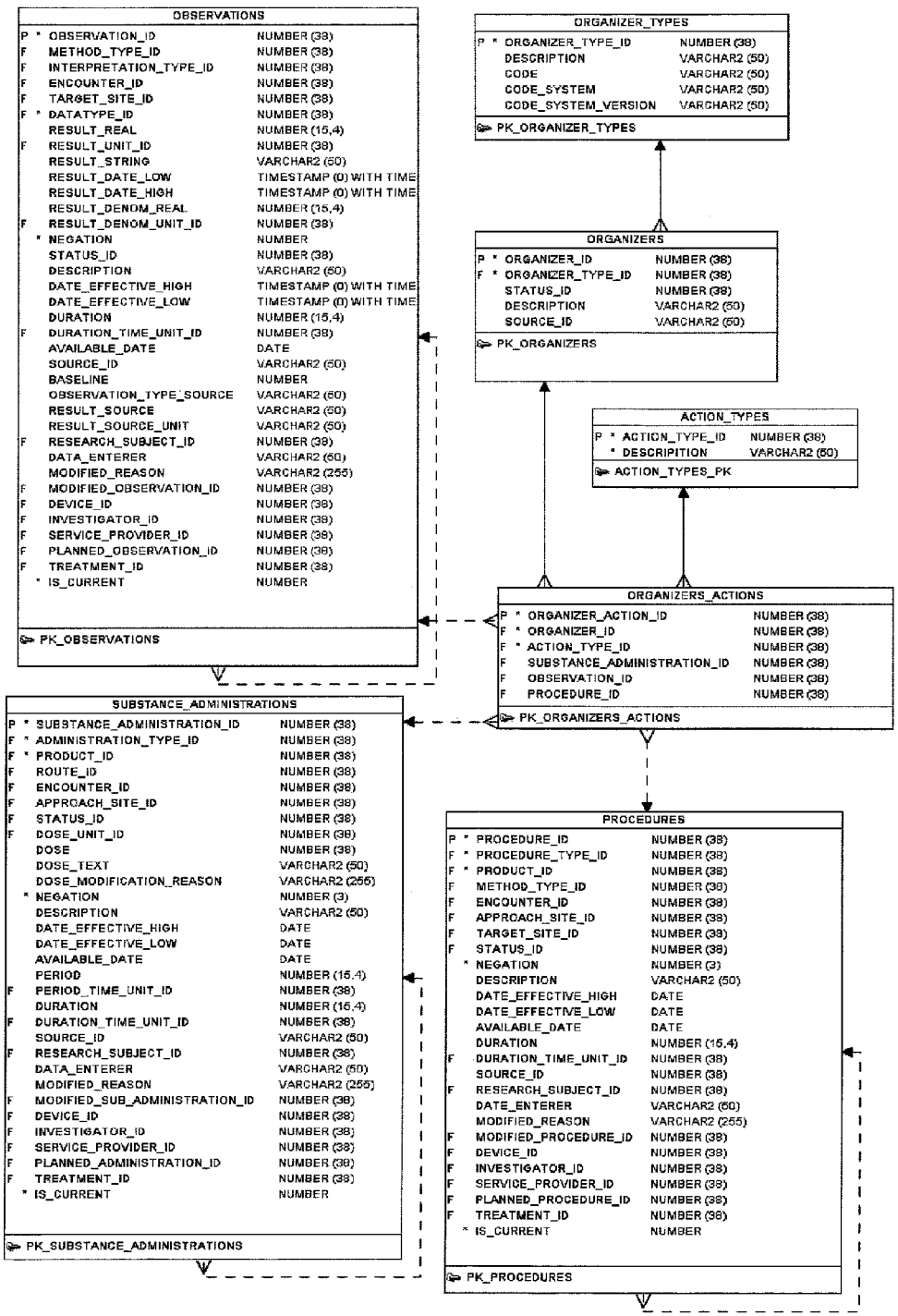
Figure 14: Organizers

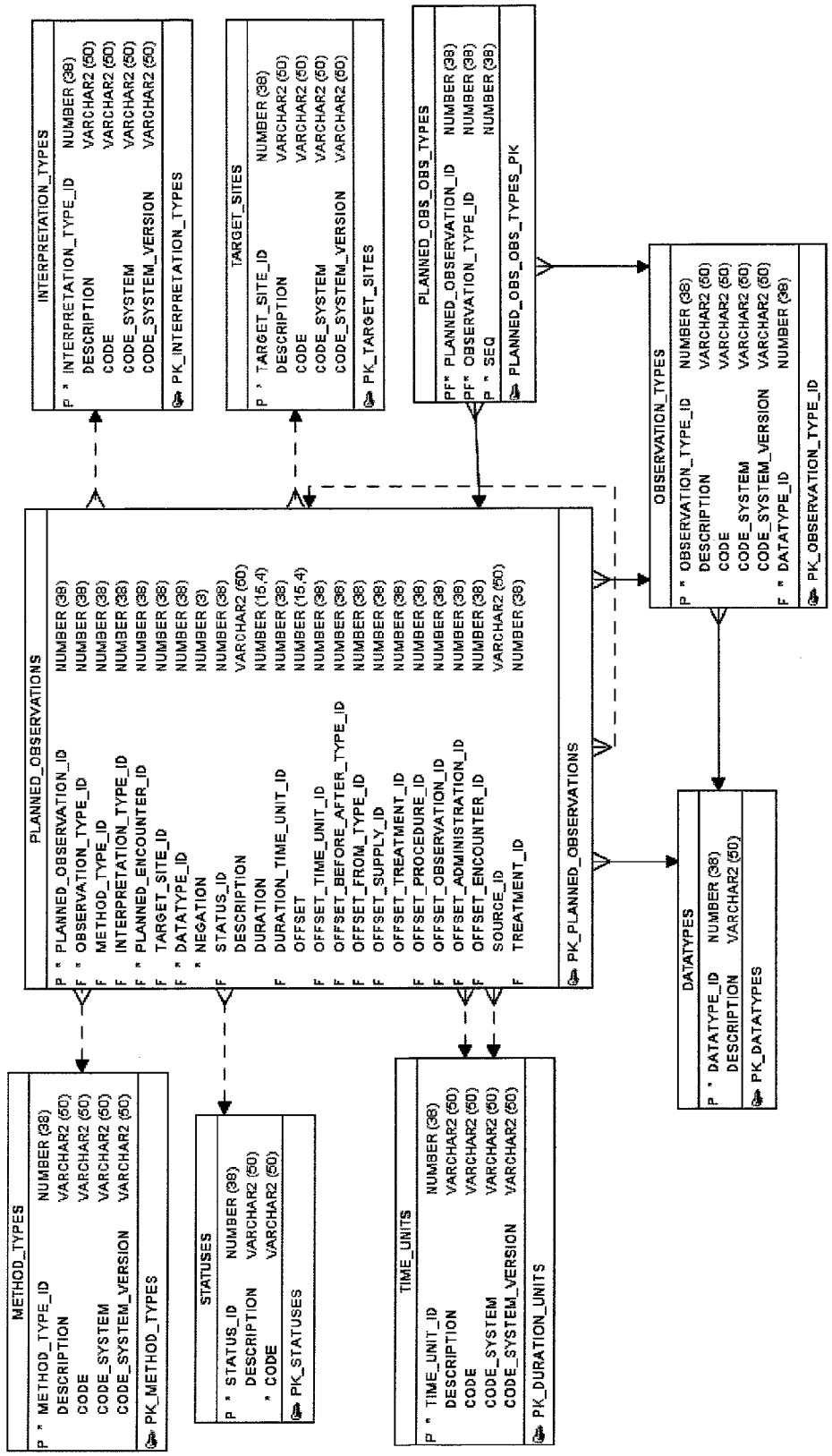
Figure 15: Planned Observations

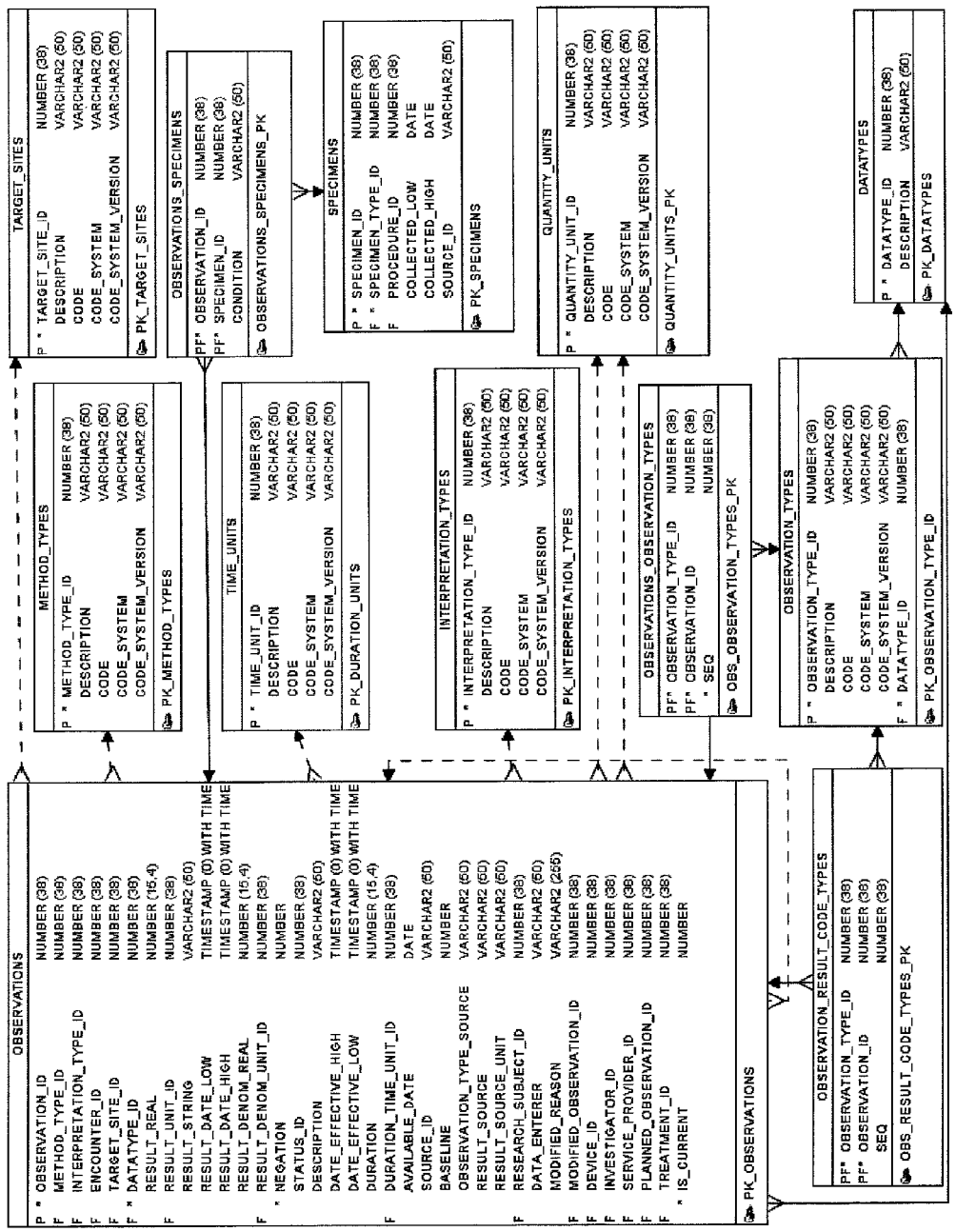
Figure 16: Observations

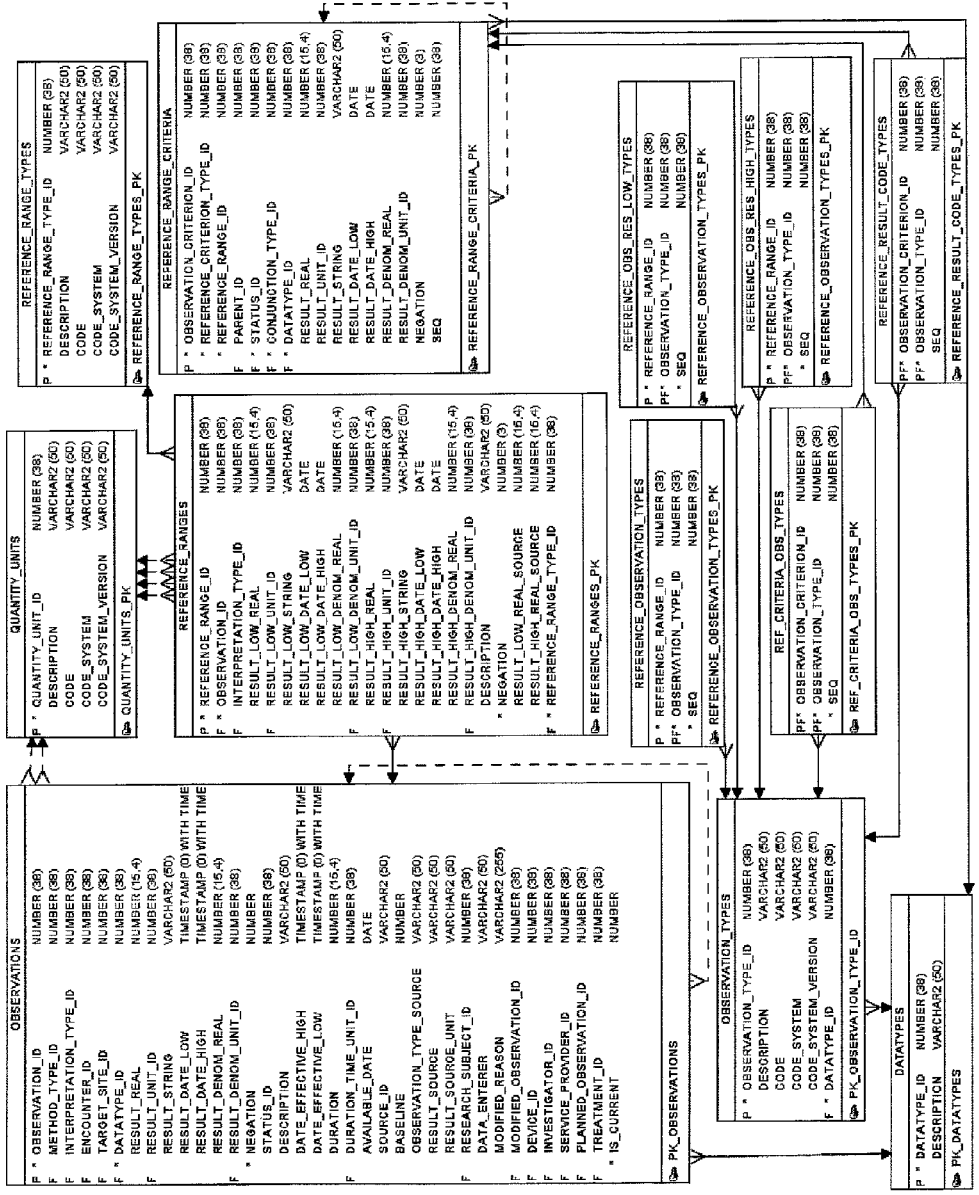
Figure 17: Reference Range

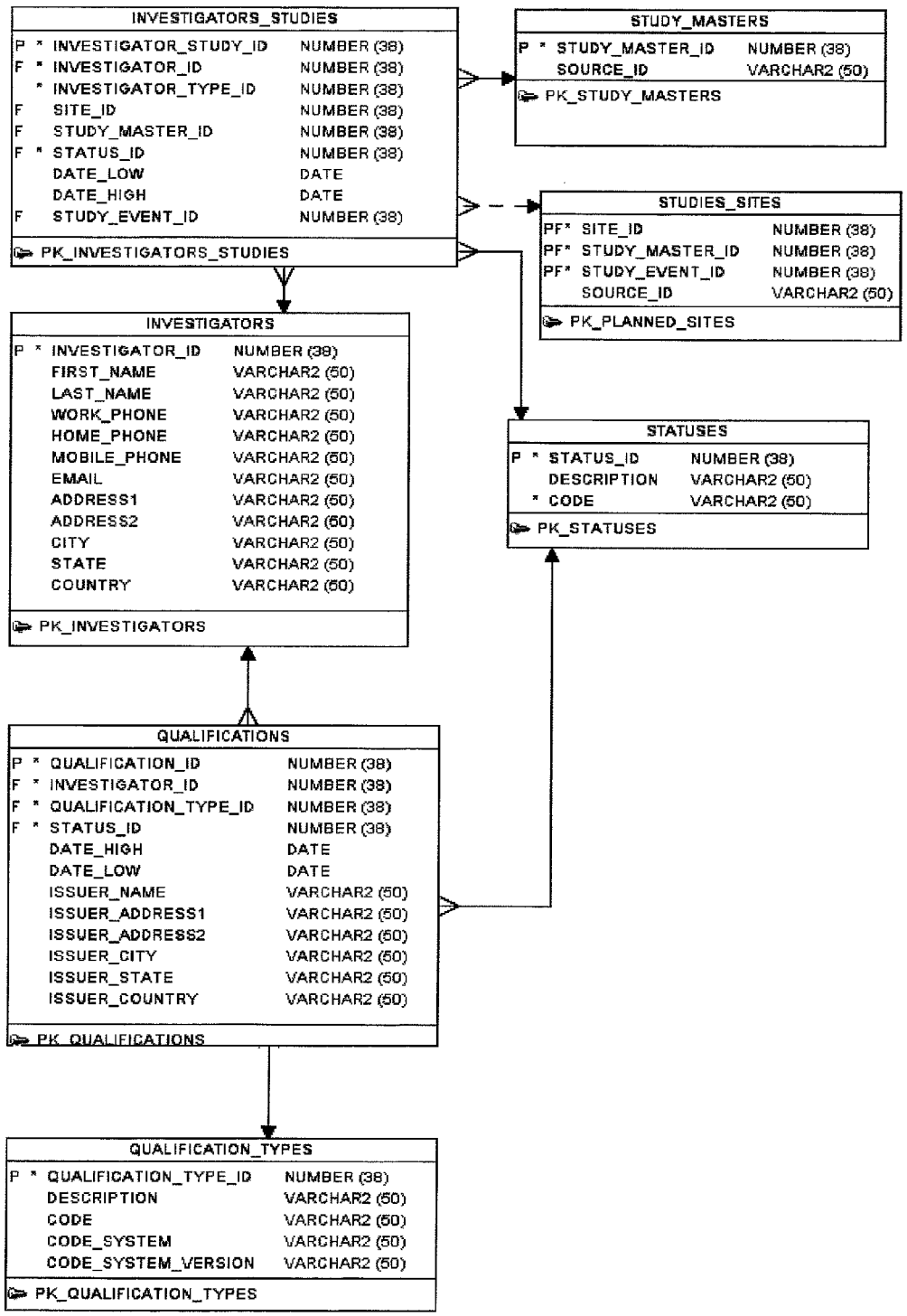
Figure 18: Investigators

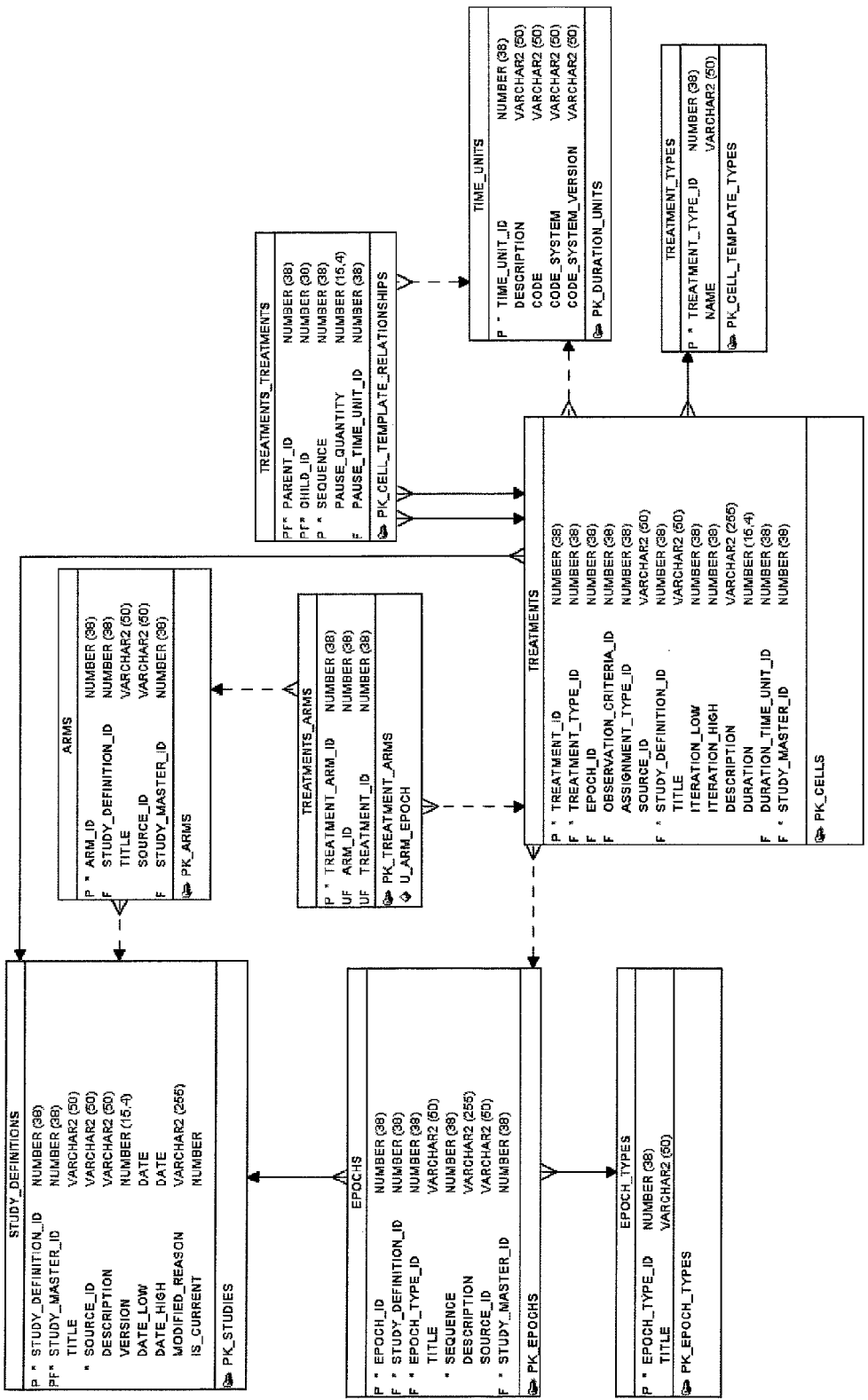
Figure 19: Study Design and Treatments

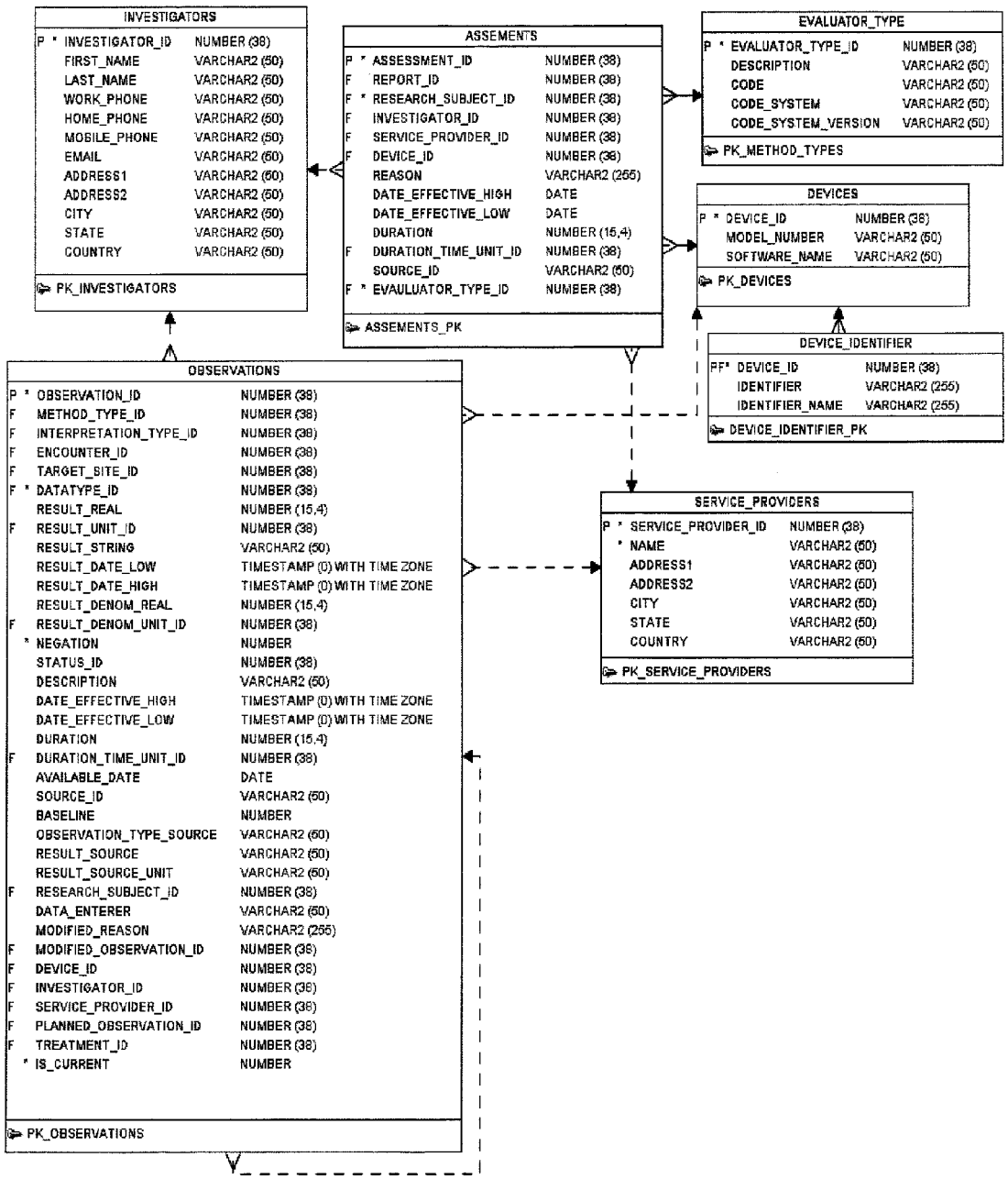
Figure 20: Evaluations

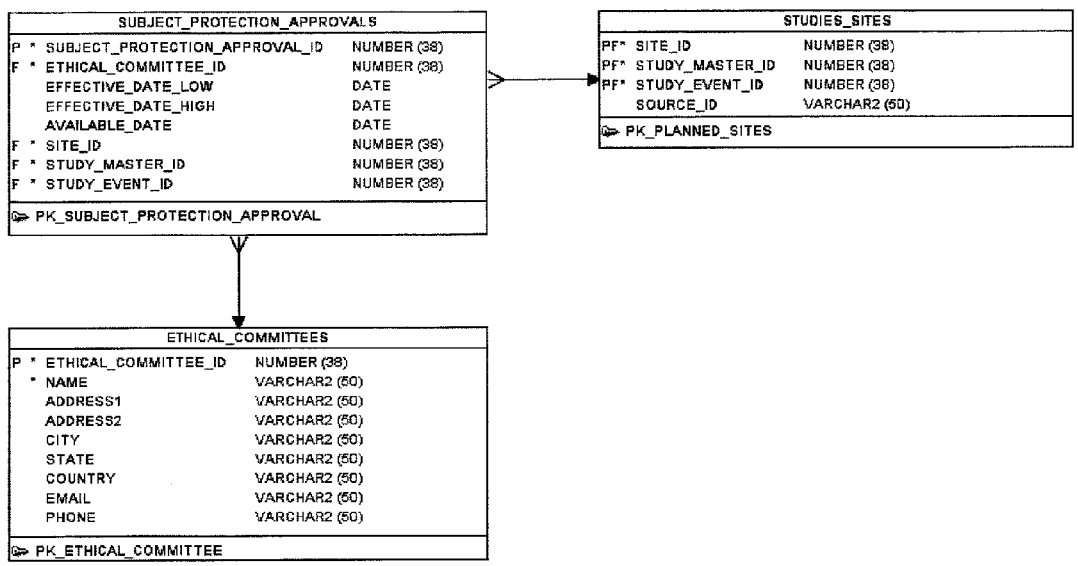
Figure 21: Ethical Committees (IRB)

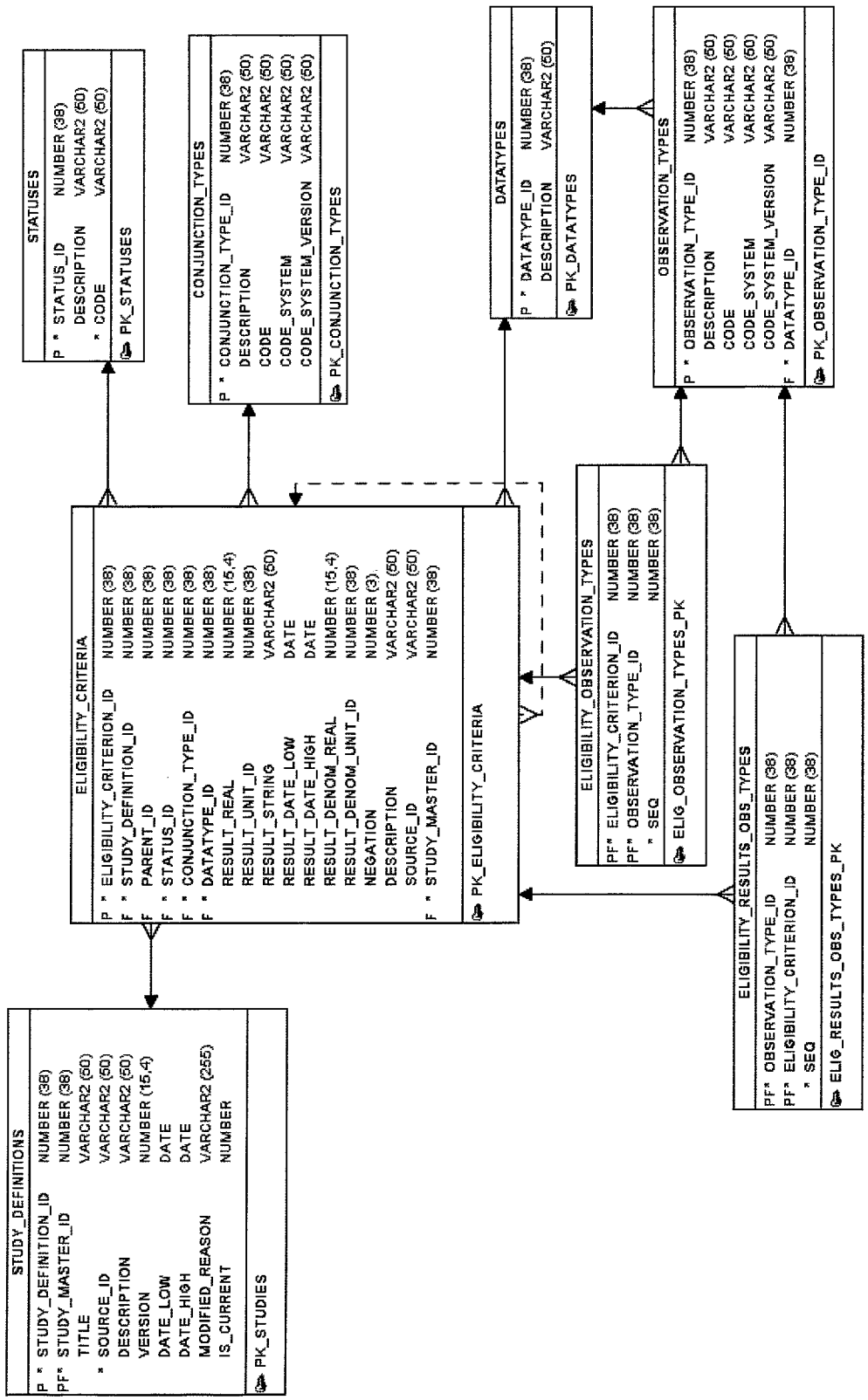
Figure 22: Eligibility Criteria

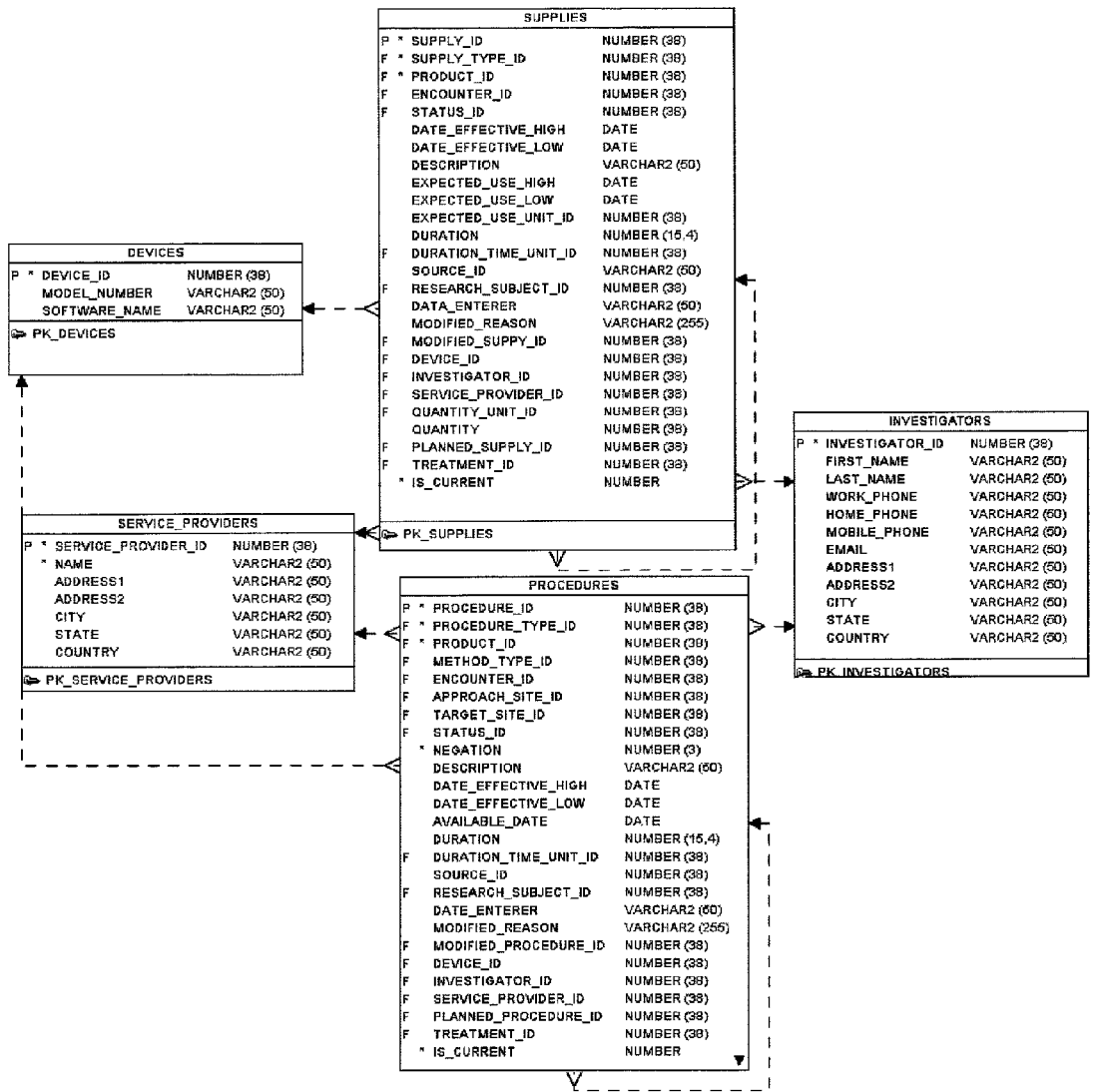
Figure 23a: Audit

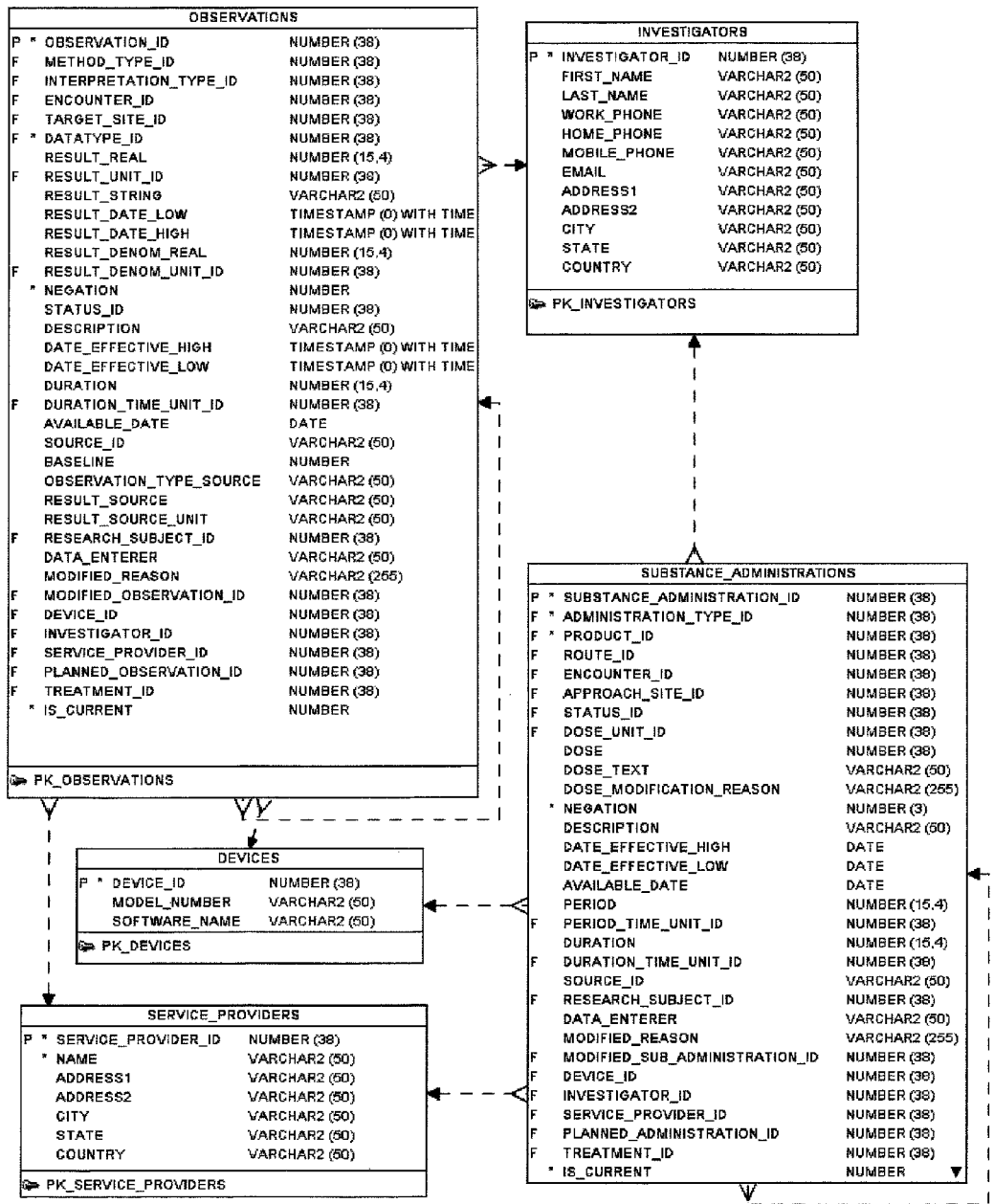
Figure 23b: Audit

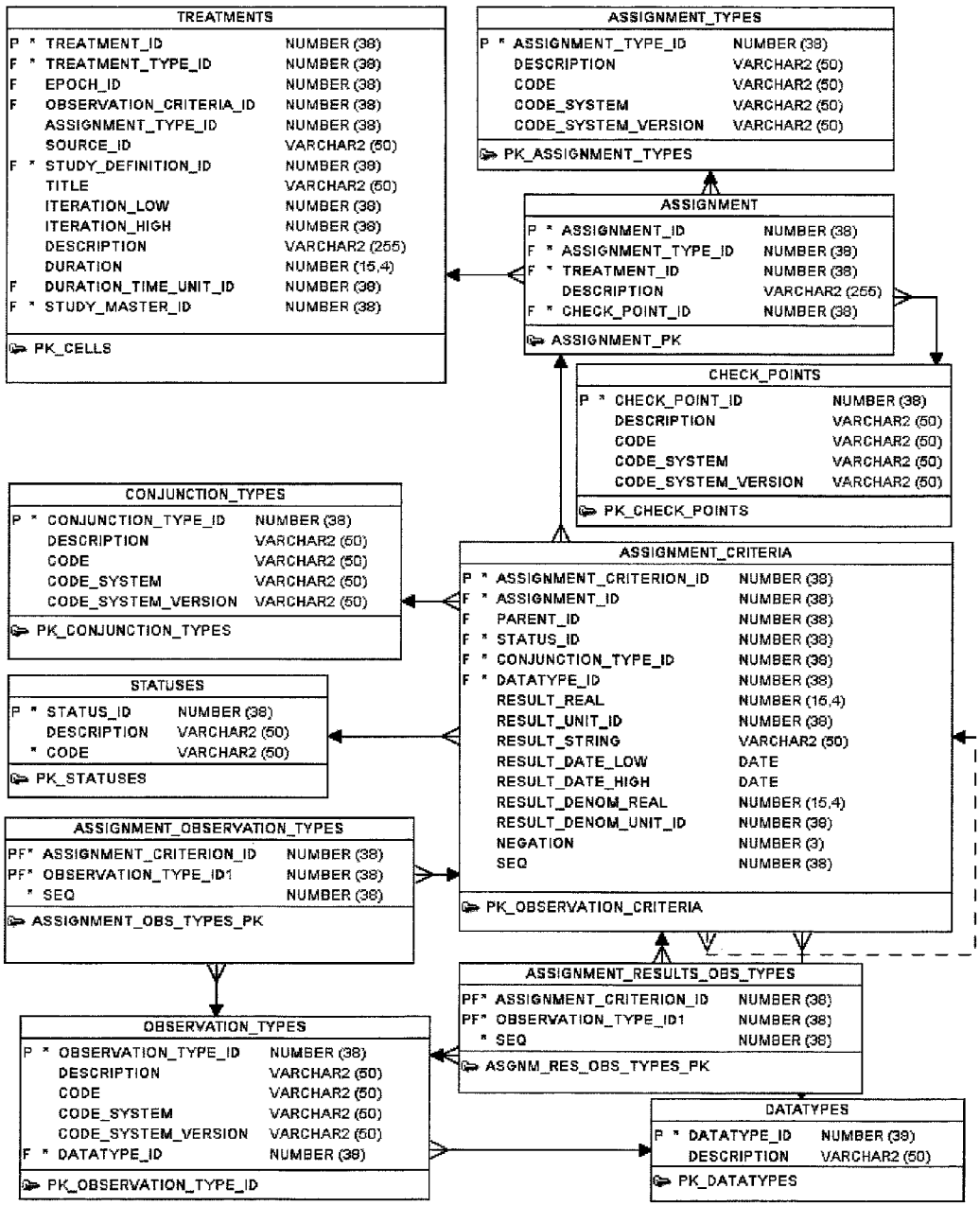
Figure 24: Assignment to Treatments

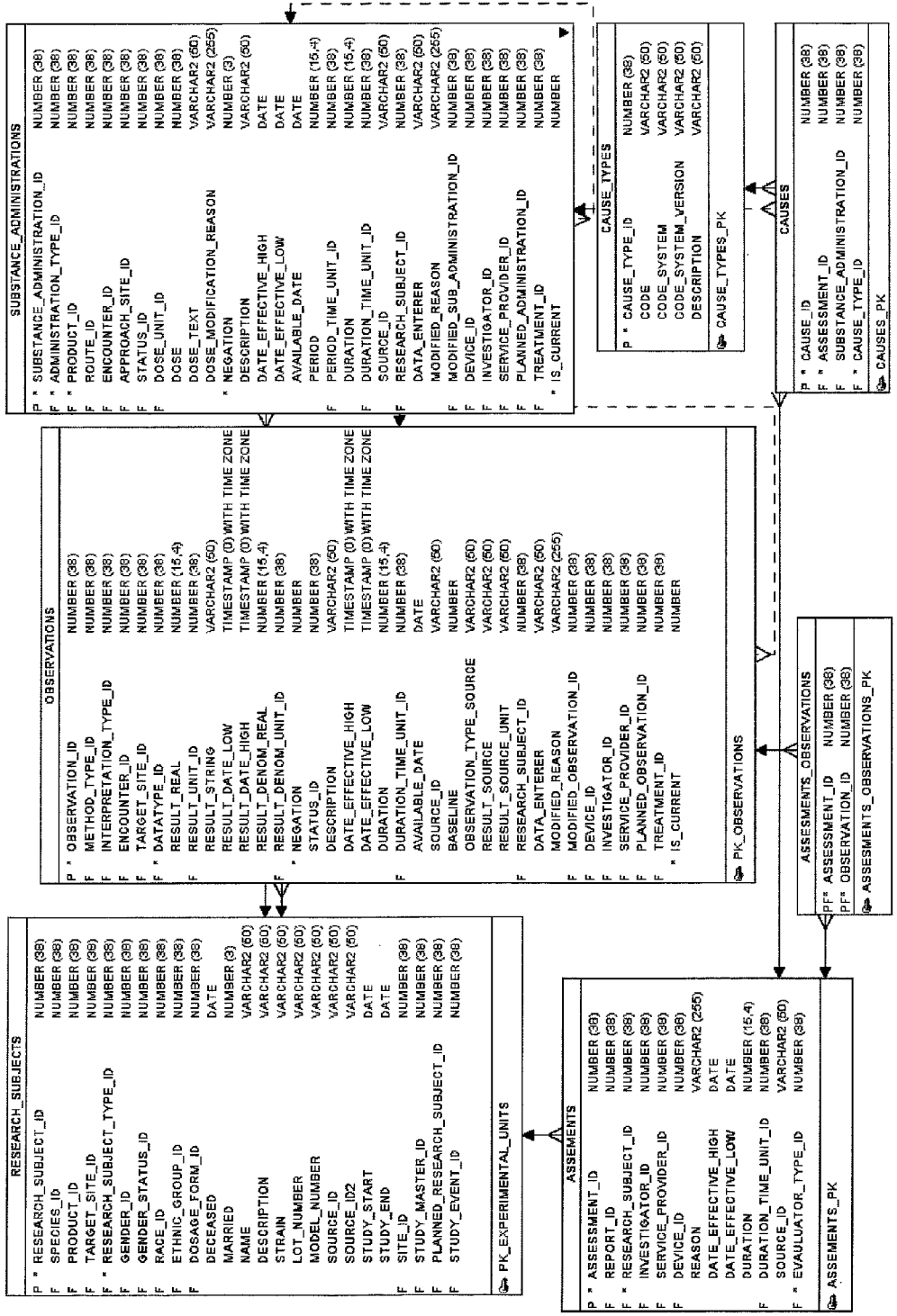
Figure 25a: Assessments on Observations (Adverse Events)

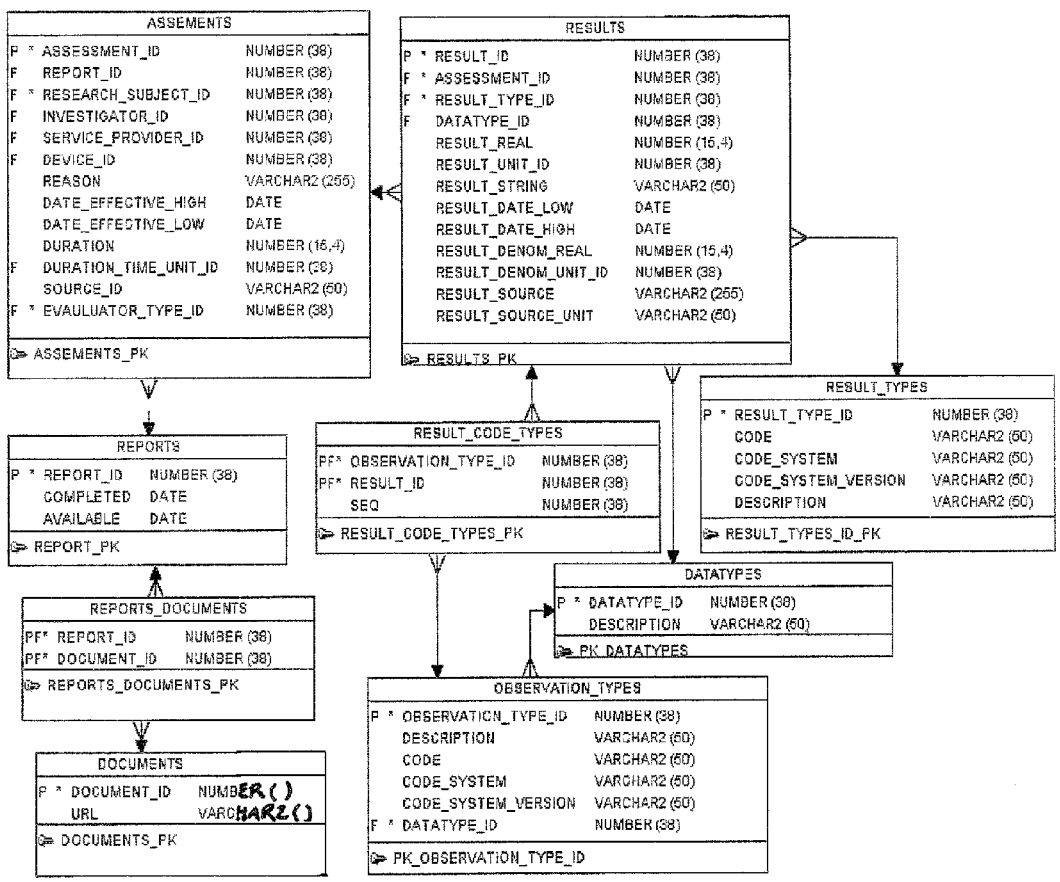
Figure 25b: Assessments on Observations

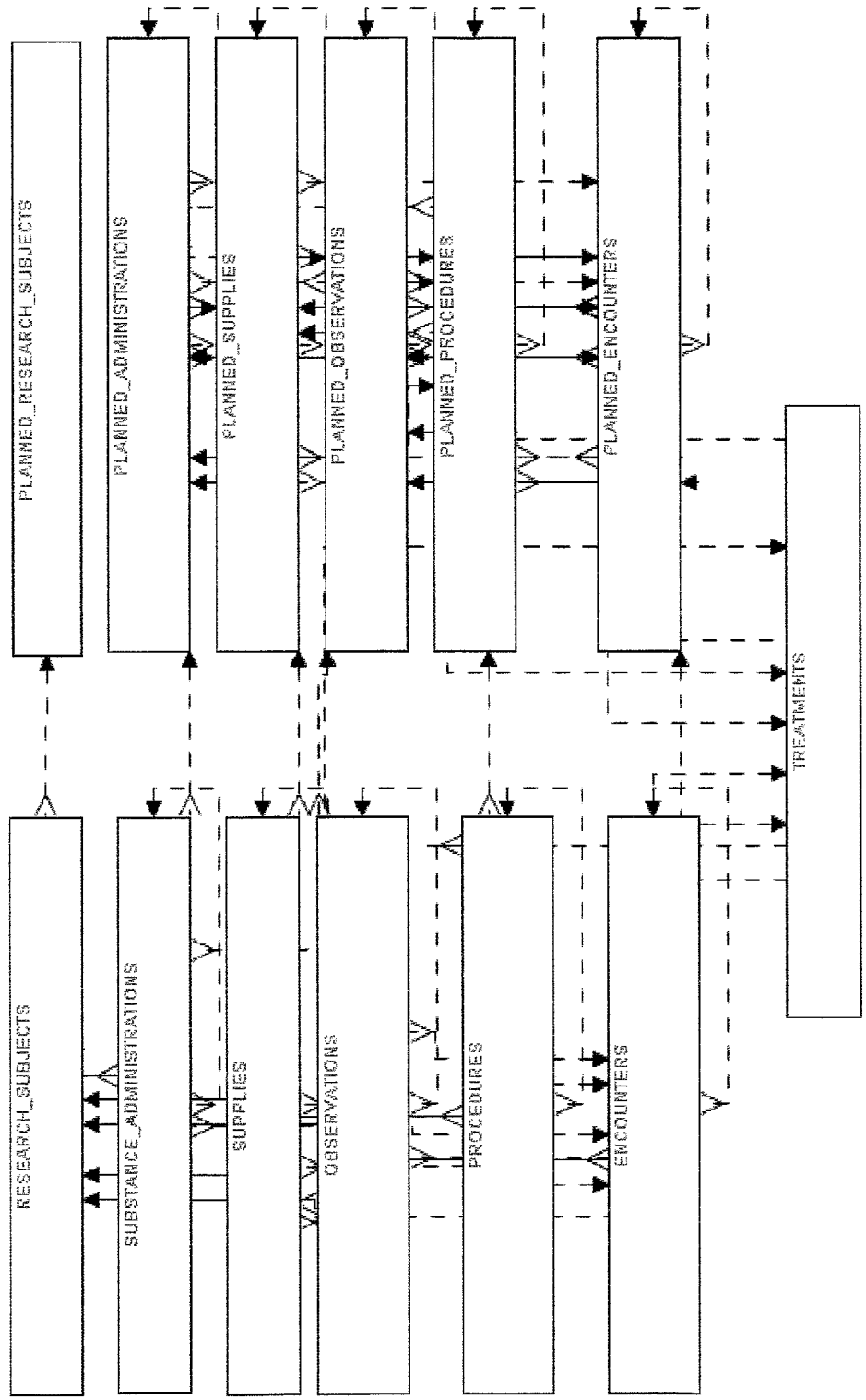
Figure 26: Comparing Actual to Planned Activities

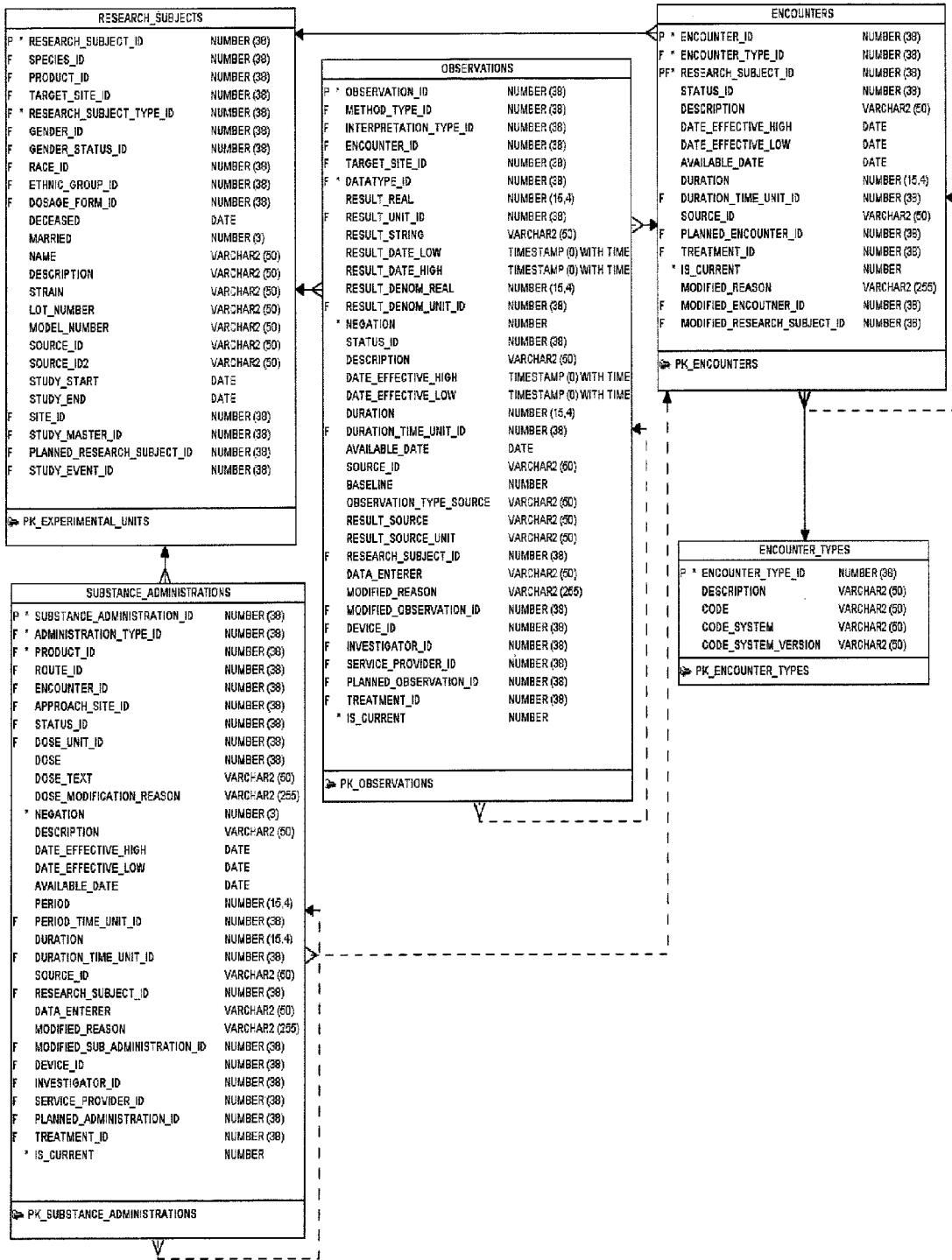
Figure 27a: Research Subject Activities

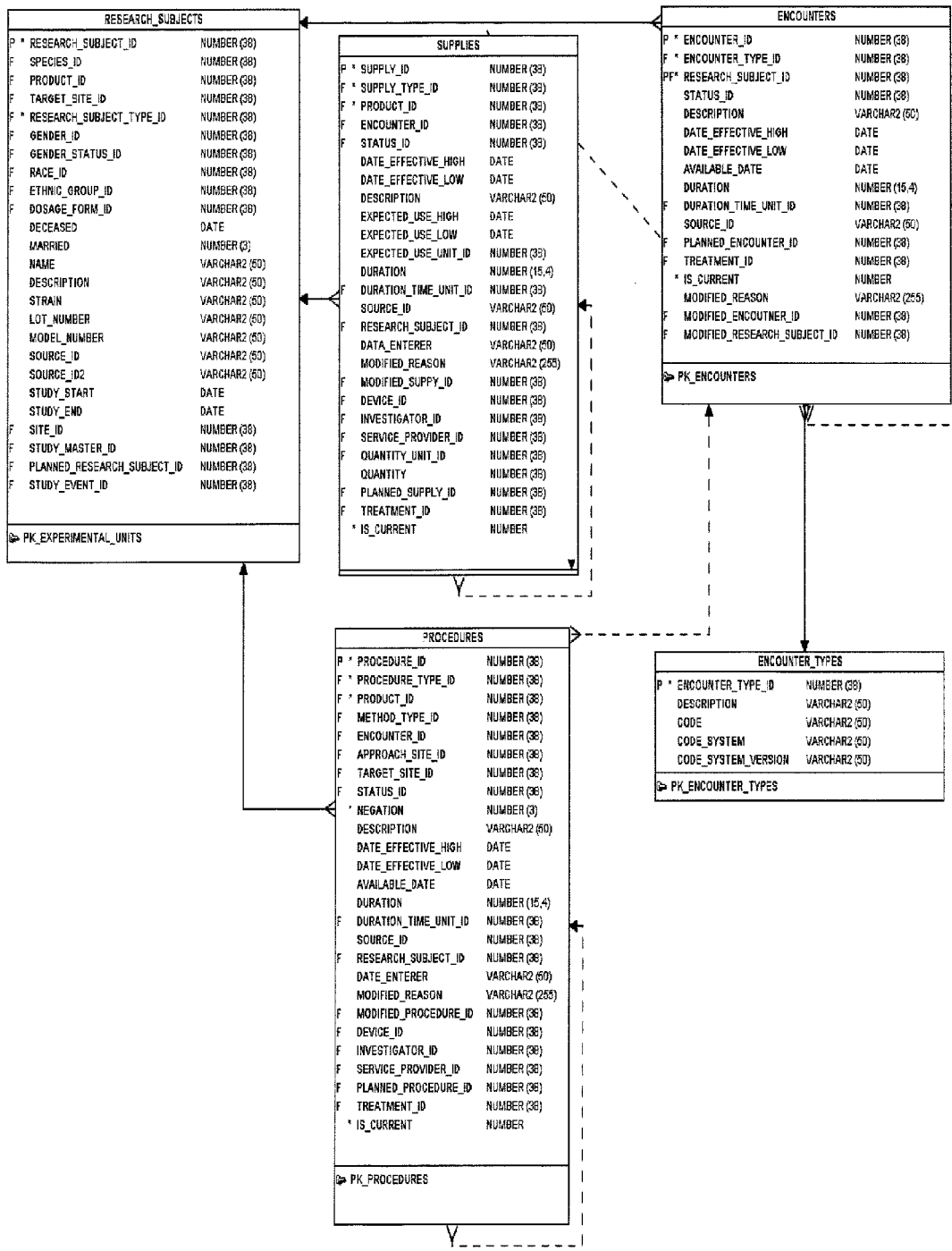
Figure 27b: Research Subject Activities

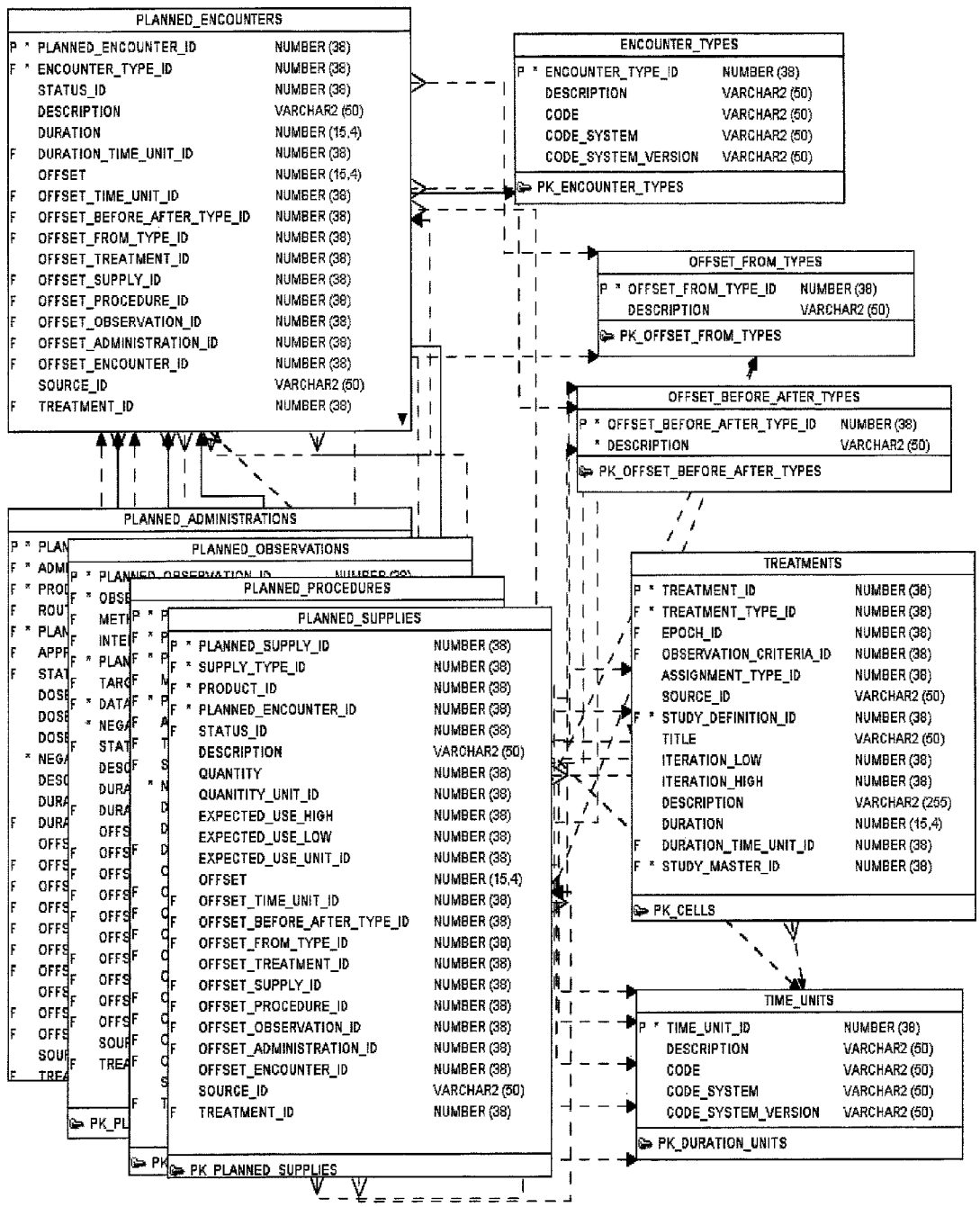
Figure 28: Planned Activities in a Treatment

RESEARCH STUDY DATABASE TO COMPARE DIFFERENT RESEARCH STUDIES AND TO COMPARE ACTUAL ACTIVITIES COMPARED TO THE PROTOCOL

CROSS-REFERENCE TO RELATED APPLICATION

This application claims the benefit of U.S. Provisional Patent Application No. 61/377,236 filed Aug. 26, 2010, which is incorporated in its entirety herein.

BACKGROUND OF THE INVENTION

The life of a drug-related patent is normally 20 years from its filing date. However, the drug development process takes around 12-15 years. Thus, the average effective patent life for a new drug—the amount of time where the product is sold under patent protection—is roughly 10 to 12 years. The Drug Price Competition and Patent Term Restoration Act of 1984, also referred to as the "Hatch-Waxman Act," allows the life of a drug product to be extended to compensate for the delay in obtaining U.S. Food and Drug Administration (FDA) approval, but the extension is limited to five years.

In addition to the direct costs of development, firms must pay returns on the capital that they invest on behalf of shareholders over the course of a decade or more, a cost that increases as development timeframes increase (Masia, Neil. "The Cost of Developing a New Drug." U.S. DEPARTMENT OF STATE Bureau of International Information Programs, Focus on Intellectual Property Rights, 2006. 82-83).

A report by the Federal Trade Commission has identified the cost of developing a new drug at five million to two billion dollars, with vaccines costing even more (Presentation, Adams, Christopher, Federal Trade Commission. "Spending on New Drug Development", Jan. 26, 2008, http://www.i-dei.fr/doc/conf/pha/conf_2008/adams.ppt, retrieved on 1 Apr. 2009). Independently, the Tufts Center for the Study of Drug Development estimates the cost to develop biologic products at $1.2 billion ("Cost to develop new biotech products is estimated to average $1.2 billion", Tufts Center for the Study of Drug Development Impact Report, Kaitin K I, editor. 2006 November/December; 8(6)). (In the U.S., a biological product is defined as "a virus, therapeutic serum, toxin, anti-toxin, vaccine, blood, blood component or derivative, allergenic product . . . , applicable to the prevention, treatment or cure of a disease or condition of human beings" (Public Health Services Act 42 U.S.C. §262(i)).)

FIG. 29 shows the significant components of the drug development process. After a promising compound has been identified during the process of drug discovery, the development phase begins with the nonclinical phase (animal studies), with goals of determining a compound's probability of success, understanding its potential adverse effects in humans, and determining dosing amounts and delivery methods that will allow safe testing in humans.

After sufficient data has been gathered, a drug company submits an Investigational New Drug Application (IND) to the FDA, providing data showing that it is reasonable to begin tests of a new drug on humans New information is provided to the FDA every month until the drug is approved. New information submitted to the FDA is called a "submission." There could be over 500 submissions for an IND application. For cancer drugs, on average it takes 8 years from the start of clinical trials (human testing) to approval to market the product.

The Clinical phase of drug development is intended to prove that the drug is safe and effective for its proposed use. If there are existing drugs on the market that are for the same purpose as the investigational new drug, the investigational new drug must provide evidence that it is superior to the already approved drug. For both safety and economic reasons, clinical development takes place over several phases:

Phase 1: Involves the initial introduction of an investigational new drug into humans. These studies are closely monitored and may be conducted in patients, but are usually conducted in healthy volunteer subjects. These studies are designed to determine the initial effect, risks, and, if possible, to gain early evidence on effectiveness. The total number of subjects included in Phase 1 studies varies with the drug, but is generally in the range of 20 to 80.

Phase 2: Studies are conducted to obtain some preliminary data on the effectiveness of the drug for a particular purpose (indication) with patients who have the disease or condition. This phase of testing also helps determine the common short-term side effects associated with the drug. Phase 2 studies are typically well-controlled, closely monitored, and conducted in a relatively small number of patients, usually involving several hundred people.

Phase 3: Studies are expanded controlled and uncontrolled trials. They are performed after preliminary evidence suggesting effectiveness of the drug has been obtained in Phase 2, and are intended to gather the additional information about effectiveness and safety that is needed to evaluate the overall benefit-risk relationship of the drug. Phase 3 studies also provide an adequate basis for extrapolating the results to the general population and transmitting that information in the physician labeling. Phase 3 studies usually include several hundred to several thousand people.

There could be anywhere from several hundred to fewer than one thousand studies performed to show that a product is safe and effective with over a million data points. Each study stores the data points differently, thereby making it extremely difficult to perform analysis across studies and across products. Each study can potentially be run by a different organization and can store and collect data differently.

A clinical trial protocol (protocol) is a document that describes the objective(s), design, methodology, statistical considerations, and organization of a clinical trial. The protocol contains a study plan on which the clinical trial is based. The protocol describes what types of people may participate in the trial; the schedule of tests, procedures, medications, and dosages; and the length of the study. When analyzing the clinical study data, it can be very difficult and time-consuming to quickly and accurately determine if the protocol was properly followed. The protocol is also referred to herein as the "study definition."

RELATED PRIOR ART

1. Janus 1

The present invention is based on the goals of the FDA Janus study data repository, described, in part, at the following FDA webpage: http://www.fda.gov/ForIndustry/Data-Standards/StudyDataStandards/ucm155327.htm (all of the above, accessed on Aug. 13, 2010)

The Janus study data repository is being developed by FDA and the National Cancer Institute (NCI) through an Interagency Oncology Task Force (IOTF) that was established in 2003 to enable the two organizations to share knowledge and resources to facilitate the development of new cancer drugs and speed their delivery to patients. As part of the IOTF agreement, FDA is working with NCI to build tools and an environment that facilitates and streamlines electronic interaction and collaboration among FDA and its stakeholders in the regulatory review process. The Janus data repository is part of a larger effort to implement a common, standards-based electronic infrastructure that supports the submission, validation, data warehousing, access, and analysis of clinical and non-clinical study data. SDTM is the standard for the submission of data to the Janus repository.

Phase 1 of the Janus/CRIX project, which included requirements gathering, creation of a prototype environment, and implementation of the Janus module as a proof of concept in the caBIG environment, was completed on Jan. 26, 2006. Phase 2 involved the implementation of an operational pilot that integrated two reviewer tools with the Janus repository. Phase 2 activities (actual activities) included development of a data validation and import facility, loading of validated SDTM datasets into the Janus repository, and creation of analytical views that could be accessed with reviewer analytical and visualization tools.

2. CDISC Study Data Tabulation Model (SDTM)

Study Data Tabulation Model (SDTM, available at http://www.cdisc.org/standards) describes the general conceptual model for representing clinical study data that is submitted to regulatory authorities and the SDTMIG provides specific domain models, assumptions, business rules, and examples for preparing standard tabulation datasets that are based on the SDTM. Domains are tabular listings of information in a study.

3. HL7 Reference Information Model (RIM)

The RIM provides a static view of the information needs of HL7 V3 standards. It includes class and state-machine diagrams and is accompanied by use case models, interaction models, data type models, terminology models, and other types of models to provide a complete view of the requirements and design of HL7 standards. The classes, attributes, state-machines, and relationships in the RIM are used to derive domain-specific information models that are then transformed through a series of constraining refinement processes to eventually yield a static model of the information content of an HL7 standard.

BRIEF SUMMARY OF THE INVENTION

Currently, the FDA and drug development industry spends 30-80% of their time reformatting data to perform analysis. So much time is spent on reformatting the data because each study stores the data differently and there is no a good way to put the data in a common format. The present invention provides a database schema for housing research studies that support research human therapies, veterinary medicine, medical devices and food supplements. The database schema allows for a single database that will house many studies and allow those studies to be analyzed quickly and efficiently. The database allows for comparison studies across different products and the same product. Since data is stored in a uniform manner, the amount of data reformatting is dramatically reduced. The ability to create reusable programs to do certain analysis is possible since the data is stored in a uniformed manner. The database also allows for analysis that compares the protocol to what actually occurred.

DIFFERENCES BETWEEN EMBODIMENTS OF THE PRESENT INVENTION AND THE PRIOR ART

Both Janus 1 and SDTM have a generic method to relate multiple actions. The generic method is to create a group of actions. The group of actions does not have any context, it is just a group. Embodiments of the present invention allows many actions to be related in a meaningful way. A set of observations can be specified to make up an adverse event (which is an actual activity) and the interventions (e.g. substance administrations, procedures) that are the cause can be specified. Both Janus 1 and SDTM do not have a strong link from what actually occurred to what was planned. Janus 1 falls short since there is no direct link to the planned event and SDTM falls short since detail plans (i.e., the schedule of actual activities) are not documented. Neither Janus 1 nor SDTM handle different types of data effectively. Since most data are stored as text, it is hard to compare values. For example, it is hard for a system to determine if the text "two" is greater than the text "1." Furthermore, it is unclear if "two" is a number. Also, Janus 1 and SDTM do not capture service providers and detailed information about the investigator and ethical committees. Janus 1 does not handle research subjects that are not about a human as a whole.

Since neither Janus 1 nor SDTM can relate to the planned study (i.e., study design and schedule of actual activities) it is impossible to compare what actually occurred in the study to what is planned. Since Janus 1 and SDTM do not uniformly store data, one cannot make observational correlations to determine what therapies work best. Embodiments of the present invention can pull data from multiple studies in a uniform manner that will allow one to make observational correlations to determine what therapies work best.

The HL7's RIM is a generic structure that can be used for healthcare communications. The RIM does not specify any one use and does not specify storage. Accordingly, the RIM cannot be directly used for a specific purpose like the storage and retrieval of clinical data. The RIM is used as a basis for communicated healthcare information.

BRIEF DESCRIPTION OF THE DRAWINGS

Some embodiments of the present invention will now be described by way of example with reference to the accompanying drawings:

FIG. 1: Supplies Entity Relationship Diagram (ERD): How much and when a product is supplied to the research subject.

FIG. 2: Planned Supplies ERD: How much and when a product is planned to be supplied to the research subject. A planned activity can be an elapsed time from another planned activity or treatment.

FIG. 3: Summaries of the Study ERD: Basic characteristics of the study like the blinding or the patient population.

FIG. 4: Planned Substance Administration ERD: The dose, product, route and location of where the substance is planned to be administered and when it will be administered. A planned activity can be an elapsed time from another planned activity or treatment.

FIG. 5: Substance Administration ERD: The dose, product, route and location of where the substance has been administered and when it was administered.

FIG. 6: Study Amendments ERD: All different version of the study including the original and amendments.

FIG. 7: Sites and Service Location ERD: The location of the site and where actual activities are performed, including where the sites are planned to be located or the number of sites planned.

FIG. 8: Service Provider ERD: All of the organization that provide services, their physical locations and sites they are associated with.

FIGS. 9a and 9b: The subject of the research ERD: The subject could be human, living subject that is not a human, a product, a group, or a part/specimen.

FIGS. 10a and 10b: ERD shows the planned research subject including the amount of the research subjects and the actual activities that will be performed.

FIG. 11: Product ERD: Product can have parts, be in a lot, have a dose form, ingredients and with the lots there could have a product instance.

FIG. 12: Planned Procedures ERD: When a procedure is planned to take place, the product plan to be used in the procedure, the specimen planned to be collected, the process to collect the specimen, where the procedure will occur, the method of the procedure. A planned activity can be an elapsed time from another planned activity or treatment.

FIG. 13: Procedures ERD: When a procedure is take place, the product used in the procedure, the specimen collected, the process to collect the specimen, where the procedure occurred, the method of the procedure.

FIG. 14: Organizers ERD: Organizes planned activities or actual activities for analysis and other purposes.

FIG. 15: Planned Observations ERD: When an observation is planned, the method of the observation and where on the subject the observation is planned. A planned activity can be an elapsed time from another planned activity or treatment.

FIG. 16: Observations ERD: When an observation occurred, the method of the observation and where on the subject the observation occurred.

FIG. 17: Reference Range ERD: The range of valid values of the observation from the lab or standard for this observation.

FIG. 18: Investigators ERD: The name and address of the investigator, their qualifications and which study sites they are associated with.

FIG. 19: Study Design and Treatments ERD: The experimental design and schedule of planned activities.

FIG. 20: Evaluations ERD: An evaluation made by a service provider, investigators or device.

FIG. 21: Ethical Committees (IRB) ERD: The ethical committee name and address that approves the study at a site for certain time period and granted at a specific date.

FIG. 22: Eligibility Criteria ERD: The eligibility criteria for a study and how the criteria relate to each other.

FIGS. 23a and 23b: Audit ERD: All actual activities that are performed by the investigator or device.

FIG. 24: Assignment to Treatments ERD: The criteria used and when to check to assign a subject to a treatment.

FIGS. 25a and 25b: Assessments on Observations (Adverse Events) ERD: An assessment or a report of assessments for a subject about observations, causes and results of the assessment, including when the report was completed and available.

FIG. 26: Comparing Actual to Planned Activities ERD: Linking what actually occurred to the planned activity or planned treatment.

FIGS. 27a and 27b: Research Subject and Actual Activities ERD: All actual activities that occur for a research subject, where they occur, when, the duration and when the information was made available.

FIG. 28: Planned Activities in a Treatment ERD: All of the planned activities, including timing, in a specified treatment strategy.

FIG. 29 shows the significant components of the drug development process.

FIG. 30 shows a hardware configuration diagram in accordance with one embodiment of the present invention.

FIG. 31 shows a Process Overview flow diagram of the entire process that is performed by one embodiment of the present invention.

In the figures, the symbol "P" refers to "Primary Key" and the symbol "F" refers to "Foreign Key."

DETAILED DESCRIPTION OF THE INVENTION

Certain terminology is used herein for convenience only and is not to be taken as a limitation on the present invention. For the purposes of explaining the present invention, specific embodiments will be described. These embodiments are exemplary only, and are not intended to limit the scope of the invention.

In one embodiment, a researcher performs a study to determine if an experimental product is more effective than a placebo. An example of one workflow embodiment is shown in FIG. 31. All steps of the Process Overview are described below. The steps can be done in other order as well. In describing this embodiment, reference is made to the figures and to the tables in the figures. A detailed description of the contents of the tables in the figures is provided below.

An experimental product (FIG. 11) can be used in a study. The product (Table 68: Product) can have ingredients (Table 33: Ingredients); that is, a material (or chemical substance) in the make-up of the main product, not a structural part or content, and not a material added into a device for operation. For medicines and food this is obvious. For devices, an example for ingredient would be latex (Table 67: Product Types) in a chest tube (but not an inhalant in a nebulizer device). Devices also can be known by many identifiers (Table 16: Device Identifier). For example, the manufacturer can have an identifier or manufacturer code and another identifier could be the regulators identifier. The ingredient can be active and have a strength (e.g., 4 mg). The product can be composed of sub products (Table 66: Product Part) and can have a specified dosage form (Table 19: Dosage Form) (e.g., tablet, ointment, gel, etc).

The researcher would design an experiment (FIG. 19). The research would first define the study (Table 101: Study Definition) with a title description and the length of the study. The researcher could choose a simple parallel study that would have two arms (Table 4: Arms) for comparison, the first arm would represent the experimental product and the second arm would represent the placebo. An Arm represents a unique path (of treatments) a subject can take during a study (Table 119: Treatment Arms). Since this is a simple parallel study, there would be three epochs (Table 25: Epochs), the first sequenced epoch would be of a type of screening to ensure only qualified subjects enter the study, the second epoch would be the interventional epoch and the third epoch would be to follow up on the subjects for safety reasons. Epochs are used to compare two or more treatments. Each epoch could have a friendly title and a description. Then the researcher would define treatments (Table 118: Treatments).

A treatment could be organized into smaller parts (Table 121: Sub Treatments). For example, in a cancer study, a treatment could be broken down into a chemotherapy period (treatment) with two different radiation cycles. Since a treatment can be re-used, a treatment is associated with an Arm and Epoch. An example of when a treatment is re-used is in a balanced crossover study where the subjects in different arms receive the same treatments but in different order.

Treatments have a complex workflow (FIG. 24). Treatments have exit and entry criteria and use a workflow control suite of attributes. If there are multiple treatments with the same sequence number, the priority number determines which assignment (Table 7: Assignment) to evaluate first. Before each step, criteria assignments are tested, if applicable. To determine which criteria are applicable, a check point code (Table 13: Check Points) is used. The check point code specifies when in the rules are evaluated (e.g., before the treatment starts for the first time, before every repetition, after each repetition but not before the first, or throughout the entire time of the treatment). If the test is positive, the planned activities have clearance for execution as an actual activity. At that time, the pause quantity timer is started and the actual activities are executed after the pause quantity has elapsed. Pause quantity is allowed to be negative provided that it is possible to predict the occurrence of the target treatment (e.g., administer 3 hours prior to surgery). Treatments can be bound by a specified time period, can iterate in a loop and can have exit and entry criteria (Table 8: Assignment Criteria). The criteria can be a complex set of rules and sub rules of "and" and "or" criteria (Table 14: Conjunction Types). Each criteria can be based on an observation (e.g., male or female; LDL cholesterol above 240 mg/dL). The storage of the observation could be of many data types such as plain text, ratio, and physical quantity (Table 15: Data Types). Entry to a treatment can also be based on randomization. Subjects are assigned to treatments (Table 120: Treatments Planned Subjects).

Data can be stored in many formats, including but not limited to, dates, data ranges, ratios, physical quantities, a range of physical quantities, real, a range of real, string, and coded value. The uses of the data types are documented in the tables. Regarding the coded value (e.g. controlled vocabulary), in many tables (e.g., observation) there are two links to the observation types. One link is for the type of observation (e.g., pain index), the other link is the coded value for the result (e.g., extreme pain).

Now the count and type research subjects are planned (FIGS. 10 and 10b: Planned Research Subject). The planned research subject (Table 56: Planned Research Subject) could by a person, a non-human living subject, a product, a tissue, an organ or part of a person (Table 115: Target Sites), non-human living subject or product (Table 84: Research Subject Types). When the planned subject is living, the species (Table 93: Species) may be noted. There could be relevance to who a subject is related with (Table 59: Planned Subject) and the type of relationship (Table 109: Subject Relationship Types) (e.g., parent, roommate). Experimental units (i.e., subjects) are sometimes segregated and/or assigned to a treatment based on certain criteria (Table 58: Planned Subject Condition). For example, site 1 might enroll 8 males and 12 females, where site 2 enrolls 12 males and 8 females. A planned subject condition is type of observation. Like observation, a planned subject condition can be stored with different data types.

After the experiment is designed, the types of research subjects are defined and treatments are determined, the researcher would create eligibility criteria (FIG. 22). The eligibility criteria (Table 20: Eligibility Criteria) is a complex set of rules to determine if a subject is eligible to participate in the study. Eligibility criteria has the same set of "and" and "or" criteria as the treatment workflow, and like the treatment workflow, is based on a complex set of observations.

Next, the detailed schedule of planned activities (FIG. 28) is determined. Typically the planned activities are broken by visits or encounters (Table 52: Planned Encounter) with the researcher, but does not have to be. The activities planned to be performed are, collectively, referred to herein as a plurality or set of planned activities and are stored in a set of objects. At the visit, the researcher can supply (Table 60: Planned Supplies) the intervention. The supplied intervention could be a substance administration (Table 51: Planned Administration). The planned intervention could also be a surgery (Table 55: Planned Procedure). During the visit, many observations (Table 54: Planned Observation) occur (e.g., weight, blood pressure). Each planned activity can have a specified duration or can be an offset in time from another planned activity, encounter or treatment. For human clinical trials, case report forms are created at this time.

Planned activities do not have a particular start and stop time. The planned activity starts from an offset (Table 46: Offset Type) of another planned activity, encounter, treatment or the start of the study. For example, an encounter can start on day 13 of a trial, as opposed to January $13^{th}$. The offset could be a window (e.g., day 14+−1 day). Planned activities do have a duration that is measured to a specific time unit (Table 116: Time Units) (e.g., seconds).

Planned observations can be complex (FIG. 15). The types of planned observation can be vast (Table 42: Observation Types), from a simple blood pressure to a compound observation like the Barthel Index. The planned observation can be planned to be stored in varied data type including but not limited to, a controlled term, a physical quantity, a ratio, a string, and a numeric value. When the observation is a physical quantity, the quantity has a unit of measure (Table 71: Quantity Units) (e.g., pounds). The observation can be made about a particular location on the subject (Table 115: Target Sites). Observations have different means or techniques used to ascertain the observation (Table 40: Method Types). The observation can be made from a specimen (Table 45: Observation Specimen) collected from the subject. The observation can have qualitative interpretation (Table 34: Interpretation Types); such as abnormal.

Each observation can have a reference range (Table 79: Reference Range). Reference ranges are essentially descriptors of a result values assumed to be "normal", "abnormal", or "critical." Those can vary by sex, age, or any other criterion (Table 77: Reference Range Criteria). The reference range can have a qualitative interpretation and the range may or may not be specific to a lab or facility.

A planned substance administration (FIG. 4) (Table 51: Planned Administration) is a type of procedure that involves a performer introducing or otherwise applying a product (Table 68: Product) into or to the experimental unit. There are many types of substances (Table 2: Administration Types). For purposes of this definition, photons and other models of radiation or light energy are considered substances. Substances may also include living entities such as live virus vaccines and other materials containing infectious agents, e.g., saliva, blood products. There are different routes (Table 88: Routes of Administration) in which a substance can be administered. A substance can be administered to a certain location on the subject (Table 3: Approach Sites). If there are changes to the dose, the reason for that change is recorded.

A planned procedure (FIG. 12) is a planned activity whose immediate and primary outcome (post-condition) is the alteration of the physical condition of the subject. A procedure (Table 55: Planned Procedure) does not comprise all planned activities having an intervention intent. Whether the bodily alteration is appreciated or intended as beneficial to the subject is likewise irrelevant. Taking an x-ray image may sometimes be called "procedure," but it is not a procedure because an x-ray image is not done to alter the physical condition of the body. The x-ray is a substance administration. There are many different types of procedures (Table 63: Procedure Type). A procedure can approach a specific location (Table 3: Approach Sites) on the subject to target a specific location (Table 115: Target Sites) on the subject. For example, an arteria pulmonalis catheter targets a pulmonary artery, but the approach site is typically the vena carotis interna at the neck or the vena subclavia at the fossa subclavia. There can be different means or technique used to perform the procedure (Table 40: Method Types). The procedure can attach a product or can collect a specimen (Table 57: Planned Specimen). There are many types of specimen (Table 94: Specimen Types) that can be collected (e.g., blood, urine) and there is a process that is followed to collect those specimen (Table 38: Lab Process). There are many types of lab processes (Table 37: Lab Process Types); typical process steps include Specimen Collection, Specimen Accession, and Specimen Separation.

Product or material can be planned to be supplied to subjects (FIG. 2). For example, an investigator provides the subject with a bottle of 20 pills. Most of the detailed information about the supply (Table 60: Planned Supplies) should be represented by the product (Table 68: Product). The quantity (Table 71: Quantity Units) of the supply is needed in the planned supplies table.

When the plan is complete, the research needs to find sites (FIG. 7) where the study will be performed, investigators (FIG. 18) to carry out the study and service providers (FIG. 8) to perform actual activities like a central lab.

The site (Table 92: Sites) is one location where subjects go for treatment. In the planning stage, the site's physical site might not be known. Accordingly, a planning site is documented. A specified time could be documented for the use of the study (Table 102: Study Definition Sites). The site used in the study is commonly known as the study site (Table 98: Study Sites). Sites are not necessarily where treatment happens, but more of an area that can be used for analysis to determine that the intervention had an effect based on the site. Service delivery location (Table 89: Service Delivery Location) is the physical location where treatment occurs.

There could be many investigators (Table 35: Investigators) for a study and the same investigator can perform actual activities for many studies (Table 36: Investigators Studies). An investigator is associated to a study site and must be qualified (Table 70: Qualification) with such things as a degree or certification to be an investigator for the specified study.

Then service providers (Table 90: Service Provider) with certain specialties are chosen for the study (Table 91: Service Provider in Study) in a certain site. The service provider could be a central lab, a data safety monitoring board or something else.

Once the study is designed, treatments are determined, investigators and sites are chosen and service providers are picked, the researcher then will seek independent approval through an institutional review board (IRB) or ethical committee (FIG. 21). The ethical committee (Table 26: Ethical Committee) is a group that approves studies (Table 108: Subject Protection Approval) to be performed on humans. The ethical committee approves the sites, investigators, design, treatments and other documentation. The ethical committee also determines the start and end of the study.

If the experimental product is regulated, the research forwards all of the information about the study (e.g., experimental design, treatments, etc.), ethical committee and participants (e.g., investigator, service provider, sites, etc.) to a regulator. The regulator would also receive summary information (FIG. 3) about the study. The summaries (Table 112: Study Summaries) would include, but are not limited to, the number of subjects, the randomization scheme, the phase of the study, objective, indication, min age of the subject, max age of the subject, and route of administration.

The study begins with the recruitment of research subjects (FIGS. 9a and 9b: Research Subject). The research subject (Table 85: Research Subjects) could by a person, a non-human living subject, a product, a tissue, an organ or part of a person (Table 115: Target Sites), non-human living subject or product (Table 84: Research Subject Types). When the subject is living, the species (Table 93: Species) may be noted. Different organization might have different identifiers for the subject (Table 83: Research Subject); such as, the hospital might have one identifier for the subject and the researcher might have another identifier. There could be relevance to who a subject is related with (Table 110: Subject Cross Table) and the type of relationship (Table 109: Subject Relationship Types) (e.g., parent, roommate). There are some basic demographic information that is of interest about the subject; such as gender (Table 30: Gender), race (Table 72: Race), ethnic group (Table 27: Ethnic Group) and for a product, dosage form (Table 19: Dosage Form).

Next, screening of the subject begins. From the screening it is possible that the study plan will have to change. For example, the eligibility criteria may need to be loosened because patient recruitment is low. An amendment may be needed to the study design (FIG. 6). All of the study design is linked together (Table 106: Study Master). That is, there are different versions of the same study. Each study can also be referred to by a different identifier (Table 105: Study Identifiers). For example, the researcher could have an identification system for studies. When that study is sent to the ethical committee, the ethical committee assigns their own identifier. When the study is sent to a government, the government has their own identifier. Furthermore, the same study can be performed at a different time by a different organization.

When the study is performed at different times, it is considered a different execution of the study (FIG. 7). For each run of a study (Table 103: Study Events), based on the study design, there is a start and end of that study. That study is actually performed at a site (Table 92: Sites) and services (e.g., substance administration, supplies, visits, observations) are delivered at certain locations (Table 97: Study Site Location). Not all service delivery location and sites are specified in the initial study design.

Both the site and the study can be in a different state, including but not limited to recruiting subject, collecting data and analyzing data (Table 99: Study Sites Statues and Table 104: Study Event Statuses). Each status type can have a state, including but not limited to active, closed, complete, and hold. Both statuses are required since one cannot determine the state of the study based on the state of each site. For example, if all of the sites are collecting data, the study can be in the search of a new site and is still in the state of recruiting patients. Each state starts at a specified time and both the site and the study can enter the same state more than once. For example, a site that is closed to recruiting subject can subsequently become open to recruiting subjects again.

The investigator performs actions and collects data (FIGS. 23a and 23b: Audit) on research subjects (FIGS. 27a and 27b: Research Subject Activities). The actions performed and the data collected are, collectively, referred to herein as a plurality or set of actual activities and are stored in a set of objects. These actual activities may or may not occur during an encounter (Table 23: Encounters). Not all encounters are visits. Encounters may include journal entries and phone calls. (Table 22: Encounter Types). Actions have a time that the action occurred and a time that the data was collected. An actual activity or type of data collected could be an observation (Table 43: Observations), substance administration (Table 111: Substance Administration), a supply of product (Table 113: Supplies) and a procedure (Table 64: Procedures).

All actual activities can start and end at a particular time and can have a duration that is measured to a specific time unit (Table 116: Time Units) (e.g., seconds). If an actual activity is modified, the person who modified the record and the reason why they modified the record must be maintained and must point to the old record. Accordingly, each collected data needs an audit trail (FIG. 23a). There are a few standard way to store audit trails. One would be to have one table listing every field that changes. Another way would be to have a shadow table for each table where each table that can be modified would have a duplicate table with extra fields if the action was an insert, delete or edit, the date and time of the action and who did the action. Yet another type would be to list all of the audit trails in one table. The present invention uses this last option. Accordingly, the status (Table 96: Status) table is a lookup to determine the status of any row in a table. The scope of the present invention includes other types of audit trails. The data recording could occur via an investigator, service provider or device (Table 17: Devices).

Observations can be complex (FIG. 16). The types of observation can be vast (Table 42: Observation Types), from a simple blood pressure to a compound observation like the Barthel Index. The observation can be stored in varied data type including, but not limited to, a controlled term (Table 41: Observation Result Types), a physical quantity, a ratio, a string, and a numeric value. When the observation has a physical quantity, the quantity has a unit of measure (Table 71: Quantity Units) (e.g., pounds). The observation can be made about a particular location on the subject (Table 115: Target Sites). Observations have different means or technique used to ascertain the observation (Table 40: Method Types). The observation can be made from a specimen (Table 45: Observation Specimen) collected from the subject. The observation can have qualitative interpretation (Table 34: Interpretation Types) such as "abnormal."

Each observation can have a reference range (FIG. 17). Reference ranges (Table 79: Reference Range) are essentially descriptors of a result values assumed to be "normal", "abnormal", or "critical." Those can vary by sex, age, or any other criterion (Table 77: Reference Range Criteria). The reference range can have a qualitative interpretation and the range may or may not be specific to a lab or facility.

A substance administration (FIG. 5) (Table 111: Substance Administration) is a type of procedure that involves a performer introducing or otherwise applying a product (Table 68: Product) into or to the experimental unit. There are many types of substances (Table 2: Administration Types). For purposes of this definition, photons and other models of radiation or light energy are considered substances. Substances may also include living entities such as live virus vaccines and other materials containing infectious agents, e.g., saliva, and blood products. There are different routes (Table 88: Routes of Administration) that a substance can be administered. A substance can be administered to a certain location on the subject (Table 3: Approach Sites). If there are changes to the dose, the reason for that change is recorded.

A procedure (FIG. 13) is an actual activity whose immediate and primary outcome (post-condition) is the alteration of the physical condition of the subject. A procedure (Table 64: Procedures) does not comprise all actual activities having an intervention intent. Whether the bodily alteration is appreciated or intended as beneficial to the subject is likewise irrelevant. Taking an x-ray image may sometimes be called "procedure," but it is not a procedure because an x-ray image is not done to alter the physical condition of the body. The x-ray is a substance administration. There are many different types of procedures (Table 63: Procedure Type). A procedure can approach a specific location (Table 3: Approach Sites) on the subject to target a specific location (Table 115: Target Sites) on the subject. For example: An arteria pulmonalis catheter targets a pulmonary artery, but the approach site is typically the vena carotis interna at the neck or the vena subclavia at the fossa subclavia. There can be different means or technique used to perform the procedure (Table 40: Method Types). The procedure can attach a product or can collect a specimen (Table 95: Specimen). There are many types of specimen (Table 94: Specimen Types) that can be collected (e.g., blood, urine) and there is a process that is followed to collect those specimen (Table 38: Lab Process). There are many types of lab processes (Table 37: Lab Process Types); typical process steps include Specimen Collection, Specimen Accession, and Specimen Separation.

Product or material can be planned to be supplied to subjects (FIG. 1). For example, an investigator provides the subject with a bottle of 20 pills. Most of the detailed information about the supply (Table 113: Supplies) should be represented using by the product. The quantity (Table 71: Quantity Units) of the supply is needed in the supplies table. If a product (Table 65: Product Instance) is administered or supplied, the product could have been produced in a lot (Table 39: Lots). A lot identifies an amount of the product that has been produced or otherwise processed together.

When there is an investigation, assessments (FIGS. 25a and 25b: Assessments on Observations (Adverse Events)) are made. One example of when assessments are made is determining an adverse event. When an adverse event report (Table 81: Reports) is created, source documents (Table 18: Documents) (e.g., doctor's note) are attached to the report (Table 82: Report Documents). The report itself is completed on a certain date and the report is made available on a certain date.

An assessment (Table 5:) is a kind of observation that allows a secondary observation (Table 6: Assessments Observations) to assert (at various levels of probability) the cause (Table 12: Cause) (e.g., substance administration) of the event (actual activity) of a subject. One assessment can have many causes, one per evaluator. Based on the assessment, outcomes are recorded or actions are taken (e.g., stop taking drug) (Table 87: Results). The assessments are, collectively, referred to herein as a plurality or set of assessments and are stored in a set of objects.

Once data is available, analysis can begin. One type of analysis is to compare what actually happened to what was planned to occur (FIG. 26). Each actual activity could be associated with the planned activity, encounter or treatment. An encounter should be associated with a planned encounter. An actual research subject should be associated with a planned research subject. With these associations, an accounting can be provided for all of the actual activities that should have occurred for the planned research subject and match that against what actually occurred. For example, if a physical exam was supposed to occur at an encounter, a check is made to see if that physical exam actually occurred. Furthermore, a comparison can be made between the actual subject observations and the eligibility criteria to determine if the subject was fit for the study. For example, if there is an eligibility criteria that states that all subject must be from the age of 10 to 18, one can calculate that against a subject that has an age of 20.

For analysis purposes, planned and actual activities can be organized (FIG. 14). Organizers (Table 49: Organizers) are used to group a set of planned or actual activities (Table 50: Organizer Actions) sharing a common context. Organizers can nest within other organizers, such as where a document is contained within a folder, or a folder is contained within an Electronic Health Record (HER) extract.

There are many tables that have the word "type" in them. The "type" is a controlled term or lookup table that explains what the main table (e.g., the main table for assignment types is assignment) entry is. For example, an assignment can have the type of randomization or observation. Type tables are one method that can be used to determine the type of row. However, the scope of the present invention includes other methods used to determine the type of row. For example, one might have a check constraint on a table with values for each type. The type could be a number or text.

The following are a list of type tables used in this invention: Table 1: Action Types, Table 2: Administration Types, Table 9: Assignment Observation Types, Table 10: Assignment Types, Table 11: Causes Types, Table 14: Conjunction Types, Table 21: Eligibility Observation Types, Table 22: Encounter Types, Table 24: Epoch Types, Table 28: Evaluator Type, Table 32: Ingredient Types, Table 34: Interpretation Types, Table 37: Lab Process Types, Table 41: Observation Result Types, Table 42: Observation Types, Table 44: Observation Cross Table Types, Table 47: Offset From Type, Table 48: Organizer Types, Table 53: Planned Observation Cross Table Types, Table 61: Planned Subject Condition Observation Type, Table 62: Planned Subject Condition Result Type, Table 63: Procedure Type, Table 69: Qualification Type, Table 73: Reference Criteria Observation Types, Table 76: Reference Observation Types, Table 74: Reference Observation High Type, Table 75: Reference Observation Low Type, Table 78: Reference Range Types, Table 80: Reference Result Code Type, Table 84: Research Subject Types, Table 86: Result Types, Table 94: Specimen Types, Table 100: Study Characteristic Types, Table 107: Study Status Types, Table 109: Subject Relationship Types, Table 114: Supply types and Table 117: Treatment Types.

Many databases handle auto-generated unique identifiers differently. This example does not use built-in database functions to handle auto-generated unique identifiers. This example has a table called identifiers (Table 31: Identifiers) to manage the unique identifier. The table name is the name of the table for the unique identifier and a system queries and adds one to the table to generate a unique identifier. The scope of the present invention includes other types of methods to create unique identifiers, such as using a built-in sequence number in Oracle® or using a combination of unique keys instead of a single primary key.

Different hardware configurations can be used with the present invention. In one example (FIG. 30), several individuals (e.g. statisticians, medical professional, researcher) receive views of the data by querying a database via an electronic network (e.g., the Internet) for information. The individuals may communicate using various forms of data receivers, such as portable computers, handheld computers, and tablet computers. The queries are processed by one or more processors within an application server that communicates with the database server. Each of the processors may be any general-purpose computer, such as a personal computer (PC) that runs a Microsoft Windows® operating system or a mainframe computer running a UNIX-type operating system.

Since many users may simultaneously query for data, the application server may be clustered and/or an application pool may be utilized. Also, since there could be a tremendous amount of stored data, the database can also be clustered. The tables may reside in one or more hard drive. Multiple hard drives may be preferred due to the large amount of data. Furthermore, source clinical data repositories would export data to be stored by the illustrated storage elements.

Referring to FIG. 30, in one preferred embodiment of the present invention, a computer 10 for processing the types of data discussed herein is provided. The computer 10 includes a memory 12 in database server 14 configured to store an operating system 16, a database schema 18, and a database 20. The operating system 16 includes an object-oriented database engine 22. The database schema 18 is maintained by the object-oriented database engine 22 of the operating system 16. The computer 10 also includes memory 24 in application server 26 configured to store an operating system 28 and computer instructions 30 to create, read, update and delete information in the database 20. The computer 10 is in communication with a plurality of data receivers 32 and a source of clinical data 34 via an electronic network 36, such as the internet.

In another embodiment, a computer program product for processing the types of data discussed herein is provided. The computer program product includes non-transitory computer-readable media encoded with instructions for execution by a processor to configure the operating system that includes the object-oriented database engine, maintain the database schema by the object-oriented database engine of the operating system, and maintain the database.

Detailed Description of Tables and Columns

Table 1: Action Types

TABLE 1

Action Types

| Table Name | Entity/Column Name | Description |
|---|---|---|
| ACTION_TYPES | ENTITY | Either a supply, substance administration, procedure or observation. |
| ACTION_TYPES | ACTION_TYPE_ID | Unique identifier |
| ACTION_TYPES | DESCRIPITION | Text description of the actions |

TABLE 2

Administration Types

| Table Name | Entity/Column Name | Description |
|---|---|---|
| ADMINISTRATION_TYPES | ENTITY | The type of administration |
| ADMINISTRATION_TYPES | ADMINISTRATION_TYPE_ID | Unique identifier |
| ADMINISTRATION_TYPES | DESCRIPTION | Friendly name of identifier |
| ADMINISTRATION_TYPES | CODE | Code from the coding system |

TABLE 2-continued

Administration Types

| Table Name | Entity/Column Name | Description |
|---|---|---|
| ADMINISTRATION_TYPES | CODE_SYSTEM | Code system of the code |
| ADMINISTRATION_TYPES | CODE_SYSTEM_VERSION | Version of the code system version of the code |

TABLE 3

Approach Sites

| Table Name | Entity/Column Name | Description |
|---|---|---|
| APPROACH_SITES | ENTITY | The anatomical site or system through which the procedure reaches its target. For example: An arteria pulmonalis catheter targets a pulmonary artery, but the approach site is typically the vena carotis interna at the neck or the vena subclavia at the fossa subclavia. |
| APPROACH_SITES | APPROACH_SITE_ID | Unique identifier |
| APPROACH_SITES | DESCRIPTION | Friendly name of identifier |
| APPROACH_SITES | CODE | Code from the coding system |
| APPROACH_SITES | CODE_SYSTEM | Code system of the code |
| APPROACH_SITES | CODE_SYSTEM_VERSION | Version of the code system version of the code |

TABLE 4

Arms

| Table Name | Entity/Column Name | Description |
|---|---|---|
| ARMS | ENTITY | A path through the study which describes what planned activities the subject will be involved in as they pass through the study, and are typically equivalent to a treatment group in a parallel design trial. Generally, each subject is assigned to an Arm, and the design of the study is reflected in the number and composition of the individual arms. This intended path of the subject progressing in a trial is composed of a time point events (study cell) for each Epoch of the study. Each time point events, in turn, has a pattern of child time points through which the subject would pass. This planned path thus describes how subjects assigned to the Arm will be treated. |
| ARMS | ARM_ID | Unique identifier |
| ARMS | STUDY_DEFINITION_ID | Study definition where the arm is defined |
| ARMS | TITLE | The title of the arm |
| ARMS | SOURCE_ID | The arm identifier as defined in the source document |

TABLE 5

Assessments

| Table Name | Entity/Column Name | Description |
|---|---|---|
| ASSESSMENTS | ENTITY | A kind of observation that allows a Secondary Observation (observation assessment) to assert (at various levels of probability) that the target of the association (which may be of any type of cause) is implicated in the etiology of another observation that is named as the subject of the Secondary Observation. The assessment is about one or more secondary observations and what caused those observations. One assessment can have many causes, one per evaluator. |
| ASSESSMENTS | REPORT_ID | The report that contains the assessment |
| ASSESSMENTS | RESEARCH_SUBJECT_ID | The subject of the assessment |
| ASSESSMENTS | INVESTIGATOR_ID | If the investigator made the assessment |
| ASSESSMENTS | SERVICE_PROVIDER_ID | If the service provider made the assessment |
| ASSESSMENTS | DEVICE_ID | If the device made the assessment |
| ASSESSMENTS | REASON | The reason for the assessment |
| ASSESSMENTS | DATE_EFFECTIVE_HIGH | The date range of when the assessment occurred |
| ASSESSMENTS | DATE_EFFECTIVE_LOW | The date range of when the assessment occurred |
| ASSESSMENTS | DURATION | The duration of the assessment |
| ASSESSMENTS | DURATION_TIME_UNIT_ID | The duration of the assessment |
| ASSESSMENTS | SOURCE_ID | Source identifier of the assessment |
| ASSESSMENTS | EVALUATOR_TYPE_ID | Who made the assessment (e.g. patient, drug company, investigator, device, service provider, etc.) |

TABLE 6

Assessments Observations

| Table Name | Entity/Column Name | Description |
| --- | --- | --- |
| ASSESSMENTS_OBSERVATIONS | ENTITY | One observation can be referred to in many assessments and an assessment can be based on many observations. |

TABLE 7

Assignment

| Table Name | Entity/Column Name | Description |
| --- | --- | --- |
| ASSIGNMENT | ENTITY | Treatments have exit and entry criteria and uses workflow control suite of attributes. |
| ASSIGNMENT | ASSIGNMENT_ID | Unique identifier |
| ASSIGNMENT | ASSIGNMENT_TYPE_ID | If the assignment is based on randomization or observation |
| ASSIGNMENT | TREATMENT_ID | The treatment |
| ASSIGNMENT | DESCRIPTION | The textual description of the assignment |

TABLE 8

Assignment Criteria

| Table Name | Entity/Column Name | Description |
| --- | --- | --- |
| ASSIGNMENT_CRITERIA | ENTITY | Each assignment has criteria to determine if the assignment will be executed |
| ASSIGNMENT_CRITERIA | ASSIGNMENT_CRITERION_ID | Unique identifier |
| ASSIGNMENT_CRITERIA | ASSIGNMENT_ID | The assignment |
| ASSIGNMENT_CRITERIA | PARENT_ID | If the criteria is completes the parent criteria |
| ASSIGNMENT_CRITERIA | CONJUNCTION_TYPE_ID | The logical conjunction of the criteria among all the rules (e.g., and, or, exclusive-or). |
| ASSIGNMENT_CRITERIA | RESULT_REAL | Used when the data type is physical quantity, ratio or real. Result is a numeric value of the observation |
| ASSIGNMENT_CRITERIA | RESULT_UNIT_ID | Used when the data type is physical quantity or ratio. The unit of measure of the result. The numeric value will be located in the result_real. |
| ASSIGNMENT_CRITERIA | RESULT_STRING | Used when the data type is string. The result of the observation |
| ASSIGNMENT_CRITERIA | RESULT_DATE_LOW | Used when the data type is date. The result of the observation |
| ASSIGNMENT_CRITERIA | RESULT_DATE_HIGH | Used when the data type is date. The result of the observation |
| ASSIGNMENT_CRITERIA | RESULT_DENOM_REAL | Used when the data type is ratio. The numeric denominator result of the operation |
| ASSIGNMENT_CRITERIA | RESULT_DENOM_UNIT_ID | Used when the data type is ration. The unit of measure of the denominator of the result of the observation |
| ASSIGNMENT_CRITERIA | NEGATION | Explains the results are the opposite of what is stated |
| ASSIGNMENT_CRITERIA | SEQ | The order of the child criteria |

TABLE 9

Assignment Observation Types

| Table Name | Entity/Column Name | Description |
| --- | --- | --- |
| ASSIGNMENT_OBSERVATION_TYPES | ENTITY | The type of observation in coded values. Since coded systems can be post-coordinate, many codes could be present |
| ASSIGNMENT_OBSERVATION_TYPES | SEQ | The order the code appeared in the observation |
| ASSIGNMENT_RESULTS_OBS_TYPES | ENTITY | The type of observation in coded values. Since coded systems can be post-coordinate, many codes could be present |
| ASSIGNMENT_RESULTS_OBS_TYPES | SEQ | The order the code appeared in the observation |

TABLE 10

Assignment Types

| Table Name | Entity/Column Name | Description |
| --- | --- | --- |
| ASSIGNMENT_TYPES | ENTITY | If the assignment is based on randomization or observation |
| ASSIGNMENT_TYPES | ASSIGNMENT_TYPE_ID | Unique identifier |
| ASSIGNMENT_TYPES | DESCRIPTION | Friendly name of identifier |
| ASSIGNMENT_TYPES | CODE | Code from the coding system |
| ASSIGNMENT_TYPES | CODE_SYSTEM | Code system of the code |
| ASSIGNMENT_TYPES | CODE_SYSTEM_VERSION | Version of the code system version of the code |

TABLE 11

Causes Types

| Table Name | Entity/Column Name | Description |
| --- | --- | --- |
| CAUSE_TYPES | ENTITY | The type of cause (e.g., need examples) |
| CAUSE_TYPES | CAUSE_TYPE_ID | Unique identifier |
| CAUSE_TYPES | CODE | Code from the coding system |
| CAUSE_TYPES | CODE_SYSTEM | Code system of the code |
| CAUSE_TYPES | CODE_SYSTEM_VERSION | Version of the code system version of the code |
| CAUSE_TYPES | DESCRIPTION | Friendly name of identifier |

TABLE 12

Cause

| Table Name | Entity/Column Name | Description |
| --- | --- | --- |
| CAUSES | ENTITY | A kind of observation that allows a Secondary Observation (source act) to assert (at various levels of probability) that the target act of the association (which may be of any type of act) is implicated in the etiology of another observation that is named as the subject of the Secondary Observation |

TABLE 13

Check Points

| Table Name | Entity/Column Name | Description |
| --- | --- | --- |
| CHECK_POINTS | ENTITY | A code specifying when in the rules are evaluated (e.g., before the treatment starts for the first time, before every repetition, after each repetition but not before the first, or throughout the entire time of the treatment.) |
| CHECK_POINTS | CHECK_POINT_ID | Unique Identifier |
| CHECK_POINTS | DESCRIPTION | Friendly name of identifier |

TABLE 13-continued

Check Points

| Table Name | Entity/Column Name | Description |
| --- | --- | --- |
| CHECK_POINTS | CODE | Code from the coding system |
| CHECK_POINTS | CODE_SYSTEM | Code system of the code |
| CHECK_POINTS | CODE_SYSTEM_VERSION | Version of the code system version of the code |

TABLE 14

Conjunction Types

| Table Name | Entity/Column Name | Description |
| --- | --- | --- |
| CONJUNCTION_TYPES | ENTITY | The logical conjunction of the criteria among all the rules |
| CONJUNCTION_TYPES | CONJUNCTION_TYPE_ID | Unique identifier |
| CONJUNCTION_TYPES | DESCRIPTION | Friendly name of identifier |
| CONJUNCTION_TYPES | CODE | Code from the coding system |
| CONJUNCTION_TYPES | CODE_SYSTEM | Code system of the code |
| CONJUNCTION_TYPES | CODE_SYSTEM_VERSION | Version of the code system version of the code |

TABLE 15

Data Types

| Table Name | Entity/Column Name | Description |
| --- | --- | --- |
| DATATYPES | ENTITY | The type of data (e.g., physical quantity, real, string, coded) that will be used |
| DATATYPES | DATATYPE_ID | Unique Identifier |
| DATATYPES | DESCRIPTION | Friendly name of identifier |

TABLE 16

Device Identifier

| Table Name | Entity/Column Name | Description |
| --- | --- | --- |
| DEVICE_IDENTIFIER | ENTITY | Unique identifier of the device |

TABLE 17

Devices

| Table Name | Entity/Column Name | Description |
| --- | --- | --- |
| DEVICES | ENTITY | A device that is a data enterer. One device can be used on many studied |
| DEVICES | DEVICE_ID | Unique identifier |
| DEVICES | MODEL_NUMBER | The human designated moniker for a device, assigned by the manufacturer. |
| DEVICES | SOFTWARE_NAME | The moniker, version and release of the software that operates the device as assigned by the software manufacturer or developer. |

TABLE 18

| | Documents | |
|---|---|---|
| Table Name | Entity/Column Name | Description |
| DOCUMENTS | ENTITY | There could be several documents in a report |

TABLE 18-continued

| | Documents | |
|---|---|---|
| Table Name | Entity/Column Name | Description |
| DOCUMENTS | DOCUMENT_ID | Unique identifier |
| DOCUMENTS | URL | Location of the document |

TABLE 19

| | Dosage Form | |
|---|---|---|
| Table Name | Entity/Column Name | Description |
| DOSAGE_FORMS | ENTITY | such as tablet, ointment, gel, etc |
| DOSAGE_FORMS | DOSAGE_FORM_ID | Unique identifier |
| DOSAGE_FORMS | DESCRIPTION | Friendly name of identifier |
| DOSAGE_FORMS | CODE | Code from the coding system |
| DOSAGE_FORMS | CODE_SYSTEM | Code system of the code |
| DOSAGE_FORMS | CODE_SYSTEM_VERSION | Version of the code system version of the code |

TABLE 20

| | Eligibility Criteria | |
|---|---|---|
| Table Name | Entity/Column Name | Description |
| ELIGIBILITY_CRITERIA | ENTITY | Eligibility criteria are a set of conditions that a subject must meet in order to participate in a study. Because eligibility criteria affect recruitment into a study, they are often the subject of protocol amendments, and one criterion may be superseded by another. The most commonly occurring types of criteria involve age, sex, the type and stage of a disease, treatment history, and other medical conditions. For a full description of how conditions work review the Condition section. |
| ELIGIBILITY_CRITERIA | STUDY_DEFINITION_ID | The study that defines the eligibility criteria |
| ELIGIBILITY_CRITERIA | PARENT_ID | If the criteria is complex (e.g., (A AND B) OR (C AND D)) the parent id is the criteria identifier of this sub rule |
| ELIGIBILITY_CRITERIA | CONJUNCTION_TYPE_ID | The logical conjunction of the criteria among all the criteria (e.g., and, or, exclusive-or). |
| ELIGIBILITY_CRITERIA | DATATYPE_ID | The type of data (e.g., physical quantity, real, string, coded) that will be used in the criteria |
| ELIGIBILITY_CRITERIA | RESULT_REAL | Only used if data type is a physical quantity, ratio, or real. Value of the criteria. |
| ELIGIBILITY_CRITERIA | RESULT_UNIT_ID | Only used if data type is a physical quantity or ratio. Unit of measure of the value of the criteria. |
| ELIGIBILITY_CRITERIA | RESULT_STRING | Only used if data type is a string. Value of the criteria. |
| ELIGIBILITY_CRITERIA | RESULT_DATE_LOW | Only used if data type is a date. Value of the criteria. |
| ELIGIBILITY_CRITERIA | RESULT_DATE_HIGH | Only used if data type is a date. Value of the criteria. |
| ELIGIBILITY_CRITERIA | RESULT_DENOM_REAL | Only used if data type is a ratio. Value of the denominator rule. |
| ELIGIBILITY_CRITERIA | RESULT_DENOM_UNIT_ID | Only used if data type is a ratio. Unit of measure of the denominator of the value of the rule. |
| ELIGIBILITY_CRITERIA | NEGATION | The criteria is the opposite (e.g., if the code is fever, then when negation is set to true, the criteria will be absent of fever). |
| ELIGIBILITY_CRITERIA | DESCRIPTION | The full textual description of the criteria |
| ELIGIBILITY_CRITERIA | SOURCE_ID | The identifier in the source document |

TABLE 21

Eligibility Observation Types

| Table Name | Entity/ Column Name | Description |
| --- | --- | --- |
| ELIGIBILITY_OBSERVATION_TYPES | ENTITY | The type of observation in coded values. Since coded systems can be post-coordinate, many codes could be present |
| ELIGIBILITY_OBSERVATION_TYPES | SEQ | The order the code appeared in the observation |
| ELIGIBILITY_RESULTS_OBS_TYPES | ENTITY | The type of observation in coded values. Since coded systems can be post-coordinate, many codes could be present |
| ELIGIBILITY_RESULTS_OBS_TYPES | SEQ | The order the code appeared in the observation |

TABLE 22

Encounter Types

| Table Name | Entity/Column Name | Description |
| --- | --- | --- |
| ENCOUNTER_TYPES | ENTITY | The types of encounter (e.g., visit, journal, phone call) |
| ENCOUNTER_TYPES | ENCOUNTER_TYPE_ID | Unique identifier |
| ENCOUNTER_TYPES | DESCRIPTION | Friendly name of identifier |
| ENCOUNTER_TYPES | CODE | Code of the encounter |
| ENCOUNTER_TYPES | CODE_SYSTEM | Code system of the code |
| ENCOUNTER_TYPES | CODE_SYSTEM_VERSION | Version of the code system version of the code |

TABLE 23

Encounters

| Table Name | Entity/ Column Name | Description |
| --- | --- | --- |
| ENCOUNTERS | ENTITY | An interaction between an experimental unit and an investigator for the purpose of providing study related services. |
| ENCOUNTERS | ENCOUNTER_ID | Unique identifier |
| ENCOUNTERS | ENCOUNTER_TYPE_ID | The type of encounter (e.g., visit, journal entry). |
| ENCOUNTERS | RESEARCH_SUBJECT_ID | The encounter is unique based on research subject and unique identifier. |
| ENCOUNTERS | DESCRIPTION | Textual description of the encounter |
| ENCOUNTERS | DATE_EFFECTIVE_HIGH | Start date and time of encounter. |
| ENCOUNTERS | DATE_EFFECTIVE_LOW | End date and time of encounter |
| ENCOUNTERS | AVAILABLE_DATE | The point in time at which information about this encounter first became available to a system reproducing this encounter. The availability date is metadata describing the record, not the encounter. |
| ENCOUNTERS | DURATION | The magnitude of the quantity measured in terms of the unit of the duration |
| ENCOUNTERS | DURATION_TIME_UNIT_ID | The unit of measure specified for the duration |
| ENCOUNTERS | PLANNED_ENCOUNTER_ID | Link to the planned encounter |
| ENCOUNTERS | TREATMENT_ID | The treatment that this encounter is within |
| ENCOUNTERS | IS_CURRENT | If true the this record is the most current |
| ENCOUNTERS | MODIFIED_REASON | The reason for the modification |
| ENCOUNTERS | MODIFIED_ENCOUTNER_ID | The encounter records that this records modifies |
| ENCOUNTERS | MODIFIED_RESEARCH_SUBJECT_ID | The encounter record that this record modifies |

TABLE 24

Epoch Types

| Table Name | Entity/Column Name | Description |
| --- | --- | --- |
| EPOCH_TYPES | ENTITY | A coded value which indicates the general scope of the planned activities that occurin the epoch. Forexample, screening, treatment, follow-up, etc. |
| EPOCH_TYPES | EPOCH_TYPE_ID | Unique identifier |
| EPOCH_TYPES | TITLE | The description of the type of epoch |

TABLE 25

Epochs

| Table Name | Entity/Column Name | Description |
| --- | --- | --- |
| EPOCHS | ENTITY | A subject moves from one Epoch to another and can only be in one epoch at a time. The subject can only move to an Epoch with a greater sequenceNumber. The main purpose of the Epoch is to organize the Arms for comparison purposes. Planned activities in the same Epoch but a different Arm need not be similar in time and pattern. |
| EPOCHS | EPOCH_ID | Unique identifier |
| EPOCHS | STUDY_DEFINITION_ID | The study definition that defines the epoch |
| EPOCHS | EPOCH_TYPE_ID | A coded value which indicates the general scope of the planned activities that occur in the epoch. For example, screening, treatment, follow-up, etc. |
| EPOCHS | TITLE | The protocol-assigned name for an epoch. Note: When multiple Epochs have the same purpose (e.g., treatment), then the titles will probably include order numbers to distinguish them. For example, first treatment epoch, second treatment epoch, etc. or first wash-out epoch, second wash-out epoch. |
| EPOCHS | SEQUENCE | The order the epochs are executed |
| EPOCHS | DESCRIPTION | Human readable text which describes what happens to the subject during the epoch. |
| EPOCHS | SOURCE_ID | The identifier in the source document |

TABLE 26

Ethical Committee

| Table Name | Entity/Column Name | Description |
| --- | --- | --- |
| ETHICAL_COMMITTEES | ENTITY | A board that approves monitors and reviews biomedical research to protect the rights, safety and welfare of the subjects. An Ethical Committee performs critical oversight functions for research conducted on human subjects that are scientific, ethical, and regulatory. |
| ETHICAL_COMMITTEES | ETHICAL_COMMITTEE_ID | Unique identifier |

TABLE 27

Ethnic Group

| Table Name | Entity/Column Name | Description |
| --- | --- | --- |
| ETHNIC_GROUPS | ENTITY | The ethnic group |

TABLE 28

Evaluator Type

| Table Name | Entity/Column Name | Description |
| --- | --- | --- |
| EVALUATOR_TYPES | ENTITY | The type of the evaluator (e.g., investigator) |

TABLE 29

Gender Status

| Table Name | Entity/Column Name | Description |
| --- | --- | --- |
| GENDER_STATUSES | ENTITY | The status of the gender |

TABLE 30

Gender

| Table Name | Entity/Column Name | Description |
| --- | --- | --- |
| GENDERS | ENTITY | The gender |

TABLE 31

Identifiers

| Table Name | Entity/Column Name | Description |
|---|---|---|
| ID_REFS | ENTITY | To handle unique ids |

TABLE 32

Ingredient Types

| Table Name | Entity/Column Name | Description |
|---|---|---|
| INGREDIENT_TYPES | ENTITY | The kind of the ingredient |
| INGREDIENT_TYPES | INGREDIENT_TYPE_ID | Unique identifier |
| INGREDIENT_TYPES | CODE | Code from the coding system |
| INGREDIENT_TYPES | CODE_SYSTEM | Code system of the code |
| INGREDIENT_TYPES | CODE_SYSTEM_VERSION | Version of the code system version of the code |
| INGREDIENT_TYPES | ESTABLISHED_NAME | Friendly name of identifier |

TABLE 33

Ingredients

| Table Name | Entity/Column Name | Description |
|---|---|---|
| INGREDIENTS | ENTITY | A material (or chemical substance) in the make-up of the main product, not a structural part or content, and not a material added into a device for operation. For medicines and food this is obvious. For devices, an example for ingredient would be latex in a chest tube (but not an inhalant in a nebulizer device). |
| INGREDIENTS | INGREDIENT_ID | Unique identifier |
| INGREDIENTS | INGREDIENT_TYPE_ID | The code for an ingredient from a controlled vocabulary (e.g., the U.S. FDA UNII code). |
| INGREDIENTS | PRODUCT_ID | The product the ingredient is within |
| INGREDIENTS | ACTIVE | Whether the ingredient is active or inactive |
| INGREDIENTS | STRENGTH_NUMERATOR | A ratio specifying the strength of the ingredient as amount of ingredient substance (numerator) in amount of medicine (denominator). For example, a 50 mg tablet contains 50 mg in 1 tablet; a 50 mg per 5 mL syrup contains 50 mg in 5 mL. |
| INGREDIENTS | NUMERATOR_UNIT_ID | Unit of measure of the strength |
| INGREDIENTS | STRENGTH_DENOMERATOR | Strength in the denominator |
| INGREDIENTS | DENOMERATOR_UNIT_ID | Unit of measure of the strength |
| INGREDIENTS | CONFIDENTIAL | Is the ingredient confidential |
| INGREDIENTS | NAME | Name of the ingredient |
| INGREDIENTS | SOURCE_ID | The identifier in the source document |

TABLE 34

Interpretation Types

| Table Name | Entity/Column Name | Description |
|---|---|---|
| INTERPRETATION_TYPES | ENTITY | A qualitative interpretation of the observation. These interpretation codes are sometimes called "abnormal flags," however, the judgment of normalcy is just one of the interpretations, and is often not relevant. |
| INTERPRETATION_TYPES | INTERPRETATION_TYPE_ID | Unique identifier |
| INTERPRETATION_TYPES | DESCRIPTION | Friendly name of identifier |
| INTERPRETATION_TYPES | CODE | Code from the coding system |
| INTERPRETATION_TYPES | CODE_SYSTEM | Code system of the code |
| INTERPRETATION_TYPES | CODE_SYSTEM_VERSION | Version of the code system version of the code |

TABLE 35

Investigators

| Table Name | Entity/Column Name | Description |
|---|---|---|
| INVESTIGATORS | ENTITY | A researcher in a study who oversees aspects of the study, such as concept development, protocol writing, protocol submission for IRB approval, participant recruitment, informed consent, data collection, analysis, interpretation and presentation. A study can have one study primary investigator, although this is not required. There is one site primary investigator for each site for a study. There could be many sub-investigators for a study site. One investigator can be on several studies |
| INVESTIGATORS | INVESTIGATOR_ID | Unique identifier |

TABLE 36

Investigators Studies

| Table Name | Entity/Column Name | Description |
|---|---|---|
| INVESTIGATORS_STUDIES | ENTITY | The investigator on the study. |
| INVESTIGATORS_STUDIES | INVESTIGATOR_STUDY_ID | Unique identifier |
| INVESTIGATORS_STUDIES | INVESTIGATOR_ID | The investigator |
| INVESTIGATORS_STUDIES | INVESTIGATOR_TYPE_ID | If the investigator is the primary or sub on this study |
| INVESTIGATORS_STUDIES | SITE_ID | The site the investigator. |
| INVESTIGATORS_STUDIES | STUDY_MASTER_ID | the study |
| INVESTIGATORS_STUDIES | DATE_LOW | The start of actual activities for the investigator |
| INVESTIGATORS_STUDIES | DATE_HIGH | The end of actual activities for the investigator |

TABLE 37

Lab Process Types

| Table Name | Entity/Column Name | Description |
|---|---|---|
| LAB_PROCESS_TYPES | ENTITY | The type of lab process (Typical process steps are Specimen Collection, Specimen Accession, Specimen Separation etc) |
| LAB_PROCESS_TYPES | LAB_PROCESS_TYPE_ID | Unique identifier |
| LAB_PROCESS_TYPES | DESCRIPTION | Friendly name of identifier |
| LAB_PROCESS_TYPES | CODE | Code from the coding system |
| LAB_PROCESS_TYPES | CODE_SYSTEM | Code system of the code |
| LAB_PROCESS_TYPES | CODE_SYSTEM_VERSION | Version of the code system version of the code |

TABLE 38

Lab Process

| Table Name | Entity/Column Name | Description |
|---|---|---|
| LAB_PROCESSES | ENTITY | A process is performed on a specimen and its container or holder. Typical process steps are Specimen Collection, Specimen Accession, and Specimen Separation etc. The Process Step is intended to identify that the step has taken place but not record any value or the outcome. For instance, when Cold Agglutinins are discovered in the specimen during the processing of a CBC test the specimen is placed in a 37 degree wash for two hours. This observation would record that this had been performed. |
| LAB_PROCESSES | LAB_PROCESS_ID | Unique identifier |

TABLE 38-continued

Lab Process

| Table Name | Entity/Column Name | Description |
| --- | --- | --- |
| LAB_PROCESSES | LAB_PROCESS_TYPE_ID | The type of lab process (Typical process steps are Specimen Collection, Specimen Accession, Specimen Separation etc) |
| LAB_PROCESSES | SPECIMEN_ID | The specimen |
| LAB_PROCESSES | PLANNED_SPECIMEN_ID | The planned specimen |
| LAB_PROCESSES | DESCRIPTION | Text description of the process |
| LAB_PROCESSES | DATE_EFFECTIVE_LOW | When the process took place |
| LAB_PROCESSES | DATE_EFFECTIVE_HIGH | When the process took place |

TABLE 39

Lots

| Table Name | Entity/Column Name | Description |
| --- | --- | --- |
| LOTS | ENTITY | The lot for this instance. It identifies an amount of the product that has been produced or otherwise processed together. |
| LOTS | LOT_ID | Unique Identifier |
| LOTS | PRODUCT_ID | The product |
| LOTS | LOT_NUMBER | The lot number for this instance. |
| LOTS | EXPIRATION_LOW | When the lot expires |
| LOTS | EXPERATION_HIGH | When the lot expires |

TABLE 40

Method Types

| Table Name | Entity/Column Name | Description |
| --- | --- | --- |
| METHOD_TYPES | ENTITY | The means or technique used to ascertain the observation. In all observations the method is already partially specified by the observation type. In this case, the methodCode need not be used at all. Examples: Blood pressure measurement method: arterial puncture vs. sphygmomanometer (Riva-Rocci), sitting vs. supine position |
| METHOD_TYPES | METHOD_TYPE_ID | Unique identifier |
| METHOD_TYPES | DESCRIPTION | Friendly name of identifier |
| METHOD_TYPES | CODE | Code from the coding system |
| METHOD_TYPES | CODE_SYSTEM | Code system of the code |
| METHOD_TYPES | CODE_SYSTEM_VERSION | Version of the code system version of the code |

TABLE 41

Observation Result Types

| Table Name | Entity/Column Name | Description |
| --- | --- | --- |
| OBSERVATION_RESULT_CODE_TYPES | ENTITY | Results of the observation for coded values. Since coded systems can be post-coordinate, many codes could be present |

TABLE 42

Observation Types

| Table Name | Entity/Column Name | Description |
| --- | --- | --- |
| OBSERVATION_TYPES | ENTITY | The type of observation (e.g., type of lab test) |
| OBSERVATION_TYPES | OBSERVATION_TYPE_ID | Unique identifier |
| OBSERVATION_TYPES | DESCRIPTION | Friendly name of identifier |
| OBSERVATION_TYPES | CODE | Code from the coding system |
| OBSERVATION_TYPES | CODE_SYSTEM | Code system of the code |

TABLE 42-continued

Observation Types

| Table Name | Entity/Column Name | Description |
| --- | --- | --- |
| OBSERVATION_TYPES | CODE_SYSTEM_VERSION | Version of the code system version of the code |
| OBSERVATION_TYPES | DATATYPE_ID | The data type expected for the result of this observation. |

TABLE 43

Observations

| Table Name | Entity/Column Name | Description |
| --- | --- | --- |
| OBSERVATIONS | ENTITY | An actual activity that is intended to result in new information about a subject. A description of what was actually observed ("results" or "answers"). It may be a |
| OBSERVATIONS | OBSERVATION_ID | Unique identifier |
| OBSERVATIONS | METHOD_TYPE_ID | The means or technique used to ascertain the observation. In all observations the method is already partially specified by the observation type. In this case, the methodCode need not be used at all. Examples: Blood pressure measurement method: arterial puncture vs. sphygmomanometer (Riva-Rocci), sitting vs. supine position |
| OBSERVATIONS | INTERPRETATION_TYPE_ID | A qualitative interpretation of the observation. These interpretation codes are sometimes called "abnormal flags," however, the judgment of normalcy is just one of the interpretations, and is often not relevant. |
| OBSERVATIONS | ENCOUNTER_ID | The encounter where the observation occurred |
| OBSERVATIONS | TARGET_SITE_ID | The anatomical site or system that is the focus of the observation. Most observation target sites are implied by the observation type. For example, "heart murmur" always has the heart as target. If the subject of the Observation is something other than a human patient or animal, the attribute is used analogously to specify a structural landmark of the thing where the observation focuses. |
| OBSERVATIONS | DATATYPE_ID | Based on the data type certain fields will be populated. The data type examples include, coded, physical quantity, string, real |
| OBSERVATIONS | RESULT_REAL | Used when the data type is physical quantity, ratio or real. Result in a numeric value of the observation |
| OBSERVATIONS | RESULT_UNIT_ID | Used when the data type is physical quantity or ratio. The unit of measure of the result. The numeric value will be located in the result real. |
| OBSERVATIONS | RESULT_STRING | Used when the data type is string. The result of the observation |
| OBSERVATIONS | RESULT_DATE_LOW | Used when the data type is date. The result of the observation |
| OBSERVATIONS | RESULT_DATE_HIGH | Used when the data type is date. The result of the observation |
| OBSERVATIONS | RESULT_DENOM_REAL | Used when the data type is ratio. The numeric denominator result of the operation |
| OBSERVATIONS | RESULT_DENOM_UNIT_ID | Used when the data type is ration. The unit of measure of the denominator of the result of the observation |
| OBSERVATIONS | NEGATION | Explains the results are the opposite of what is stated |
| OBSERVATIONS | DESCRIPTION | Textual description of the observation |
| OBSERVATIONS | DATE_EFFECTIVE_HIGH | The date the observation was taken |
| OBSERVATIONS | DATE_EFFECTIVE_LOW | The date the observation was taken |

TABLE 43-continued

Observations

| Table Name | Entity/Column Name | Description |
|---|---|---|
| OBSERVATIONS | DURATION | The magnitude of the quantity measured in terms of the unit of the duration |
| OBSERVATIONS | DURATION_TIME_UNIT_ID | The unit of measure specified for the duration |
| OBSERVATIONS | AVAILABLE_DATE | The point in time at which information about this observation first became available to a system reproducing this observation. The availability date is metadata describing the record, not the observation. |
| OBSERVATIONS | SOURCE_ID | The id provided by the source document |
| OBSERVATIONS | BASELINE | Is this observation a baseline observation |
| OBSERVATIONS | OBSERVATION_TYPE_SOURCE | Original text of the type of observation (e.g., blood pressure test) |
| OBSERVATIONS | RESULT_SOURCE | Original text of the result |
| OBSERVATIONS | RESULT_SOURCE_UNIT | Original text of the result unit |
| OBSERVATIONS | RESEARCH_SUBJECT_ID | The subject of the observation |
| OBSERVATIONS | DATA_ENTERER | The person who entered the data |
| OBSERVATIONS | MODIFIED_REASON | The reason for the modification |
| OBSERVATIONS | MODIFIED_OBSERVATION_ID | The observation records that this records modifies |
| OBSERVATIONS | DEVICE_ID | The device that recorded the observation |
| OBSERVATIONS | INVESTIGATOR_ID | The investigator that recorded the observation |
| OBSERVATIONS | SERVICE_PROVIDER_ID | The service provided that recorded the observation |
| OBSERVATIONS | PLANNED_OBSERVATION_ID | The planned observation as specified in the protocol |
| OBSERVATIONS | TREATMENT_ID | The treatment that this observation is within |
| OBSERVATIONS | IS_CURRENT | If true the this record is the most current |

TABLE 44

Observation Cross Table Types

| Table Name | Entity/Column Name | Description |
|---|---|---|
| OBSERVATIONS_OBSERVATION_TYPES | ENTITY | The type of observation in coded values. Since coded systems can be post-coordinate, many codes could be present |
| OBSERVATIONS_OBSERVATION_TYPES | SEQ | The order the code appeared in the observation |

TABLE 45

Observation Specimen

| Table Name | Entity/Column Name | Description |
|---|---|---|
| OBSERVATIONS_SPECIMENS | ENTITY | One specimen can be the focus of many observations |
| OBSERVATIONS_SPECIMENS | CONDITION | The condition of the specimen. For example, if the specimen is cloudy, that could be analytically significant |

TABLE 46

Offset Type

| Table Name | Entity/Column Name | Description |
|---|---|---|
| OFFSET_BEFORE_AFTER_TYPES | ENTITY | A relationship in which the target planned activity takes place with a defined temporal relationship with respect to this planned activity. The relationship could be offset from the start or end of the target planned activity |

TABLE 47

Offset From Type

| Table Name | Entity/Column Name | Description |
|---|---|---|
| OFFSET_FROM_TYPES | ENTITY | The type of planned activity to offset from (e.g., treatment, procedure, supply, etc.) |
| OFFSET_FROM_TYPES | OFFSET_FROM_TYPE_ID | Unique identifier |
| OFFSET_FROM_TYPES | DESCRIPTION | Friendly name of the type |

TABLE 48

Organizer Types

| Table Name | Entity/Column Name | Description |
|---|---|---|
| ORGANIZER_TYPES | ENTITY | The type of organizer (e.g. domain, demographic, lab tests, etc.) |
| ORGANIZER_TYPES | ORGANIZER_TYPE_ID | Unique identifier |
| ORGANIZER_TYPES | DESCRIPTION | Friendly name of identifier |
| ORGANIZER_TYPES | CODE | Code from the coding system |

TABLE 48-continued

Organizer Types

| Table Name | Entity/Column Name | Description |
|---|---|---|
| ORGANIZER_TYPES | CODE_SYSTEM | Code system of the code |
| ORGANIZER_TYPES | CODE_SYSTEM_VERSION | Version of the code system version of the code |

TABLE 49

Organizers

| Table Name | Entity/Column Name | Description |
|---|---|---|
| ORGANIZERS | ENTITY | Used to group a set of planned or actual activities sharing a common context. Organizers can nest within other organizers - such as where a document is contained within a folder, or a folder is contained within an EHR extract |
| ORGANIZERS | ORGANIZER_ID | Unique identifier |
| ORGANIZERS | ORGANIZER_TYPE_ID | The type of organizer |
| ORGANIZERS | DESCRIPTION | The description of the organizer |
| ORGANIZERS | SOURCE_ID | The identifier of the organizer from the source document |

TABLE 50

Organizer Actions

| Table Name | Entity/Column Name | Description |
|---|---|---|
| ORGANIZERS_ACTIONS | ENTITY | Link many planned or actual activities in to one organizer |
| ORGANIZERS_ACTIONS | ORGANIZER_ACTION_ID | Unique identifier |
| ORGANIZERS_ACTIONS | ORGANIZER_ID | The organizer |
| ORGANIZERS_ACTIONS | ACTION_TYPE_ID | A supply, substance administration, procedure or observation. |

TABLE 51

Planned Administration

| Table Name | Entity/Column Name | Description |
|---|---|---|
| PLANNED_ADMINISTRATIONS | ENTITY | A planned type of procedure that involves a performer introducing or otherwise applying a product into or to the experimental unit. For purposes of this definition, photons and other models of radiation or light energy are considered substances. Substances may also include living entities such as live |

TABLE 51-continued

| | Planned Administration | |
|---|---|---|
| Table Name | Entity/Column Name | Description |
| | | virus vaccines and other materials containing infectious agents, e.g., saliva, blood products, etc. |
| PLANNED_ADMINISTRATIONS | OFFSET_OBSERVATION_ID | Offset from a target observation |

TABLE 52

| | Planned Encounter | |
|---|---|---|
| Table Name | Entity/Column Name | Description |
| PLANNED_ENCOUNTERS | ENTITY | A planned interaction between an experimental unit and an investigator for the purpose of providing study related services. |
| PLANNED_ENCOUNTERS | PLANNED_ENCOUNTER_ID | Unique identifier |
| PLANNED_ENCOUNTERS | ENCOUNTER_TYPE_ID | The type of encounter (e.g., visit, journal entry). |
| PLANNED_ENCOUNTERS | DESCRIPTION | Textual description of the encounter |
| PLANNED_ENCOUNTERS | DURATION | The magnitude of the quantity measured in terms of the unit of the duration |
| PLANNED_ENCOUNTERS | DURATION_TIME_UNIT_ID | The unit of measure specified for the duration |
| PLANNED_ENCOUNTERS | OFFSET | The magnitude of the quantity measured in terms of the unit of the offset from the target planned activity |
| PLANNED_ENCOUNTERS | OFFSET_TIME_UNIT_ID | The unit of measure specified for the offset |
| PLANNED_ENCOUNTERS | OFFSET_BEFORE_AFTER_TYPE_ID | A relationship in which the target planned activity takes place with a defined temporal relationship with respect to this planned activity. The relationship could be offset from the start or end of the target planned activity |
| PLANNED_ENCOUNTERS | OFFSET_FROM_TYPE_ID | The type of planned activity to offset from (e.g., treatment, procedure, supply, etc.) |
| PLANNED_ENCOUNTERS | OFFSET_TREATMENT_ID | Offset from a target treatment |
| PLANNED_ENCOUNTERS | OFFSET_SUPPLY_ID | Offset from a target supply |
| PLANNED_ENCOUNTERS | OFFSET_PROCEDURE_ID | Offset from a target procedure |
| PLANNED_ENCOUNTERS | OFFSET_OBSERVATION_ID | Offset from a target observation |
| PLANNED_ENCOUNTERS | OFFSET_ADMINISTRATION_ID | Offset from a target substance administration |
| PLANNED_ENCOUNTERS | OFFSET_ENCOUNTER_ID | Offset from a target encounter |
| PLANNED_ENCOUNTERS | SOURCE_ID | The id provided by the source document |
| PLANNED_ENCOUNTERS | TREATMENT_ID | The treatment that this encounter is within |

TABLE 53

| | Planned Observation Cross Table Types | |
|---|---|---|
| Table Name | Entity/Column Name | Description |
| PLANNED_OBS_OBS_TYPES | ENTITY | The type of observation in coded values. Since coded systems can be post-coordinate, many codes could be present |
| PLANNED_OBS_OBS_TYPES | SEQ | The order the code appeared in the observation |

TABLE 54

| Table Name | Entity/Column Name | Description |
|---|---|---|
| | Planned Observation | |
| PLANNED_OBSERVATIONS | ENTITY | A planned activity that is intended to result in new information about a subject. A description of what was actually observed ("results" or "answers"). It may be a |
| PLANNED_OBSERVATIONS | PLANNED_OBSERVATION_ID | Unique identifier |
| PLANNED_OBSERVATIONS | OBSERVATION_TYPE_ID | The type of observation (e.g., lab test) |
| PLANNED_OBSERVATIONS | METHOD_TYPE_ID | The means or technique used to ascertain the observation. In all observations the method is already partially specified by the observation type. In this case, the methodCode need not be used at all. Examples: Blood pressure measurement method: arterial puncture vs. sphygmomanometer (Riva-Rocci), sitting vs. supine position |
| PLANNED_OBSERVATIONS | INTERPRETATION_TYPE_ID | A qualitative interpretation of the observation. These interpretation codes are sometimes called "abnormal flags," however, the judgment of normalcy is just one of the interpretations, and is often not relevant. |
| PLANNED_OBSERVATIONS | PLANNED_ENCOUNTER_ID | Planned encounter where the observation is within |
| PLANNED_OBSERVATIONS | TARGET_SITE_ID | The anatomical site or system that is the focus of the observation. Most observation target sites are implied by the observation type. For example, "heart murmur" always has the heart as target. If the subject of the Observation is something other than a human patient or animal, the attribute is used analogously to specify a structural landmark of the thing where the observation focuses. |
| PLANNED_OBSERVATIONS | DATATYPE_ID | Based on the data type certain fields will be populated. The data type examples include, coded, physical quantity, string, real |
| PLANNED_OBSERVATIONS | NEGATION | Specifies this observation should not occur |
| PLANNED_OBSERVATIONS | DESCRIPTION | Textual description of the observation |
| PLANNED_OBSERVATIONS | DURATION | The magnitude of the quantity measured in terms of the unit of the duration |
| PLANNED_OBSERVATIONS | DURATION_TIME_UNIT_ID | The unit of measure specified for the duration |
| PLANNED_OBSERVATIONS | OFFSET | The magnitude of the quantity measured in terms of the unit of the offset from the target planned activity |
| PLANNED_OBSERVATIONS | OFFSET_TIME_UNIT_ID | The unit of measure specified for the offset |
| PLANNED_OBSERVATIONS | OFFSET_BEFORE_AFTER_TYPE_ID | A relationship in which the target planned activity takes place with a defined temporal relationship with respect to this planned activity. The relationship could be offset from the start or end of the target planned activity |
| PLANNED_OBSERVATIONS | OFFSET_FROM_TYPE_ID | The type of planned activity to offset from (e.g., treatment, procedure, supply, etc.) |
| PLANNED_OBSERVATIONS | OFFSET_SUPPLY_ID | Offset from a target supply |
| PLANNED_OBSERVATIONS | OFFSET_TREATMENT_ID | Offset from a target treatment |
| PLANNED_OBSERVATIONS | OFFSET_PROCEDURE_ID | Offset from a target procedure |
| PLANNED_OBSERVATIONS | OFFSET_OBSERVATION_ID | Offset from a target observation |
| PLANNED_OBSERVATIONS | OFFSET_ADMINISTRATION_ID | Offset from a target substance administration |
| PLANNED_OBSERVATIONS | OFFSET_ENCOUNTER_ID | Offset from a target encounter |
| PLANNED_OBSERVATIONS | SOURCE_ID | The id provided by the source document |
| PLANNED_OBSERVATIONS | TREATMENT_ID | The treatment that this encounter is within |

TABLE 55

| Table Name | Entity/Column Name | Description |
|---|---|---|
| | Planned Procedure | |
| PLANNED_PROCEDURES | ENTITY | A planned activity whose immediate and primary outcome (post-condition) is the alteration of the physical condition of the subject. A procedure does not comprise all planned activities of whose intent is intervention. Whether the bodily alteration is appreciated or intended as beneficial to the subject is likewise irrelevant. Taking an x-ray image may sometimes be called "procedure," but it is not a procedure, for an x-ray image is not done to alter the physical condition of the body. The X-Ray is a substance administration |
| PLANNED_PROCEDURES | PLANNED_PROCEDURE_ID | Unique identifier |
| PLANNED_PROCEDURES | PROCEDURE_TYPE_ID | The type of procedure |
| PLANNED_PROCEDURES | PRODUCT_ID | The product applied in the procedure |
| PLANNED_PROCEDURES | METHOD_TYPE_ID | The means or technique used to perform the procedure. For any Procedure there may be several different methods to achieve by and large the same result, but may be important to know when interpreting a report more thoroughly (e.g., cholecystectomy: open vs. laparoscopic). |
| PLANNED_PROCEDURES | PLANNED_ENCOUNTER_ID | Planned encounter where the observation is within |
| PLANNED_PROCEDURES | APPROACH_SITE_ID | The anatomical site or system through which the procedure reaches its target. For example: An arteria pulmonalis catheter targets a pulmonary artery, but the approach site is typically the vena carotis interna at the neck or the vena subclavia at the fossa subclavia. |
| PLANNED_PROCEDURES | TARGET_SITE_ID | The anatomical site or system that is the focus of the procedure. For example: An arteria pulmonalis catheter targets a pulmonary artery, but the approach site is typically the vena carotis interna at the neck or the vena subclavia at the fossa subclavia. |
| PLANNED_PROCEDURES | NEGATION | Specifies this procedure should not occur |
| PLANNED_PROCEDURES | DESCRIPTION | Textual description of the procedure |
| PLANNED_PROCEDURES | DURATION | The magnitude of the quantity measured in terms of the unit of the duration |
| PLANNED_PROCEDURES | DURATION_TIME_UNIT_ID | The unit of measure specified for the duration |
| PLANNED_PROCEDURES | OFFSET | The magnitude of the quantity measured in terms of the unit of the offset from the target planned activity |
| PLANNED_PROCEDURES | OFFSET_TIME_UNIT_ID | The unit of measure specified for the offset |
| PLANNED_PROCEDURES | OFFSET_BEFORE_AFTER_TYPE_ID | A relationship in which the target planned activity takes place with a defined temporal relationship with respect to this planned activity. The relationship could be offset from the start or end of the target planned activity |
| PLANNED_PROCEDURES | OFFSET_FROM_TYPE_ID | The type of planned activity to offset from (e.g., treatment, procedure, supply, etc.) |
| PLANNED_PROCEDURES | OFFSET_SUPPLY_ID | Offset from a target supply |
| PLANNED_PROCEDURES | OFFSET_TREATMENT_ID | Offset from a target treatment |
| PLANNED_PROCEDURES | OFFSET_PROCEDURE_ID | Offset from a target procedure |
| PLANNED_PROCEDURES | OFFSET_OBSERVATION_ID | Offset from a target observation |
| PLANNED_PROCEDURES | OFFSET_ADMINISTRATION_ID | Offset from a target substance administration |

TABLE 55-continued

Planned Procedure

| Table Name | Entity/Column Name | Description |
| --- | --- | --- |
| PLANNED_PROCEDURES | OFFSET_ENCOUNTER_ID | Offset from a target encounter |
| PLANNED_PROCEDURES | SOURCE_ID | The id provided by the source document |
| PLANNED_PROCEDURES | TREATMENT_ID | The treatment that this encounter is within |

TABLE 56

Planned Research Subject

| Table Name | Entity/Column Name | Description |
| --- | --- | --- |
| PLANNED_RESEARCH_SUBJECTS | ENTITY | The experimental unit is the physical entity which is the primary unit of interest in a study. In an interventional study, the experimental unit is assigned to an intervention. The experimental unit is also the unit of primary statistical analysis. Commonly the individual subject (animal, person or product) is the experimental unit. Different experimental units must be capable of receiving different experimental interventions. Accordingly if all pigs in a pen receive the same intervention in their feed, and the primary observations and analyses of interest are associated with the entire pen (e.g., total feed consumed, total weight of all pigs combined), then the pen of pigs rather than the individual animal is the experimental unit. This means that the statistical analysis may be incorrect if it is assumed that the pig is the experimental unit. In this case the statistical analysis should normally be done using the mean of all the pigs in the pen. An example of when the experimental unit is a product would be product stress test or product performance studies. |
| PLANNED_RESEARCH_SUBJECTS | PLANNED_RESEARCH_SUBJECT_ID | Unique identifier |
| PLANNED_RESEARCH_SUBJECTS | STUDY_SITE_ID | Site where the planned subject will be located |
| PLANNED_RESEARCH_SUBJECTS | SPECIES_ID | The type of species |
| PLANNED_RESEARCH_SUBJECTS | PRODUCT_ID | The product that is the subject |
| PLANNED_RESEARCH_SUBJECTS | RESEARCH_SUBJECT_TYPE_ID | The type of research subject (e.g., person, animal, virus, specimen, group, part of organism, etc.) |
| PLANNED_RESEARCH_SUBJECTS | QUANTITY | The total amount of research subject that will be of this type |
| PLANNED_RESEARCH_SUBJECTS | SOURCE_ID | The unique identifier in the source document |

TABLE 57

Planned Specimen

| Table Name | Entity/Column Name | Description |
|---|---|---|
| PLANNED_SPECIMENS | ENTITY | The type of specimen that is planned to be collected |

TABLE 58

Planned Subject Condition

| Table Name | Entity/Column Name | Description |
|---|---|---|
| PLANNED_SUBJECT_CONDITIONS | ENTITY | Experimental units are sometimes segregated based on certain criteria. For example, site 1 might enroll 8 males and 12 females, where site 2 enrolls 12 males and 8 females. |
| PLANNED_SUBJECT_CONDITIONS | PLANNED_SUBJECT_CONDITION_ID | Unique identifier |
| PLANNED_SUBJECT_CONDITIONS | PLANNED_RESEARCH_SUBJECT_ID | The planned research subject |
| PLANNED_SUBJECT_CONDITIONS | OBSERVATION_TYPE_ID | The condition |
| PLANNED_SUBJECT_CONDITIONS | DATATYPE_ID | Based on the data type certain fields will be populated. The data type examples include, coded, physical quantity, string, real |
| PLANNED_SUBJECT_CONDITIONS | CONDITION_REAL | Used when the data type is physical quantity, ratio or real. Result in a numeric value of the observation |
| PLANNED_SUBJECT_CONDITIONS | CONDITION_UNIT_ID | Used when the data type is physical quantity or ratio. The unit of measure of the result. The numeric value will be located in the result_real. |
| PLANNED_SUBJECT_CONDITIONS | CONDITION_STRING | Used when the data type is string. The result of the observation |
| PLANNED_SUBJECT_CONDITIONS | CONDITION_DATE_LOW | Used when the data type is date. The result of the observation |
| PLANNED_SUBJECT_CONDITIONS | CONDITION_DATE_HIGH | Used when the data type is date. The result of the observation |
| PLANNED_SUBJECT_CONDITIONS | CONDITION_DENOM_REAL | Used when the data type is ratio. The numeric denominator result of the operation |
| PLANNED_SUBJECT_CONDITIONS | CONDITION_DENOM_UNIT_ID | Used when the data type is ration. The unit of measure of the denominator of the result of the observation |
| PLANNED_SUBJECT_CONDITIONS | NEGATION | Explains the results are the opposite of what is stated |
| PLANNED_SUBJECT_CONDITIONS | DESCRIPTION | Textual description of the observation |

TABLE 59

Planned Subject

| Table Name | Entity/Column Name | Description |
|---|---|---|
| PLANNED_SUBJECTS_SUBJECTS | ENTITY | The relationship between subjects. e.g., members in a group or people of the specimen |

TABLE 60

Planned Supplies

| Table Name | Entity/Column Name | Description |
|---|---|---|
| PLANNED_SUPPLIES | ENTITY | Planned provision of a material by an investigator to the experimental unit. The precise identification of the product (route, dosage form, serial numbers, etc.) is important. Most of the detailed infoimation about the Supply should be represented using by the product. |
| PLANNED_SUPPLIES | PLANNED_SUPPLY_ID | Unique id |

TABLE 60-continued

Planned Supplies

| Table Name | Entity/Column Name | Description |
| --- | --- | --- |
| PLANNED_SUPPLIES | SUPPLY_TYPE_ID | The type of supply |
| PLANNED_SUPPLIES | PRODUCT_ID | The product that is being supplied |
| PLANNED_SUPPLIES | PLANNED_ENCOUNTER_ID | The encounter where the supply occurs |
| PLANNED_SUPPLIES | DESCRIPTION | Textual description of the supply |
| PLANNED_SUPPLIES | QUANTITY | The amount of product that is to be supplied. |
| PLANNED_SUPPLIES | QUANTITY_UNIT_ID | The unit of measure specified for the quantity |
| PLANNED_SUPPLIES | EXPECTED_USE_HIGH | The period time over which the supplied product is expected to be used. |
| PLANNED_SUPPLIES | EXPECTED_USE_LOW | The period time over which the supplied product is expected to be used. |
| PLANNED_SUPPLIES | EXPECTED_USE_UNIT_ID | The unit of measure specified for the expected use |
| PLANNED_SUPPLIES | OFFSET | The magnitude of the quantity measured in terms of the unit of the offset from the target planned activity |
| PLANNED_SUPPLIES | OFFSET_TIME_UNIT_ID | The unit of measure specified for the offset |
| PLANNED_SUPPLIES | OFFSET_BEFORE_AFTER_TYPE_ID | A relationship in which the target planned activity takes place with a defined temporal relationship with respect to this planned activity. The relationship could be offset from the start or end of the target planned activity |
| PLANNED_SUPPLIES | OFFSET_FROM_TYPE_ID | The type of activity to offset from (e.g., treatment, procedure, supply, etc.) |
| PLANNED_SUPPLIES | OFFSET_TREATMENT_ID | Offset from a target treatment |
| PLANNED_SUPPLIES | OFFSET_SUPPLY_ID | Offset from a target supply |
| PLANNED_SUPPLIES | OFFSET_PROCEDURE_ID | Offset from a target procedure |
| PLANNED_SUPPLIES | OFFSET_OBSERVATION_ID | Offset from a target observation |
| PLANNED_SUPPLIES | OFFSET_ADMINISTRATION_ID | Offset from a target substance administration |
| PLANNED_SUPPLIES | OFFSET_ENCOUNTER_ID | Offset from a target encounter |
| PLANNED_SUPPLIES | SOURCE_ID | The id provided by the source document |
| PLANNED_SUPPLIES | TREATMENT_ID | The treatment that this encounter is within |

TABLE 61

Planned Subject Condition Observation Type

| Table Name | Entity/Column Name | Description |
| --- | --- | --- |
| PLND_SUBJCT_COND_OBS_TYPES | ENTITY | The type of observation in coded values. Since coded systems can be post-coordinate, many codes could be present |
| PLND_SUBJCT_COND_OBS_TYPES | SEQ | The order the code appeared in the observation |

TABLE 62

Planned Subject Condition Result Type

| Table Name | Entity/Column Name | Description |
| --- | --- | --- |
| PLND_SUBJCT_COND_RESULT_TYPES | ENTITY | Results of the observation for coded values. Since coded systems can be post-coordinate, many codes could be present |

TABLE 63

Procedure Type

| Table Name | Entity/Column Name | Description |
| --- | --- | --- |
| PROCEDURE_TYPES | ENTITY | The type of procedure |
| PROCEDURE_TYPES | PROCEDURE_TYPE_ID | Unique identifier |
| PROCEDURE_TYPES | DESCRIPTION | Friendly name of identifier |
| PROCEDURE_TYPES | CODE | Code from the coding system |
| PROCEDURE_TYPES | CODE_SYSTEM | Code system of the code |
| PROCEDURE_TYPES | CODE_SYSTEM_VERSION | Version of the code system version of the code |

TABLE 64

Procedures

| Table Name | Entity/Column Name | Description |
|---|---|---|
| PROCEDURES | ENTITY | An actual activity whose immediate and primary outcome (post-condition) is the alteration of the physical condition of the subject. A procedure does not comprise all actual activities of whose intent is intervention. Whether the bodily alteration is appreciated or intended as beneficial to the subject is likewise irrelevant. Taking an x-ray image may sometimes be called "procedure," but it is not a procedure, for an x-ray image is not done to alter the physical condition of the body. The X-Ray is a substance administration |
| PROCEDURES | PROCEDURE_ID | Unique identifier |
| PROCEDURES | PROCEDURE_TYPE_ID | The type of procedure |
| PROCEDURES | PRODUCT_ID | The product applied in the procedure |
| PROCEDURES | METHOD_TYPE_ID | The means or technique used to perform the procedure. For any Procedure there may be several different methods to achieve by and large the same result, but may be important to know when interpreting a report more thoroughly (e.g., cholecystectomy: open vs. laparoscopic). |
| PROCEDURES | ENCOUNTER_ID | The encounter where the procedure occurred |
| PROCEDURES | APPROACH_SITE_ID | The anatomical site or system through which the procedure reaches its target. For example: An arteria pulmonalis catheter targets a pulmonary artery, but the approach site is typically the vena carotis interna at the neck or the vena subclavia at the fossa subclavia. |
| PROCEDURES | TARGET_SITE_ID | The anatomical site or system that is the focus of the procedure. For example: An arteria pulmonalis catheter targets a pulmonary artery, but the approach site is typically the vena carotis interna at the neck or the vena subclavia at the fossa subclavia. |
| PROCEDURES | NEGATION | That the procedure did not occur |
| PROCEDURES | DESCRIPTION | Textual description of the procedure |
| PROCEDURES | DATE_EFFECTIVE_HIGH | The date the procedure occurred |
| PROCEDURES | DATE_EFFECTIVE_LOW | The date the procedure occurred |
| PROCEDURES | AVAILABLE_DATE | The point in time at which information about this procedure first became available to a system reproducing this administration. The availability date is metadata describing the record, not the procedure. |
| PROCEDURES | DURATION | The magnitude of the quantity measured in terms of the unit of the duration |
| PROCEDURES | DURATION_TIME_UNIT_ID | The unit of measure specified for the duration |
| PROCEDURES | SOURCE_ID | The id provided by the source document |
| PROCEDURES | RESEARCH_SUBJECT_ID | The subject of the procedure |
| PROCEDURES | DATE_ENTERER | The person who entered the data |
| PROCEDURES | MODIFIED_REASON | The reason for the modification |
| PROCEDURES | MODIFIED_PROCEDURE_ID | The procedure records that this records modifies |
| PROCEDURES | DEVICE_ID | The device that recorded the procedure |
| PROCEDURES | INVESTIGATOR_ID | The investigator that recorded the procedure |
| PROCEDURES | SERVICE_PROVIDER_ID | The service provided that recorded the procedure |
| PROCEDURES | PLANNED_PROCEDURE_ID | The planned procedure as specified in the protocol |
| PROCEDURES | TREATMENT_ID | The treatment that this procedure is within |
| PROCEDURES | IS_CURRENT | If true the this record is the most current |

TABLE 65

Product Instance

| Table Name | Entity/Column Name | Description |
|---|---|---|
| PRODUCT_INSTANCE | ENTITY | Information for a particular product instance, or amount of the product. |
| PRODUCT_INSTANCE | PRODUCT_INSTANCE_ID | Unique identifier |
| PRODUCT_INSTANCE | PRODUCT_ID | The product |
| PRODUCT_INSTANCE | LOT_ID | The lot |

TABLE 66

Product Part

| Table Name | Entity/Column Name | Description |
|---|---|---|
| PRODUCT_PARTS | ENTITY | Products could be combination products or the parts could be of interest |

TABLE 66-continued

Product Part

| Table Name | Entity/Column Name | Description |
| --- | --- | --- |
| PRODUCT_PARTS | PRODUCT_ID | Product identifier |
| PRODUCT_PARTS | PARENT_PRODUCT_ID | The product of whom this product is a part of |
| PRODUCT_PARTS | QUANTITY | The number of this product in the parent product |
| PRODUCT_PARTS | UNIT_ID | Unit of measure of the quantity of products |

TABLE 67

Product Types

| Table Name | Entity/Column Name | Description |
| --- | --- | --- |
| PRODUCT_TYPES | ENTITY | The type of product |
| PRODUCT_TYPES | PRODUCT_TYPE_ID | Unique identifier |
| PRODUCT_TYPES | DESCRIPTION | Friendly name of identifier |
| PRODUCT_TYPES | CODE | Code from the coding system |
| PRODUCT_TYPES | CODE_SYSTEM | Code system of the code |
| PRODUCT_TYPES | CODE_SYSTEM_VERSION | Version of the code system version of the code |

TABLE 68

Product

| Table Name | Entity/Column Name | Description |
| --- | --- | --- |
| PRODUCTS | ENTITY | A product, like a device or pill, could be the experimental unit of the study or the product used to extract the specimen. |
| PRODUCTS | PRODUCT_ID | Unique identifier |
| PRODUCTS | PRODUCT_TYPE_ID | The kind of product |
| PRODUCTS | PROPRIETARY_NAME | The name of the product as per the manufacturer |
| PRODUCTS | DOSAGE_FORM_ID | The dosage form (e.g., tablet) of the product |
| PRODUCTS | MODEL_NUMBER | The product identifier as per the manufacturer |
| PRODUCTS | SOFTWARE_NAME | The software name and version of the product |

TABLE 69

Qualification Type

| Table Name | Entity/Column Name | Description |
| --- | --- | --- |
| QUALIFICATION_TYPES | ENTITY | The type of qualifications (e.g., MD, board certifications, etc.) |
| QUALIFICATION_TYPES | QUALIFICATION_TYPE_ID | Unique identifier |
| QUALIFICATION_TYPES | DESCRIPTION | Friendly name of identifier |
| QUALIFICATION_TYPES | CODE | Code from the coding system |
| QUALIFICATION_TYPES | CODE_SYSTEM | Code system of the code |
| QUALIFICATION_TYPES | CODE_SYSTEM_VERSION | Version of the code system version of the code |

TABLE 70

Qualification

| Table Name | Entity/Column Name | Description |
| --- | --- | --- |
| QUALIFICATIONS | ENTITY | A skill, achievement, etc, that demonstrates that a person capable or suitable to do a job etc. |
| QUALIFICATIONS | QUALIFICATION_ID | Unique identifier |
| QUALIFICATIONS | INVESTIGATOR_ID | Investigator |
| QUALIFICATIONS | QUALIFICATION_TYPE_ID | The type of qualifications (e.g., MD, board certifications, etc.) |
| QUALIFICATIONS | DATE_HIGH | The end date of the qualification |
| QUALIFICATIONS | DATE_LOW | The start date of the qualification |
| QUALIFICATIONS | ISSUER_NAME | The name of the issuing party of the qualification |
| QUALIFICATIONS | ISSUER_ADDRESS1 | The address of the issuing party of the qualification |
| QUALIFICATIONS | ISSUER_ADDRESS2 | The address of the issuing party of the qualification |
| QUALIFICATIONS | ISSUER_CITY | The city of the issuing party of the qualification |
| QUALIFICATIONS | ISSUER_STATE | The state of the issuing party of the qualification |
| QUALIFICATIONS | ISSUER_COUNTRY | The country of the issuing party of the qualification |

TABLE 71

Quantity Units

| Table Name | Entity/Column Name | Description |
| --- | --- | --- |
| QUANTITY_UNITS | ENTITY | A dimensioned quantity expressing the result of measuring |
| QUANTITY_UNITS | QUANTITY_UNIT_ID | Unique identifier |
| QUANTITY_UNITS | DESCRIPTION | Friendly name of identifier |
| QUANTITY_UNITS | CODE | Code from the coding system |
| QUANTITY_UNITS | CODE_SYSTEM | Code system of the code |
| QUANTITY_UNITS | CODE_SYSTEM_VERSION | Version of the code system version of the code |

TABLE 72

Race

| Table Name | Entity/Column Name | Description |
|---|---|---|
| RACES | ENTITY | The race |

TABLE 73

Reference Criteria Observation Types

| Table Name | Entity/Column Name | Description |
|---|---|---|
| REF_CRITERIA_OBS_TYPES | ENTITY | The type of observation in coded values. Since coded systems can be post-coordinate, many codes could be present |
| REF_CRITERIA_OBS_TYPES | SEQ | The order the code appeared in the observation |

TABLE 74

Reference Observation High Type

| Table Name | Entity/Column Name | Description |
|---|---|---|
| REFERENCE_OBS_RES_HIGH_TYPES | ENTITY | The type of observation in coded values. Since coded systems can be post-coordinate, many codes could be present |
| REFERENCE_OBSERVATION_TYPES | SEQ | The order the code appeared in the observation |

TABLE 75

Reference Observation Low Type

| Table Name | Entity/Column Name | Description |
|---|---|---|
| REFERENCE_OBS_RES_LOW_TYPES | ENTITY | The type of observation in coded values. Since coded systems can be post-coordinate, many codes could be present |
| REFERENCE_OBSERVATION_TYPES | SEQ | The order the code appeared in the observation |

TABLE 76

Reference Observation Types

| Table Name | Entity/Column Name | Description |
|---|---|---|
| REFERENCE_OBSERVATION_TYPES | ENTITY | The type of observation in coded values. Since coded systems can be post-coordinate, many codes could be present |
| REFERENCE_OBSERVATION_TYPES | SEQ | The order the code appeared in the observation |

TABLE 77

Reference Range Criteria

| Table Name | Entity/Column Name | Description |
|---|---|---|
| REFERENCE_RANGE_CRITERIA | ENTITY | The criteria uses to determine is the reference range is appropriate |
| REFERENCE_RANGE_CRITERIA | OBSERVATION CRITERION_ID | Unique identifier |
| REFERENCE_RANGE_CRITERIA | REFERENCE_CRITERION_TYPE_ID | Should this be observation type |
| REFERENCE_RANGE_CRITERIA | REFERENCE_RANGE_ID | The reference range |
| REFERENCE_RANGE_CRITERIA | PARENT_ID | When the criteria is complex, the parent criteria |
| REFERENCE_RANGE_CRITERIA | CONJUNCTION_TYPE_ID | The logical conjunction of the criteria among all the rules (e.g., and, or, exclusive-or). |
| REFERENCE_RANGE_CRITERIA | DATATYPE_ID | Based on the data type certain fields will be populated. The data type examples include, coded, physical quantity, string, real |
| REFERENCE_RANGE_CRITERIA | RESULT_REAL | Used when the data type is physical quantity, ratio or real. Result in a numeric value of the observation |

TABLE 77-continued

Reference Range Criteria

| Table Name | Entity/Column Name | Description |
|---|---|---|
| REFERENCE_RANGE_CRITERIA | RESULT_UNIT_ID | Used when the data type is physical quantity or ratio. The unit of measure of the result. The numeric value will be located in the result_real. The low end of the range. |
| REFERENCE_RANGE_CRITERIA | RESULT_STRING | Used when the data type is string. The result of the observation |
| REFERENCE_RANGE_CRITERIA | RESULT_DATE_LOW | Used when the data type is date. The result of the observation |
| REFERENCE_RANGE_CRITERIA | RESULT_DATE_HIGH | Used when the data type is date. The result of the observation |
| REFERENCE_RANGE_CRITERIA | RESULT_DENOM_REAL | Used when the data type is ratio. The numeric denominator result of the operation |
| REFERENCE_RANGE_CRITERIA | RESULT_DENOM_UNIT_ID | Used when the data type is ration. The unit of measure of the denominator of the result of the observation |
| REFERENCE_RANGE_CRITERIA | NEGATION | Explains the results are the opposite of what is stated |
| REFERENCE_RANGE_CRITERIA | SEQ | The order of this criteria within the parent |

TABLE 78

Reference Range Types

| Table Name | Entity/Column Name | Description |
|---|---|---|
| REFERENCE_RANGE_TYPES | ENTITY | Could be possible values (e.g., a thermometer can produce values from 92-108), linear range (e.g., a thermometer is accurate from 97-105), normal range (e.g., a healthy patient would be in the range of 98-99) |
| REFERENCE_RANGE_TYPES | REFERENCE_RANGE_TYPE_ID | Unique identifier |
| REFERENCE_RANGE_TYPES | DESCRIPTION | Friendly name of identifier |
| REFERENCE_RANGE_TYPES | CODE | Code from the coding system |
| REFERENCE_RANGE_TYPES | CODE_SYSTEM | Code system of the code |
| REFERENCE_RANGE_TYPES | CODE_SYSTEM_VERSION | Version of the code system version of the code |

TABLE 79

Reference Range

| Table Name | Entity/Column Name | Description |
|---|---|---|
| REFERENCE_RANGES | ENTITY | Reference ranges are essentially descriptors of a result values assumed to be "normal", "abnormal", or "critical." Those can vary by sex, age, or any other criterion. |
| REFERENCE_RANGES | REFERENCE_RANGE_ID | Unique Identifier |
| REFERENCE_RANGES | OBSERVATION_ID | The observation where the range applies to |
| REFERENCE_RANGES | INTERPRETATION_TYPE_ID | A qualitative interpretation of the observation. These interpretation codes are sometimes called "abnormal flags," however, the judgment of normalcy is just one of the interpretations, and is often not relevant. |
| REFERENCE_RANGES | RESULT_LOW_REAL | Used when the data type is physical quantity, ratio or real. Result in a numeric value of the observation. The low end of the range. |
| REFERENCE_RANGES | RESULT_LOW_UNIT_ID | Used when the data type is physical quantity or ratio. The unit of measure of the result. The numeric value will be located in the result_real. The low end of the range. |
| REFERENCE_RANGES | RESULT_LOW_STRING | Used when the data type is string. The result of the observation. The low end of the range |
| REFERENCE_RANGES | RESULT_LOW_DATE_LOW | Used when the data type is date. The result of the observation. The low end of the range. |
| REFERENCE_RANGES | RESULT_LOW_DATE_HIGH | Used when the data type is date. The result of the observation. The low end of the range. |
| REFERENCE_RANGES | RESULT_LOW_DENOM_REAL | Used when the data type is ratio. The numeric denominator result of the operation. The low end of the range |
| REFERENCE_RANGES | RESULT_LOW_DENOM_UNIT_ID | Used when the data type is ration. The unit of measure of the denominator of the result of the observation. The low end of the range. |
| REFERENCE_RANGES | RESULT_HIGH_REAL | Used when the data type is physical quantity, ratio or real. Result in a numeric value of the observation. The high end of the range. |
| REFERENCE_RANGES | RESULT_HIGH_UNIT_ID | Used when the data type is physical quantity or ratio. The unit of measure of the result. The numeric value will be located in the result_real. The low end of the range. |
| REFERENCE_RANGES | RESULT_HIGH_STRING | Used when the data type is string. The result of the observation. The high end of the range |
| REFERENCE_RANGES | RESULT_HIGH_DATE_LOW | Used when the data type is date. The result of the observation. The low high of the range. |
| REFERENCE_RANGES | RESULT_HIGH_DATE_HIGH | Used when the data type is date. The result of the observation. The low high of the range. |

TABLE 79-continued

Reference Range

| Table Name | Entity/Column Name | Description |
|---|---|---|
| REFERENCE_RANGES | RESULT_HIGH_DENOM_REAL | Used when the data type is ratio. The numeric denominator result of the operation. The high end of the range |
| REFERENCE_RANGES | RESULT_HIGH_DENOM_UNIT_ID | Used when the data type is ration. The unit of measure of the denominator of the result of the observation. The high end of the range. |
| REFERENCE_RANGES | DESCRIPTION | The textual description of the range |
| REFERENCE_RANGES | NEGATION | Specifies the opposite. |
| REFERENCE_RANGES | RESULT_LOW_REAL_SOURCE | The source text of the low end of the range |
| REFERENCE_RANGES | RESULT_HIGH_REAL_SOURCE | The source text of the high end of the range |

TABLE 80

Reference Result Code Type

| Table Name | Entity/Column Name | Description |
|---|---|---|
| REFERENCE_RESULT_CODE_TYPES | ENTITY | Results of the observation for coded values. Since coded systems can be post-coordinate, many codes could be present |

TABLE 81

Reports

| Table Name | Entity/Column Name | Description |
|---|---|---|
| REPORTS | ENTITY | The safety report |
| REPORTS | REPORT_ID | Unique identifier |
| REPORTS | COMPLETED | When the report was complete |
| REPORTS | AVAILABLE | When the report was made available |

TABLE 82

Report Documents

| Table Name | Entity/Column Name | Description |
|---|---|---|
| REPORTS_DOCUMENTS | ENTITY | There could be many documents associated to a report |

TABLE 83

Research Subject Identifiers

| Table Name | Entity/Column Name | Description |
|---|---|---|
| RESEARCH_SUBJECT_IDENTIFIERS | ENTITY | Other identifiers of the subject |
| RESEARCH_SUBJECT_IDENTIFIERS | RESEARCH_SUBJECT_ID | Subject |
| RESEARCH_SUBJECT_IDENTIFIERS | IDENTIFIER | Other identifier |
| RESEARCH_SUBJECT_IDENTIFIERS | IDENTIFIER_NAME | The organization providing the identifier |

TABLE 84

Research Subject Types

| Table Name | Entity/Column Name | Description |
|---|---|---|
| RESEARCH_SUBJECT_TYPES | ENTITY | The type of research subject (e.g., person, animal, specimen, group, etc.) |
| RESEARCH_SUBJECT_TYPES | RESEARCH_SUBJECT_TYPE_ID | Unique identifier |
| RESEARCH_SUBJECT_TYPES | DESCRIPTION | Textual description or friendly name |

TABLE 85

Research Subjects

| Table Name | Entity/Column Name | Description |
|---|---|---|
| RESEARCH_SUBJECTS | ENTITY | The experimental unit is the physical entity which is the primary unit of interest in a study. In an interventional study, the experimental unit is assigned to an intervention. The experimental unit is also the unit of primary statistical analysis. Commonly the individual subject (animal, person or product) is the experimental unit. Different experimental units must be capable of receiving different experimental interventions. Accordingly if all pigs in a pen receive the same intervention in their feed, and the primary observations and analyses of interest are associated with the entire pen (e.g., total feed consumed, total weight of all pigs combined), then the pen of pigs rather than the individual animal is the experimental unit. This means that the statistical analysis may be incorrect if it is assumed that the pig is the experimental unit. In this case the statistical analysis should normally be done using the mean of all the pigs in the pen. An example of when the experimental unit is a product would be product stress test or product performance studies. |

TABLE 86

Result Types

| Table Name | Entity/Column Name | Description |
|---|---|---|
| RESULT_TYPES | ENTITY | The type of results (e.g., need examples) |
| RESULT_TYPES | RESULT_TYPE_ID | Unique identifier |
| RESULT_TYPES | CODE | Code from the coding system |
| RESULT_TYPES | CODE_SYSTEM | Code system of the code |
| RESULT_TYPES | CODE_SYSTEM_VERSION | Version of the code system version of the code |
| RESULT_TYPES | DESCRIPTION | Friendly name of identifier |

TABLE 87

Results

| Table Name | Entity/Column Name | Description |
| --- | --- | --- |
| RESULTS | ENTITY | Any outcome or actions taken (e.g., stop taking drug) |
| RESULTS | RESULT_ID | Unique Identifier |
| RESULTS | ASSESSMENT_ID | The assessment |
| RESULTS | RESULT_TYPE_ID | The type of result |
| RESULTS | DATA_TYPE_ID | Based on the data type certain fields will be populated. The data type examples include, coded. physical quantity, string, real |
| RESULTS | RESULT_REAL | Used when the data type is physical quantity, ratio or real. Result in a numeric value of the observation |
| RESULTS | RESULT_UNIT_ID | Used when the data type is physical quantity or ratio. The unit of measure of the result. The numeric value will be located in the result_real. |
| RESULTS | RESULT_STRING | Used when the data type is string. The result of the observation |
| RESULTS | RESULT_DATE_LOW | Used when the data type is date. The result of the observation |
| RESULTS | RESULT_DATE_HIGH | Used when the data type is date. The result of the observation |
| RESULTS | RESULT_DENOM_REAL | Used when the data type is ratio. The numeric denominator result of the operation |
| RESULTS | RESULT_DENOM_UNIT_ID | Used when the data type is ration. The unit of measure of the denominator of the result of the observation |
| RESULTS | RESULT_SOURCE | Original text of the result |
| RESULTS | RESULT_SOURCE_UNIT | Original text of the result unit |

TABLE 88

Routes of Administration

| Table Name | Entity/Column Name | Description |
| --- | --- | --- |
| ROUTES | ENTITY | The physiological path or route for introducing the therapeutic material into or onto the subject. |
| ROUTES | ROUTE_ID | Unique identifier |
| ROUTES | DESCRIPTION_ | Friendly name of identifier |
| ROUTES | CODE | Code from the coding system |
| ROUTES | CODE_SYSTEM | Code system of the code |
| ROUTES | CODE_SYSTEM_VERSION | Version of the code system version of the code |

TABLE 89

Service Delivery Location

| Table Name | Entity/Column Name | Description |
| --- | --- | --- |
| SERVICE_DELIVERY_LOCATIONS | ENTITY | The physical location of activities |
| SERVICE_DELIVERY_LOCATIONS | LOCATION_TYPE_ID | The type of the location (e.g., hospital, clinic) |

TABLE 90

Service Provider

| Table Name | Entity/Column Name | Description |
| --- | --- | --- |
| SERVICE_PROVIDERS | ENTITY | There are many service providers that are involved in a study. It is important to list some, not all, service providers involved in a study. For example, this information could be used to find all contract research organizations involved in all active studies. |
| SERVICE_PROVIDERS | SERVICE_PROVIDER_ID | Unique identifier |
| SERVICE_PROVIDERS | NAME | Name of provider |

TABLE 91

Service Provider in Study

| Table Name | Entity/Column Name | Description |
| --- | --- | --- |
| SERVICE_PROVIDERS_STUDIES | ENTITY | One service provider and provide services for many studies |
| SERVICE_PROVIDERS_STUDIES | SERVICE_PROVIDER_ID | Service provider |
| SERVICE_PROVIDERS_STUDIES | SITE_ID | Site where the services take place |
| SERVICE_PROVIDERS_STUDIES | STUDY_MASTER_ID | Study of the services |

TABLE 92

Sites

| Table Name | Entity/Column Name | Description |
| --- | --- | --- |
| SITES | ENTITY | Site of the study. |

TABLE 93

Species

| Table Name | Entity/Column Name | Description |
| --- | --- | --- |
| SPECIES | ENTITY | The type or kind of animal/virus/organism |
| SPECIES | SPECIES_ID | Unique identifier |
| SPECIES | DESCRIPTION | Friendly name of identifier |
| SPECIES | CODE | Code from the coding system |
| SPECIES | CODE_SYSTEM | Code system of the code |
| SPECIES | CODE_SYSTEM_VERSION | Version of the code system version of the code |

TABLE 94

Specimen Types

| Table Name | Entity/Column Name | Description |
| --- | --- | --- |
| SPECIMEN_TYPES | ENTITY | categorize the type of specimen |
| SPECIMEN_TYPES | SPECIMEN_TYPE_ID | Unique identifier |
| SPECIMEN_TYPES | DESCRIPTION | Friendly name of identifier |
| SPECIMEN_TYPES | CODE | Code from the coding system |
| SPECIMEN_TYPES | CODE_SYSTEM | Code system of the code |
| SPECIMEN_TYPES | CODE_SYSTEM_VERSION | Version of the code system version of the code |

TABLE 95

Specimen

| Table Name | Entity/Column Name | Description |
|---|---|---|
| SPECIMENS | ENTITY | A sample used for analysis or diagnosis |
| SPECIMENS | SPECIMEN_ID | Unique identifier |
| SPECIMENS | SPECIMEN_TYPE_ID | categorize the type of specimen |
| SPECIMENS | PROCEDURE_ID | Procedure, if any, used to extract the specimen |
| SPECIMENS | COLLECTED_LOW | Date when the specimen was collected |
| SPECIMENS | COLLECTED_HIGH | Date when the specimen was collected |
| SPECIMENS | SOURCE_ID | Identifier of the specimen as per the source document |

TABLE 96

Status

| Table Name | Entity/Column Name | Description |
|---|---|---|
| STATUSES | ENTITY | Different states. This is a look up table. |

TABLE 97

Study Site Location

| Table Name | Entity/Column Name | Description |
|---|---|---|
| STUDIES_SITE_LOCATIONS | ENTITY | The same location can be used for many sites |

TABLE 98

Study Sites

| Table Name | Entity/Column Name | Description |
|---|---|---|
| STUDIES_SITES | ENTITY | The main location where study actual activities are conducted. One site can be for many studies |
| STUDIES_SITES | SITE ID | Unique identifier |
| STUDIES_SITES | STUDY_MASTER_ID | With site id, this is the unique identifier |
| STUDIES_SITES | SOURCE_ID | The identifier of the study site in the source document |

TABLE 99

Study Sites Statuses

| Table Name | Entity/Column Name | Description |
|---|---|---|
| STUDIES_SITES_STATUSES | ENTITY | The status of site. The status could be null (not started), in progress, hold or complete |

TABLE 100

Study Characteristic Types

| Table Name | Entity/Column Name | Description |
|---|---|---|
| STUDY_CHARACTERISTIC_TYPES | ENTITY | The type of study characteristics (e.g.; blinding schema, intent, phase, randomization, objectives, blinding Schema, confidentiality, monitor disease, intent, phase randomized Indicator, populated description, intervention, duration, study duration) |
| STUDY_CHARACTERISTIC_TYPES | STUDY_CHARACTERISTIC_TYPE_ID | Unique identifier |
| STUDY_CHARACTERISTIC_TYPES | CODE | Code from the coding system |
| STUDY_CHARACTERISTIC_TYPES | CODE_SYSTEM | Code system of the code |
| STUDY_CHARACTERISTIC_TYPES | CODE_VERSION | Version of the code system version of the code |
| STUDY_CHARACTERISTIC_TYPES | DESCRIPTION | Friendly name of identifier |

TABLE 101

Study Definition

| Table Name | Entity/Column Name | Description |
|---|---|---|
| STUDY_DEFINITIONS | ENTITY | An action plan for a formal investigation to assess the utility, impact, pharmacological, physiological, and psychological effects of a particular treatment, procedure, drug, device, biologic, food product, cosmetic, care plan, or subject characteristic. Note: Among other things, the action plan may include the design, statistical considerations and all planned activities to test a particular hypothesis that is the basis of the study. Subjects may be biological entities (human, animal, specimen, tissue, organ, etc.) or products. |

TABLE 101-continued

Study Definition

| Table Name | Entity/Column Name | Description |
| --- | --- | --- |
| | | The study may be of any type that involves subjects, including prevention, therapeutic, interventional or observational. |
| STUDY_DEFINITIONS | STUDY_DEFINITION_ID | Unique Identifier |
| STUDY_DEFINITIONS | TITLE | A brief description of the study. |
| STUDY_DEFINITIONS | SOURCE_ID | Identifier in the source document |
| STUDY_DEFINITIONS | DESCRIPTION | Full description of the study |
| STUDY_DEFINITIONS | VERSION | Protocol version number |
| STUDY_DEFINITIONS | MODIFIED_REASON | Reason for modification |
| STUDY_DEFINITIONS | IS_CURRENT | Is this study definition the most current study definition |

TABLE 102

Study Definition Sites

| Table Name | Entity/Column Name | Description |
| --- | --- | --- |
| STUDY_DEFINITIONS_SITES | ENTITY | A study site uses a version of a protocol at a certain time |
| STUDY_DEFINITIONS_SITES | START | start date of protocol version |
| STUDY_DEFINITIONS_SITES | END | End date of the protocol version |

TABLE 103

Study Events

| Table Name | Entity/Column Name | Description |
| --- | --- | --- |
| STUDY_EVENTS | ENTITY | The study that is executed. The same study can be executed many times |
| STUDY_EVENTS | DATE_LOW | The start of the study |
| STUDY_EVENTS | DATE_HIGH | The end of the study |

TABLE 104

Study Event Statuses

| Table Name | Entity/Column Name | Description |
| --- | --- | --- |
| STUDY_EVENTS_STATUSES | ENTITY | The status of study. The status could be null (not started), in progress, hold or complete |

TABLE 105

Study Identifiers

| Table Name | Entity/Column Name | Description |
| --- | --- | --- |
| STUDY_IDENTIFIERS | ENTITY | A study can have many identifiers |
| STUDY_IDENTIFIERS | STUDY_MASTER_ID | Unique identifier |
| STUDY_IDENTIFIERS | IDENTIFIER | The alternative identifier |
| STUDY_IDENTIFIERS | IDENTIFIER_NAME | Organization provided the alternative identifier or identifier name |

TABLE 106

Study Master

| Table Name | Entity/Column Name | Description |
| --- | --- | --- |
| STUDY_MASTERS | ENTITY | A study can have many different protocols (study definition) and be executed many different times (study event) |

TABLE 107

Study Status Types

| Table Name | Entity/Column Name | Description |
| --- | --- | --- |
| STUDY_STATUS_TYPES | ENTITY | The status of the study, such as "recruiting subjects" and "active" |

TABLE 108

Subject Protection Approval

| Table Name | Entity/Column Name | Description |
|---|---|---|
| SUBJECT_PROTECTION_APPROVALS | ENTITY | The purpose of a subject protection approval (by an Institutional review board (IRB), independent ethics committee (IEC) or ethical review board (ERB)) is to assure, both in advance and by periodic review, that appropriate steps are taken to protect the rights and welfare of humans participating as subjects in a research study. To accomplish this purpose, ethical committees review research protocols and related materials (e.g., informed consent documents and investigator brochures) to ensure protection of the rights and welfare of human subjects of research. The chief objectives of every ethical committee protocol review are to assess the scientific merit of the research and its methods, to promote fully informed and voluntary participation by prospective subjects who are themselves capable of making such choices (or, if that is not possible, informed permission given by a suitable proxy) and to maximize the safety of subjects once they are enrolled in the project. |
| SUBJECT_PROTECTION_APPROVALS | SUBJECT_PROTECTION_APPROVAL_ID | Unique identifier |
| SUBJECT_PROTECTION_APPROVALS | ETHICAL_COMMITTEE_ID | The ethical committee making the approval judgment |
| SUBJECT_PROTECTION_APPROVALS | EFFECTIVE_DATE_LOW | The period of time during which the approval is in effect. |
| SUBJECT_PROTECTION_APPROVALS | EFFECTIVE_DATE_HIGH | The period of time during which the approval is in effect. |
| SUBJECT_PROTECTION_APPROVALS | AVAILABLE_DATE | When the approval was recorded by the ethical committee. For example, if the ethical committee made a decision on June 4th that the study can be conducted at a certain site for one year started in July 1st. June 4th would be the availability time and July 1st for one year would be the effective time. |
| SUBJECT_PROTECTION_APPROVALS | SITE_ID | The study site that is the subject of the approval |
| SUBJECT_PROTECTION_APPROVALS | STUDY_MASTER_ID | The study master of the site in question |

TABLE 109

Subject Relationship Types

| Table Name | Entity/Column Name | Description |
|---|---|---|
| SUBJECT_RELATIONSHIP_TYPES | ENTITY | The type of relationship (e.g., part. specimen, family member, etc.) |
| SUBJECT_RELATIONSHIP_TYPES | SUBJECT_RELATIONSHIP_TYPE_ID | Unique identifier |
| SUBJECT_RELATIONSHIP_TYPES | DESCRIPTION | Friendly name or description |

TABLE 110

Subject Cross Table

| Table Name | Entity/Column Name | Description |
|---|---|---|
| SUBJECTS_SUBJECTS | ENTITY | The relationship between subjects. e.g., members in a group or people of the specimen |
| SUBJECTS_SUBJECTS | SUBJECT_RELATIONSHIP_TYPE_ID | The type of relationship (e.g., part, specimen, family member, etc.) |

TABLE 111

Substance Administration

| Table Name | Entity/Column Name | Description |
| --- | --- | --- |
| SUBSTANCE_ADMINISTRATIONS | ENTITY | A type of procedure that involves a performer introducing or otherwise applying a product into or to the experimental unit. For purposes of this definition, photons and other models of radiation or light energy are considered substances. Substances may also include living entities such as live virus vaccines and other materials containing infectious agents, e.g., saliva, blood products, etc. |
| SUBSTANCE_ADMINISTRATIONS | SUBSTANCE_ADMINISTRATION_ID | Unique identifier |
| SUBSTANCE_ADMINISTRATIONS | ADMINISTRATION_TYPE_ID | The type of administration |
| SUBSTANCE_ADMINISTRATIONS | PRODUCT_ID | The product that was administered |
| SUBSTANCE_ADMINISTRATIONS | ROUTE_ID | The physiological path or route for introducing the therapeutic product into or onto the subject. |
| SUBSTANCE_ADMINISTRATIONS | ENCOUNTER_ID | The encounter where the administration occurred |
| SUBSTANCE_ADMINISTRATIONS | APPROACH_SITE_ID | The anatomical site or system through which the administration reaches its target. If the route is intravenous or intra-muscular, it may be necessary to specify the precise site, with approach site, (e.g., right forearm or left deltoid muscle respectively) |
| SUBSTANCE_ADMINISTRATIONS | DOSE_UNIT_ID | The unit of measure specified for the dose. The dose may be specified either as a physical quantity of active ingredient (e.g., 200 mg) or as the count of administration-units (e.g., tablets, capsules, etc). |
| SUBSTANCE_ADMINISTRATIONS | DOSE | The amount of the administered substance or other substance given at one administration event |
| SUBSTANCE_ADMINISTRATIONS | DOSE_TEXT | The description of the dose as provided by the source |
| SUBSTANCE_ADMINISTRATIONS | DOSE_MODIFICATION_REASON | The reason why the dose was modified from the protocol |
| SUBSTANCE_ADMINISTRATIONS | NEGATION | That the administration did not occur |
| SUBSTANCE_ADMINISTRATIONS | DESCRIPTION | Description of the administration |
| SUBSTANCE_ADMINISTRATIONS | DATE_EFFECTIVE_HIGH | The date the administration occurred |
| SUBSTANCE_ADMINISTRATIONS | DATE_EFFECTIVE_LOW | The date the administration occurred |
| SUBSTANCE_ADMINISTRATIONS | AVAILABLE_DATE | The point in time at which information about this administration first became available to a system reproducing this administration. The availability date is metadata describing the record, not the administration. |
| SUBSTANCE_ADMINISTRATIONS | PERIOD | A time duration specifying as a reciprocal measure of the frequency at which the administration repeats |
| SUBSTANCE_ADMINISTRATIONS | PERIOD_TIME_UNIT_ID | The unit of measure of the period |
| SUBSTANCE_ADMINISTRATIONS | DURATION | The magnitude of the quantity measured in terms of the unit of the duration |
| SUBSTANCE_ADMINISTRATIONS | DURATION_TIME_UNIT_ID | The unit of measure specified for the duration |
| SUBSTANCE_ADMINISTRATIONS | SOURCE_ID | The id provided by the source document |
| SUBSTANCE_ADMINISTRATIONS | RESEARCH_SUBJECT_ID | The subject of the administration |
| SUBSTANCE_ADMINISTRATIONS | DATA_ENTERER | The person who entered the data |
| SUBSTANCE_ADMINISTRATIONS | MODIFIED_REASON | The reason for the modification |
| SUBSTANCE_ADMINISTRATIONS | MODIFIED_SUB_ADMINISTRATION_ID | The administration records that this records modifies |
| SUBSTANCE_ADMINISTRATIONS | DEVICE_ID | The device that recorded the administration |
| SUBSTANCE_ADMINISTRATIONS | INVESTIGATOR_ID | The investigator that recorded the administration |
| SUBSTANCE_ADMINISTRATIONS | SERVICE_PROVIDER_ID | The service provided that recorded the administration |
| SUBSTANCE_ADMINISTRATIONS | PLANNED_ADMINISTRATION_ID | The planned administration as specified in the protocol |

TABLE 111-continued

| | Substance Administration | |
|---|---|---|
| Table Name | Entity/Column Name | Description |
| SUBSTANCE_ADMINISTRATIONS | TREATMENT_ID | The treatment that this observation is within |
| SUBSTANCE_ADMINISTRATIONS | IS_CURRENT | If true the this record is the most current |

TABLE 112

| | Study Summaries | |
|---|---|---|
| Table Name | Entity/Column Name | Description |
| SUMMARIES | ENTITY | There are several attributes of the study. Each attribute is used to describe the study. It is expected that there would be a controlled terminology to limit the type (code) of the study characteristics. Each code might have a set of controlled terminology as well. Nonetheless, for every attribute type, the data type will be specified. This list of Study Characteristics is currently bound to the Characteristics identified by the CT.gov trial registration data specification. |
| SUMMARIES | SUMMARY_ID | Unique identifier |
| SUMMARIES | STUDY_CHARACTERISTIC_TYPE_ID | The type of study characteristics (e.g.; blinding schema, intent, phase, randomization, objectives, blinding Schema, confidentiality, monitor disease, intent, phase randomized Indicator, populated description, intervention, duration, study duration) |
| SUMMARIES | STUDY_MASTER_ID | The study |
| SUMMARIES | DATATYPE_ID | Based on the data type certain fields will be populated. The data type examples include, coded, physical quantity, string, real |
| SUMMARIES | RESULT_REAL | Used when the data type is physical quantity, ratio or real. Result in a numeric value of the summary |
| SUMMARIES | RESULT_UNIT_ID | Used when the data type is physical quantity or ratio. The unit of measure of the result. The numeric value will be located in the result_real. |
| SUMMARIES | RESULT_STRING | Used when the data type is string. The result of the summary |
| SUMMARIES | RESULT_DATE_LOW | Used when the data type is date. The result of the summary |
| SUMMARIES | RESULT_DATE_HIGH | Used when the data type is date. The result of the summary |
| SUMMARIES | RESULT_DENOM_REAL | Used when the data type is ratio. The numeric denominator result of the operation |
| SUMMARIES | RESULT_DENOM_UNIT_ID | Used when the data type is ratio. The unit of measure of the denominator of the result of the observation |
| SUMMARIES | NEGATION | Explains results that are the opposite of what is stated |
| SUMMARIES | SOURCE_ID | The id provided by the source document |

TABLE 113

| | Supplies | |
|---|---|---|
| Table Name | Entity/Column Name | Description |
| SUPPLIES | ENTITY | Provision of a material by an investigator to the experimental unit. The precise identification of the product (route, dosage form, serial |

TABLE 113-continued

Supplies

| Table Name | Entity/Column Name | Description |
| --- | --- | --- |
| | | numbers, etc.) is important. Most of the detailed information about the Supply should be represented by the product. |
| SUPPLIES | SUPPLY_ID | If true the this record is the most current |
| SUPPLIES | SUPPLY_TYPE_ID | The type of supply - why is this needed |
| SUPPLIES | PRODUCT_ID | The product that is being supplied |
| SUPPLIES | ENCOUNTER_ID | The encounter where the supply occurred |
| SUPPLIES | DATE_EFFECTIVE_HIGH | The date the supply occurred |
| SUPPLIES | DATE_EFFECTIVE_LOW | The date the supply occurred |
| SUPPLIES | DESCRIPTION | Description of the supply |
| SUPPLIES | EXPECTED_USE_HIGH | The period time over which the supplied product is expected to be used. |
| SUPPLIES | EXPECTED_USE_LOW | The period time over which the supplied product is expected to be used. |
| SUPPLIES | EXPECTED_USE_UNIT_ID | The unit of measure specified for the expected use |
| SUPPLIES | DURATION | The magnitude of the quantity measured in terms of the unit of the duration |
| SUPPLIES | DURATION_TIME_UNIT_ID | The unit of measure specified for the duration |
| SUPPLIES | SOURCE_ID | The id provided by the source document |
| SUPPLIES | RESEARCH_SUBJECT_ID | The subject of the administration |
| SUPPLIES | DATA_ENTERER | The person who entered the data |
| SUPPLIES | MODIFIED_REASON | The reason for the modification |
| SUPPLIES | MODIFIED_SUPPY_ID | The supply records that this records modifies |
| SUPPLIES | DEVICE_ID | The device that recorded the supply |
| SUPPLIES | INVESTIGATOR_ID | The investigator that recorded the supply |
| SUPPLIES | SERVICE_PROVIDER_ID | The service provided that recorded the supply |
| SUPPLIES | QUANTITY_UNIT_ID | The unit of measure specified for the quantity |
| SUPPLIES | QUANTITY | The amount of product that is to be supplied. |
| SUPPLIES | PLANNED_SUPPLY_ID | The planned supply as specified in the protocol |
| SUPPLIES | TREATMENT_ID | The treatment that this supply is within |
| SUPPLIES | IS_CURRENT | If true the this record is the most current |

TABLE 114

Supply types

| Table Name | Entity/Column Name | Description |
| --- | --- | --- |
| SUPPLY_TYPES | ENTITY | The type of supply - why is this needed |
| SUPPLY_TYPES | SUPPLY_TYPE_ID | Unique identifier |
| SUPPLY_TYPES | DESCRIPTION | Friendly name of identifier |
| SUPPLY_TYPES | CODE | Code from the coding system |
| SUPPLY_TYPES | CODE_SYSTEM | Code system of the code |
| SUPPLY_TYPES | CODE_SYSTEM_VERSION | Version of the code system version of the code |

TABLE 115

Target Sites

| Table Name | Entity/Column Name | Description |
| --- | --- | --- |
| TARGET_SITES | ENTITY | The anatomical site or system that is the focus of the planned or actual activity. Most activity target sites are implied by the activity type. |
| TARGET_SITES | TARGET_SITE_ID | Unique identifier |
| TARGET_SITES | DESCRIPTION | Friendly name of identifier |

TABLE 115-continued

Target Sites

| Table Name | Entity/Column Name | Description |
|---|---|---|
| TARGET_SITES | CODE | Code from the coding system |
| TARGET_SITES | CODE_SYSTEM | Code system of the code |
| TARGET_SITES | CODE_SYSTEM_VERSION | Version of the code system version of the code |

TABLE 116

Time Units

| Table Name | Entity/Column Name | Description |
|---|---|---|
| TIME_UNITS | ENTITY | The unit of measure of time |
| TIME_UNITS | TIME_UNIT_ID | Unique identifier |
| TIME_UNITS | DESCRIPTION | Friendly name of identifier |
| TIME_UNITS | CODE | Code from the coding system |
| TIME_UNITS | CODE_SYSTEM | Code system of the code |
| TIME_UNITS | CODE_SYSTEM_VERSION | Version of the code system version of the code |

TABLE 117

Treatment Types

| Table Name | Entity/Column Name | Description |
|---|---|---|
| TREATMENT_TYPES | ENTITY | Used to determine the type of the treatment (e.g., screening, pre-op, etc.) |
| TREATMENT_TYPES | TREATMENT_TYPE_ID | Unique identifier |
| TREATMENT_TYPES | NAME | Name of the treatment type |

TABLE 118

Treatments

| Table Name | Entity/Column Name | Description |
|---|---|---|
| TREATMENTS | ENTITY | Studies are organized into discrete units. This organization of the protocol into discrete units is used for study analysis and to describe the conduct of the study. This organization is accomplished through the treatments. Note: Study cell and study segment are both a treatment. Since every study segment is contained wholly within one epoch, at a minimum, in each Arm there are at least as many treatments as there are Epochs. The treatment has two purposes: statistical analysis and scheduling of planned activities. The statistical analysis typically needs only two levels of organization. The top level of organization corresponds to one Epoch. The schedule of planned activities can require several levels of organization. Nevertheless, the statistical analysis organization and schedule of planned activities organization overlap. A treatment, along with the recursive treatments, represents the action plan. Treatments can be a cell, segment, stage, phase, period, cycle. Duration of treatments can be calculated. When the treatment refers to an epoch, then that treatment is a cell (a cell as defined by CDISC's Study Data Tabulation Model). |
| TREATMENTS | TREATMENT_ID | Unique identifier |
| TREATMENTS | TREATMENT_TYPE_ID | The type of treatment, e.g., study, study cell, element, workflow node |
| TREATMENTS | EPOCH_ID | If the treatment is a study cell, then the study cell belongs in one epoch |
| TREATMENTS | OBSERVATION_CRITERIA_ID | The treatment can have many blocking (enter) or exit criteria |
| TREATMENTS | ASSIGNMENT_TYPE_ID | If an assignment occurs to this treatment, is the assignment based on randomization or observation. |
| TREATMENTS | SOURCE_ID | The identifier as provided by the source documents |
| TREATMENTS | STUDY_DEFINITION_ID | The study the treatment belongs to |

TABLE 118-continued

Treatments

| Table Name | Entity/Column Name | Description |
|---|---|---|
| TREATMENTS | TITLE | A word or phrase by which a treatment may be known among people. This is not a formal identifier but rather a human-recognizable common name. Title will not always be used |
| TREATMENTS | ITERATION_LOW | The minimal number of repetitions of the treatment |
| TREATMENTS | ITERATION_HIGH | The maximal number of repetitions of the treatment. A value of negative 1 equals forever. |
| TREATMENTS | DESCRIPTION | Long description of the treatment |
| TREATMENTS | DURATION | The magnitude of the quantity measured in terms of the unit of the duration |
| TREATMENTS | DURATION_TIME_UNIT_ID | The unit of measure specified for the duration |

TABLE 119

Treatment Arms

| Table Name | Entity/Column Name | Description |
|---|---|---|
| TREATMENTS_ARMS | ENTITY | Intersection table to allow for the many to many relationship of a treatment in an arm |
| TREATMENTS_LOCATIONS | ENTITY | The location where the treatment occurs |

TABLE 120

Treatments Planned Subjects

| Table Name | Entity/Column Name | Description |
|---|---|---|
| TREATMENTS_PLANNED_SUBJECTS | ENTITY | A planned subject can receive many treatments |

TABLE 121

Sub Treatments

| Table Name | Entity/Column Name | Description |
|---|---|---|
| TREATMENTS_TREATMENTS | ENTITY | A mechanism to order the execution of the treatment planned activities |
| TREATMENTS_TREATMENTS | PARENT_ID | Parent treatment |
| TREATMENTS_TREATMENTS | CHILD_ID | The child treatment |
| TREATMENTS_TREATMENTS | SEQUENCE | The order the child treatment is executed |

Alternative embodiments of the present invention can store patient information not linked to a study. The planned components can be used as a guideline for the best practices to treat a specified condition. The actual activities do not need to be linked to a study or a guideline. Even without a study or a guideline, embodiments of the present invention can be used to compare different treatments to determine which treatments work best on a population.

Also, a subset of the plurality or set of planned or actual activities may be the same in a plurality of different studies. For example, a blood pressure test in study 1 may be the same blood pressure test in study 2. Likewise, a subset of the plurality or set of assessments may be the same in a plurality of different studies.

The embodiment described above relates to an investigational drug. However, the present invention may be used with an investigational product, which may be an investigational compound (e.g., pharmaceutical drug), an investigational device, or an investigational diagnostic device, agent, or test.

The present invention may be implemented with any combination of hardware and software. If implemented as a computer-implemented apparatus, the present invention is implemented using means for performing all of the steps and functions described above.

When implemented in software, the software code can be executed on any suitable processor or collection of processors, whether provided in a single computer or distributed among multiple computers.

The present invention can also be included in an article of manufacture (e.g., one or more computer program products) having, for instance, computer readable storage media. The storage media has computer readable program code stored therein that is encoded with instructions for execution by a processor for providing and facilitating the mechanisms of the present invention. The article of manufacture can be included as part of a computer system or sold separately.

The storage media can be any known media, such as computer memory, one or more floppy discs, compact discs, optical discs, magnetic tapes, flash memories, circuit configurations in Field Programmable Gate Arrays or other semiconductor devices, or other tangible computer storage medium. The storage media can be transportable, such that the program or programs stored thereon can be loaded onto one or more different computers or other processors to implement various aspects of the present invention as discussed above.

The computers used herein may be embodied in any of a number of foams, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile, or fixed electronic device.

The computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. The computer program need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, and the like, that perform particular tasks or implement particular abstract data types. The functionality of the program modules may be combined or distributed as desired in various embodiments.

Data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A computer for processing data from a plurality of studies of investigational products in a manner that allows data from one study to be compared to data from one or more other studies, wherein each study includes a set of actual activities, the computer comprising:
   (a) memory configured to store an operating system, the operating system including an object-oriented database engine;
   (b) a database schema maintained by the object-oriented database engine of the operating system, the database schema having a plurality of uniquely defined database objects, the uniquely defined database objects including for each study of an investigational product a set of objects that store the set of actual activities, wherein the set of actual activities for each study of an investigational product differ from one another; and
   (c) a database that is populated with data associated with the set of actual activities,
   wherein the set of objects that store the set of actual activities for each study of an investigational product share common attributes and relationships,
   wherein each actual activity has an associated data type, and the associated data type is the same for different studies of investigational products, and
   wherein the set of objects are used to allow the data from one study to be compared to the data from one or more other studies.

2. The computer of claim 1 wherein the investigational product is an investigational compound.

3. The computer of claim 1 wherein the investigational product is an investigational device, or an investigational diagnostic device, agent, or test.

4. The computer of claim 1 wherein a subset of the set of actual activities is the same in a plurality of different studies of investigational products.

5. A computer program product for processing data from a plurality of studies of investigational products in a manner that allows data from one study to be compared to data from one or more other studies, wherein each study includes a set of actual activities, the computer program product comprising non-transitory computer-readable media encoded with instructions for execution by a processor to perform a method comprising:
   (a) configuring an operating system that includes an object-oriented database engine;
   (b) maintaining a database schema by the object-oriented database engine of the operating system, the database schema having a plurality of uniquely defined database objects, the uniquely defined database objects including for each study of an investigational product a set of objects that store the set of actual activities, wherein the set of actual activities for each study of an investigational product differ from one another; and
   (c) maintaining a database that is populated with data associated with the set of actual activities,
   wherein the set of objects that store the set of actual activities for each study of an investigational product share common attributes and relationships, and
   wherein each actual activity has an associated data type, and the associated data type is the same for different studies of investigational products, and wherein the set of objects are used to allow the data from one study to be compared to the data from one or more other studies.

6. The computer program product of claim 5 wherein the investigational product is an investigational compound.

7. The computer program product of claim 5 wherein the investigational product is an investigational device, or an investigational diagnostic device, agent, or test.

8. The computer program product of claim 5 wherein a subset of the set of actual activities is the same in a plurality of different studies of investigational products.

9. A computer for processing data from a study of an investigational product, wherein each study includes (i) a plurality of planned activities, and (ii) a plurality of actual activities, the computer processing the data in a manner that allows the plurality of planned activities to be compared to the plurality of actual activities, the computer comprising:
 (a) memory configured to store an operating system, the operating system including an object-oriented database engine;
 (b) a database schema maintained by the object-oriented database engine of the operating system, the database schema having a plurality of uniquely defined database objects, the uniquely defined database objects including for each study of an investigational product:
  (i) a first set of objects that store the plurality of planned activities,
  (ii) a second set of objects that store the plurality of actual activities, and
 (c) a database that is populated with data associated with the plurality of planned activities and the actual activities,
 wherein the first set of objects that store the plurality of planned activities for the study of an investigational product share common attributes and relationships, and the second set of objects that store the plurality of actual activities for the study of an investigational product share common attributes and relationships, and
 wherein the first and second set of objects are used to allow the plurality of planned activities to be compared to the plurality of actual activities.

10. The computer of claim 9 wherein the study of an investigational product further includes a study definition that includes the plurality of planned activities.

11. The computer of claim 9 wherein the investigational product is an investigational compound.

12. The computer of claim 9 wherein the investigational product is an investigational device, or an investigational diagnostic device, agent, or test.

13. The computer of claim 9 wherein a subset of the plurality of planned activities and a subset of the plurality of actual activities is the same in a plurality of different studies of investigational products.

14. A computer program product for processing data from a study of an investigational product in a manner that allows for data comparison, wherein each study includes (i) a plurality of planned activities, and (ii) a plurality of actual activities, the computer program product processing the data in a manner that allows the plurality of planned activities to be compared to the plurality of actual activities, the computer program product comprising non-transitory computer-readable media encoded with instructions for execution by a processor to perform a method comprising:
 (a) configuring an operating system that includes an object-oriented database engine;
 (b) maintaining a database schema by the object-oriented database engine of the operating system, the database schema having a plurality of uniquely defined database objects, the uniquely defined database objects including for each study of an investigational product:
  (i) a first set of objects that store the plurality of planned activities, and
  (ii) a second set of objects that store the plurality of actual activities; and
 (c) maintaining a database that is populated with data associated with the plurality of planned activities and the plurality of actual activities,
 wherein the first set of objects that store the plurality of planned activities for the study of an investigational product share common attributes and relationships, and the second set of objects that store the plurality of actual activities for the study of an investigational product share common attributes and relationships, and
 wherein the first and second set of objects are used to allow the plurality of planned activities to be compared to the plurality of actual activities.

15. The computer program product of claim 14 wherein the study further includes a study definition that includes the plurality of planned activities.

16. The computer program product of claim 14 wherein the investigational product is an investigational compound.

17. The computer program product of claim 14 wherein the investigational product is an investigational device, or an investigational diagnostic device, agent, or test.

18. The computer program product of claim 14 wherein a subset of the plurality of planned activities and a subset of the plurality of actual activities is the same in a plurality of different studies.

19. A computer for processing data from a plurality of studies of investigational products in a manner that allows data from one study to be compared to data from one or more other studies, wherein each study includes (i) a plurality of planned activities, and (ii) a plurality of actual activities, the computer comprising:
 (a) memory configured to store an operating system, the operating system including an object-oriented database engine;
 (b) a database schema maintained by the object-oriented database engine of the operating system, the database schema having a plurality of uniquely defined database objects, the uniquely defined database objects including for each study of an investigational product:
  (i) a first set of objects that store the plurality of planned activities,
  (ii) a second set of objects that store the plurality of actual activities, and
 (c) a database that is populated with data associated with the plurality of planned activities and the plurality of actual activities,
 wherein the first set of objects that store the plurality of planned activities and the second set of objects that store the plurality of actual activities for each study of an investigational product share common attributes and relationships, and
 wherein each planned activity and each actual activity has an associated data type, and the associated data type is the same for different studies of investigational products, and
 wherein the first and second set of objects are used to allow the data from one study to be compared to the data from one or more other studies.

20. The computer of claim 19 wherein the study of an investigational product further includes a study definition that includes the plurality of planned activities.

21. The computer of claim 19 wherein the investigational product is an investigational compound.

22. The computer of claim 19 wherein the investigational product is an investigational device, or an investigational diagnostic device, agent, or test.

23. The computer of claim 19 wherein a subset of the plurality of planned activities and a subset of the plurality of actual activities is the same in a plurality of different studies of investigational products.

24. A computer program product for processing data from a plurality of studies of investigational products in a manner that allows data from one study to be compared to data from one or more other studies, wherein each study includes (i) a plurality of planned activities and (ii) a plurality of actual activities, the computer program product comprising non-transitory computer-readable media encoded with instructions for execution by a processor to perform a method comprising:
 (a) configuring an operating system that includes an object-oriented database engine;
 (b) maintaining a database schema by the object-oriented database engine of the operating system, the database schema having a plurality of uniquely defined database objects, the uniquely defined database objects including for each study of an investigational product:
  (i) a first set of objects that store the plurality of planned activities, and
  (ii) a second set of objects that store the plurality of actual activities; and
 (c) maintaining a database that is populated with data associated with the plurality of planned activities and the plurality of actual activities,
 wherein the first set of objects that store the plurality of planned activities and the second set of objects that store the plurality of actual activities for each study of an investigational product share common attributes and relationships, and
 wherein each planned activity and each actual activity has an associated data type, and the associated data type is the same for different studies of investigational products, and
 wherein the first and second set of objects are used to allow the data from one study to be compared to the data from one or more other studies.

25. The computer program product of claim 24 wherein the study of an investigational product further includes a study definition that includes the plurality of planned activities.

26. The computer program product of claim 24 wherein the investigational product is an investigational compound.

27. The computer program product of claim 24 wherein the investigational product is an investigational device, or an investigational diagnostic device, agent, or test.

28. The computer program product of claim 24 wherein a subset of the plurality of planned activities and the plurality of actual activities is the same in a plurality of different studies of investigational products.

29. A computer for processing data from a plurality of studies of investigational products in a manner that allows data from one study to be compared to data from one or more other studies, wherein each study includes (i) a plurality of actual activities; and (ii) a plurality of assessments, the computer comprising:
 (a) memory configured to store an operating system, the operating system including an object-oriented database engine;
 (b) a database schema maintained by the object-oriented database engine of the operating system, the database schema having a plurality of uniquely defined database objects, the uniquely defined database objects including for each study of an investigational product:
  (i) a first set of objects that store the plurality of actual activities, and
  (iii) a second set of objects that store the plurality of assessments; and
 (c) a database that is populated with data associated with the plurality of actual activities and the plurality of assessments,
 wherein the first set of objects that store the plurality of actual activities and the second set of objects that store the plurality of assessments for each study of an investigational product share common attributes and relationships, and
 wherein each actual activity and assessment has an associated data type, and the associated data type is the same for different studies of investigational products, and
 wherein the first and second set of objects are used to allow the data from one study to be compared to the data from one or more other studies.

30. The computer of claim 29 wherein the investigational product is an investigational compound.

31. The computer of claim 29 wherein the investigational product is an investigational device, or an investigational diagnostic device, agent, or test.

32. The computer of claim 29 wherein a subset of the plurality of actual activities is the same in a plurality of different studies of investigational products.

33. A computer program product for processing data from a plurality of studies of investigational products in a manner that allows data from one study to be compared to data from one or more other studies, wherein each study includes (i) a plurality of actual activities; and (ii) a plurality of assessments, the computer program product comprising non-transitory computer-readable media encoded with instructions for execution by a processor to perform a method comprising:
 (a) configuring an operating system that includes an object-oriented database engine;
 (b) maintaining a database schema by the object-oriented database engine of the operating system, the database schema having a plurality of uniquely defined database objects, the uniquely defined database objects including for each study of an investigational product:
  (i) a first set of objects that store the plurality of actual activities, and
  (iii) a second set of objects that store the plurality of assessments; and
 (c) maintaining a database that is populated with data associated with the plurality of actual activities and the plurality of assessments,
 wherein the first set of objects that store the plurality of actual activities and the second set of objects that store the plurality of assessments for each study of an investigational product share common attributes and relationships, and
 wherein each actual activity and assessment has an associated data type, and the associated data type is the same for different studies of investigational products, and
 wherein the first and second set of objects are used to allow the data from one study to be compared to the data from one or more other studies.

34. The computer program product of claim 33 wherein the investigational product is an investigational compound.

35. The computer program product of claim 33 wherein the investigational product is an investigational device, or an investigational diagnostic device, agent, or test.

36. The computer program product of claim 33 wherein a subset of the plurality of actual activities is the same in a plurality of different studies of investigational products.

* * * * *

UNITED STATES PATENT AND TRADEMARK OFFICE
CERTIFICATE OF CORRECTION

| | | |
|---|---|---|
| PATENT NO. | : 8,484,254 B1 | Page 1 of 5 |
| APPLICATION NO. | : 13/218637 | |
| DATED | : July 9, 2013 | |
| INVENTOR(S) | : Jason T. Rock | |

It is certified that error appears in the above-identified patent and that said Letters Patent is hereby corrected as shown below:

Title Page, below Abstract "36 Claims, 33 Drawing Sheets" Should read -- 36 Claims, 36 Drawings Sheets -- as attached.

In the Drawings

After sheet 33, insert drawing sheets 34-36 consisting of Figs. 29-31

Signed and Sealed this
Twenty-second Day of April, 2014

Michelle K. Lee
*Deputy Director of the United States Patent and Trademark Office*

(12) United States Patent
Rock

(10) Patent No.: US 8,484,254 B1
(45) Date of Patent: Jul. 9, 2013

(54) RESEARCH STUDY DATABASE TO COMPARE DIFFERENT RESEARCH STUDIES AND TO COMPARE ACTUAL ACTIVITIES COMPARED TO THE PROTOCOL

(75) Inventor: Jason T. Rock, Philadelphia, PA (US)

(73) Assignee: GlobalSubmit, Inc., Philadelphia, PA (US)

(*) Notice: Subject to any disclaimer, the term of this patent is extended or adjusted under 35 U.S.C. 154(b) by 0 days.

(21) Appl. No.: 13/218,637

(22) Filed: Aug. 26, 2011

Related U.S. Application Data

(60) Provisional application No. 61/377,236, filed on Aug. 26, 2010.

(51) Int. Cl.
*G06F 7/00* (2006.01)
*G06F 17/30* (2006.01)

(52) U.S. Cl.
USPC .................. 707/803; 707/804; 707/806

(58) Field of Classification Search
USPC ............................... 707/803, 804, 806
See application file for complete search history.

(56) References Cited

U.S. PATENT DOCUMENTS 6,925,599 B2 * 8/2005 Wood .................. 715/229
2007/0294110 A1 * 12/2007 Settimi .................. 705/3

* cited by examiner

*Primary Examiner* — Mariela Reyes
(74) *Attorney, Agent, or Firm* — Panitch Schwarze Belisario & Nadel LLP

(57) ABSTRACT

A computer is provided for processing data from a plurality of studies of investigational products in a manner that allows the data from one study to be compared to one or more other studies. Each study includes a plurality of planned activities, a plurality of actual activities, and a plurality of assessments. The computer includes a memory, a database schema and a database. The memory is configured to store an operating system which includes an object-oriented database engine. The database schema is maintained by the object-oriented database engine of the operating system. The database schema has a plurality of uniquely defined database objects. For each study, the uniquely defined database objects include respective sets of objects that store the plurality of planned activities, actual activities, and assessments. The database is populated with data associated with the plurality of planned activities, actual activities, and assessments. The respective sets of objects that store the plurality of planned activities, actual activities, and assessments for each study share common attributes and relationships. Each planned activity, actual activity, and assessment has an associated data type that is the same for different studies.

36 Claims, 36 Drawing Sheets

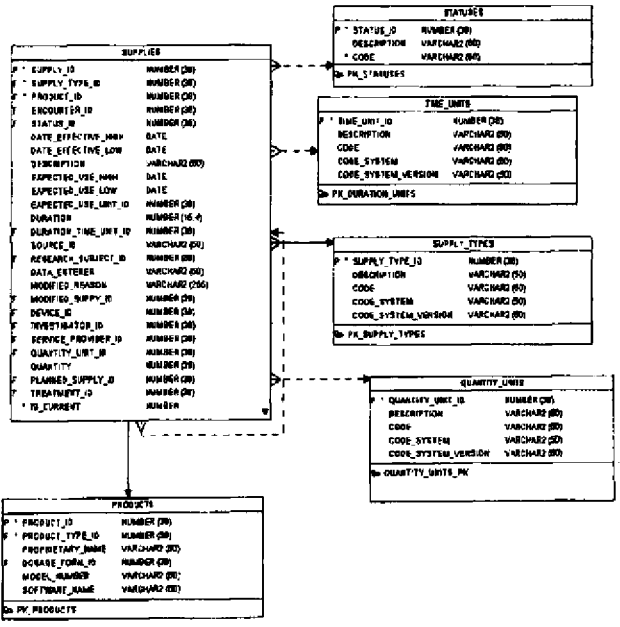

Supplies

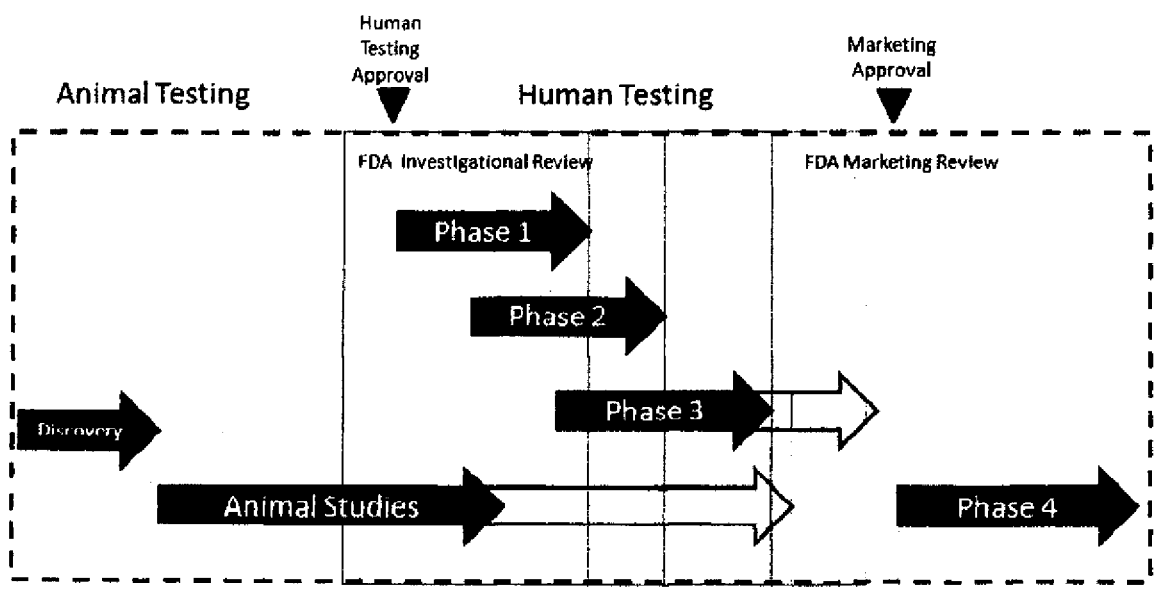
Figure 29: Drug Development Process

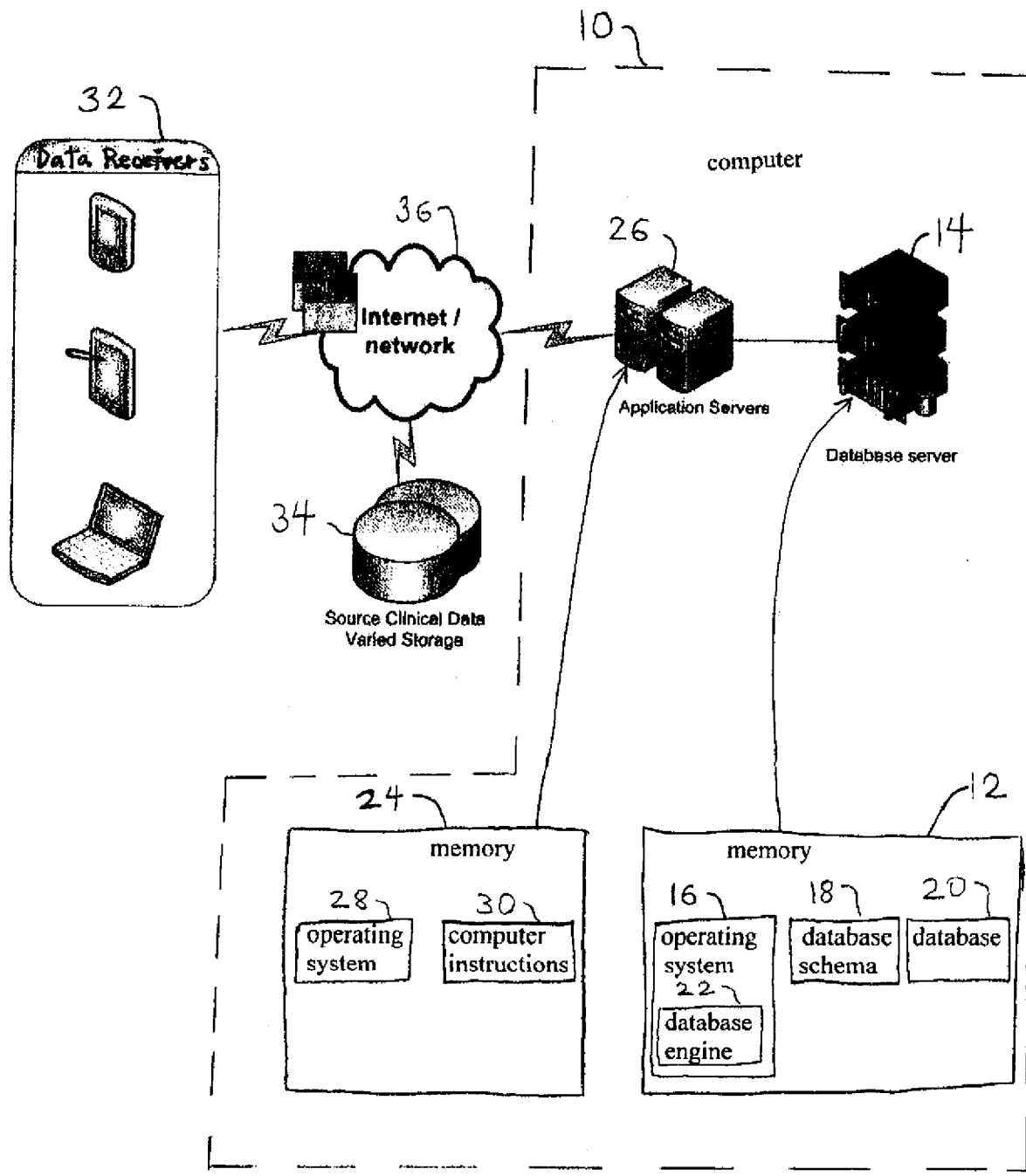
Figure 30: Hardware configuration diagram

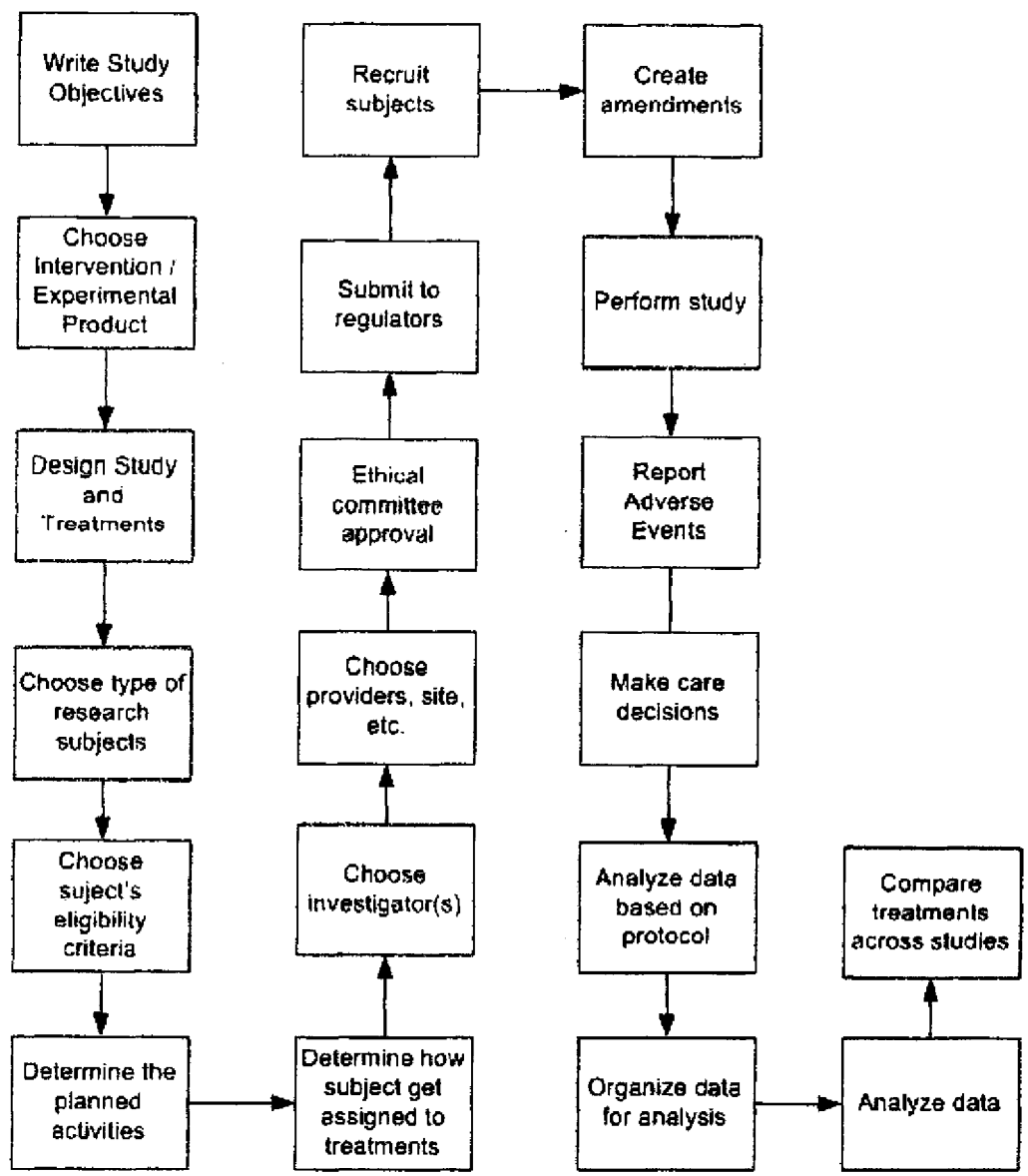
Figure 31: Process Overview